United States Patent
Hancox et al.

(10) Patent No.: US 8,168,633 B2
(45) Date of Patent: *May 1, 2012

(54) THIAZOLOPYRIMIDINES AND THEIR USE AS INHIBITORS OF PHOSPHATIDYLINOSITOL-3 KINASE

(75) Inventors: Timothy Colin Hancox, Slough (GB); Neil Anthony Pegg, Slough (GB); Mandy Christine Beswick, Harlow (GB); Toby Jonathan Blench, Harlow (GB); Elsa Amandine Dechaux, Harlow (GB); Jahusz Jozef Kulagowski, Harlow (GB); Alan John Nadin, Harlow (GB); Stephen Price, Harlow (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/986,317

(22) Filed: Jan. 7, 2011

(65) Prior Publication Data

US 2011/0098270 A1  Apr. 28, 2011

Related U.S. Application Data

(63) Continuation of application No. 12/663,823, filed as application No. PCT/GB2008/002014 on Jun. 12, 2008, now Pat. No. 7,893,060.

(30) Foreign Application Priority Data

Jun. 12, 2007 (GB) .................................. 0711344.2
Aug. 10, 2007 (GB) .................................. 0715677.1

(51) Int. Cl.
  *A61K 31/5377* (2006.01)
(52) U.S. Cl. .................................................. 514/234.2
(58) Field of Classification Search ................ 514/234.2
  See application file for complete search history.

(56) References Cited

U.S. PATENT DOCUMENTS

| | | | |
|---|---|---|---|
| 3,850,917 A | 11/1974 | Mueller et al. | |
| 6,492,383 B1 | 12/2002 | Munchhof et al. | |
| 6,608,056 B1 | 8/2003 | Hayakawa et al. | |
| 7,750,002 B2 | 7/2010 | Shuttleworth et al. | |
| 7,776,856 B2 | 8/2010 | Shuttleworth et al. | |
| 7,893,060 B2 * | 2/2011 | Hancox et al. | 514/234.2 |
| 2007/0185139 A1 | 8/2007 | Binnun et al. | |
| 2008/0039459 A1 | 2/2008 | Folkes et al. | |
| 2008/0076758 A1 | 3/2008 | Folkes et al. | |
| 2008/0076768 A1 | 3/2008 | Chuckowree et al. | |
| 2008/0207609 A1 | 8/2008 | Shuttleworth et al. | |
| 2008/0242665 A1 | 10/2008 | Bayliss et al. | |
| 2008/0269210 A1 | 10/2008 | Castanedo et al. | |
| 2009/0118275 A1 | 5/2009 | Castanedo et al. | |

FOREIGN PATENT DOCUMENTS

| | | |
|---|---|---|
| WO | 2006/114606 | 11/2006 |
| WO | 2007/122410 A1 | 11/2007 |
| WO | 2008/152394 A1 | 12/2008 |

* cited by examiner

*Primary Examiner* — Rebecca Anderson
(74) *Attorney, Agent, or Firm* — Alex Andrus

(57) ABSTRACT

Thiazolopyrimidine compounds of formula I, where W represents a thiazole ring, selectively inhibit the p110 delta subtype of PI3 Kinase (PI3K), and are useful for treating diseases and disorders arising from abnormal cell growth, function or behavior associated with PI3 kinase such as cancer, immune disorders, cardiovascular disease, viral infection, inflammation, metabolism/endocrine function disorders and neurological disorders.

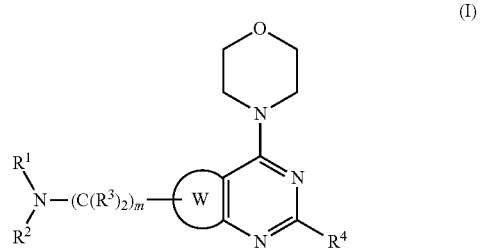

12 Claims, No Drawings

THIAZOLOPYRIMIDINES AND THEIR USE AS INHIBITORS OF PHOSPHATIDYLINOSITOL-3 KINASE

RELATED APPLICATIONS

This application is a continuation application of U.S. Ser. No. 12/663,823, filed Dec. 9, 2009, now issued as U.S. Pat. No. 7,893,060, as a National Stage Application under 35 U.S.C. §371 and claims the benefit of priority to International Application No. PCT/GB2008/002014 having an International Filing Date of 12 Jun. 2008 which claims the benefit of priority of United Kingdom Application Serial Numbers 0711344.2 filed on 12 Jun. 2007 and 0715677.1 filed on 10 Aug. 2007, each of which are herein incorporated by reference in their entireties.

FIELD OF THE INVENTION

The present invention relates to indolyl thiazolopyrimidine compounds and to their use as inhibitors of phosphatidylinositol 3-kinase (PI3K).

BACKGROUND TO THE INVENTION

Phosphatidylinositol (hereinafter abbreviated as "PI") is one of a number of phospholipids found in cell membranes. In recent years it has become clear that PI plays an important role in intracellular signal transduction. In the late 1980s, a PI3 kinase (PI3K) was found to be an enzyme which phosphorylates the 3-position of the inositol ring of phosphatidylinositol (D. Whitman et al. 1988, Nature, 332, 664).

PI3K was originally considered to be a single enzyme, but it has now been clarified that a plurality of subtypes are present in PI3K. Each subtype has its own mechanism for regulating activity. Three major classes of PI3Ks have been identified on the basis of their in vitro substrate specificity (B. Vanhaesebroeck (1997) Trend in Biol. Sci, 22, 267). Substrates for class I PI3Ks are PI, PI 4-phosphate (PI4P) and PI 4,5-biphosphate (P1 (4,5)P2). Class I PI3Ks are further divided into two groups, class Ia and class Ib, in terms of their activation mechanism. Class Ia PI3Ks include PI3K p110α, p110β and p110δ subtypes, which transmit signals from tyrosine kinase-coupled receptors. Class Ib PI3K includes a p110γ subtype activated by a G protein-coupled receptor. PI and PI(4)P are known as substrates for class II PI3Ks. Class II PI3Ks include PI3K C2α, C2β and C2γ subtypes, which are characterized by containing C2 domains at the C terminus. The substrate for class III PI3Ks is PI only.

In the PI3K subtypes, the class Ia subtype has been most extensively investigated to date. The three subtypes of class Ia are heterodimers of a catalytic 110 kDa subunit and regulatory subunits of 85 kDa or 55 kDa. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Thus, the class Ia subtypes are considered to be associated with cell proliferation and carcinogenesis, immune disorders and conditions involving inflammation.

WO 01/083456 describes a series of condensed heteroaryl derivatives which have activity as inhibitors of PI3 K and which suppress cancer cell growth.

SUMMARY OF THE INVENTION

It has now been found that a series of novel thiazolopyrimidine compounds have activity as inhibitors of PI3K. The compounds exhibit selectivity for the p110δ subtype of PI3 kinase, over both other class Ia and class Ib PI3Ks. Accordingly, the present invention provides a compound which is a thiazolopyrimidine of formula (I):

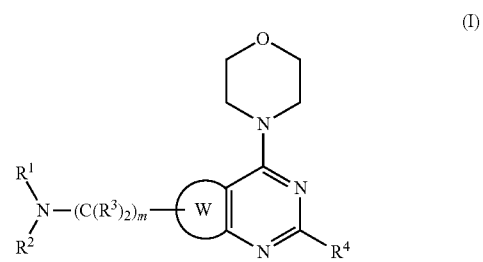

wherein
W represents a thiazole ring;
R$^1$ and R$^2$ form, together with the N atom to which they are attached, a group of the following formula (IIa):

in which A is selected from:
(a) a 4- to 7-membered saturated N-containing heterocyclic ring which includes 0 or 1 additional heteroatoms selected from N, S and O, the ring being unsubstituted or substituted;
(b) a 4- to 7-membered saturated N-containing heterocyclic ring which includes 0 or 1 additional heteroatoms selected from N, S and O, the ring being fused to a second ring selected from a 4- to 7-membered saturated N-containing heterocyclic ring as defined above, a 5- to 12-membered unsaturated heterocyclic ring, a 5- to 7-membered saturated O-containing heterocyclic ring, a 3- to 12-membered saturated carbocyclic ring and an unsaturated 5- to 12-membered carbocyclic ring to form a heteropolycyclic ring system, the heteropolycyclic ring system being unsubstituted or substituted;
(c) a 4- to 7-membered saturated N-containing heterocyclic ring which includes 0 or 1 additional heteroatoms selected from N, S and O and which further comprises, linking two constituent atoms of the ring, a bridgehead group selected from —(CR'$_2$)$_n$— and —(CR'$_2$)$_r$—O—(CR'$_2$)$_s$— wherein each R' is independently H or C$_1$-C$_6$ alkyl, n is 1, 2 or 3, r is 0 or 1 and s is 0 or 1, the remaining ring positions being unsubstituted or substituted; and
(d) a group of formula (IIb):

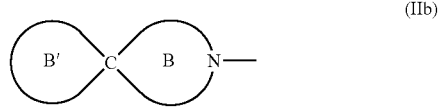

wherein ring B is a 4- to 7-membered saturated N-containing heterocyclic ring which includes 0 or 1 additional heteroatoms selected from N, S and O and ring B' is a 3- to 12-membered saturated carbocyclic ring, a 5- to 7-membered saturated O-containing heterocyclic ring or a 4- to 7-membered saturated N-containing heterocyclic ring as defined above, each of B and B' being unsubstituted or substituted;

or one of $R^1$ and $R^2$ is $C_1$-$C_6$ alkyl and the other of $R^1$ and $R^2$ is selected from a 3- to 12-membered saturated carbocyclic group which is unsubstituted or substituted, a 5- to 12-membered unsaturated carbocyclic group which is unsubstituted or substituted, a 5- to 12-membered unsaturated heterocyclic group which is unsubstituted or substituted, a 4- to 12-membered saturated heterocyclic group which is unsubstituted or substituted and a $C_1$-$C_6$ alkyl group which is substituted by a group selected from a 3- to 12-membered saturated carbocyclic group which is unsubstituted or substituted, a 5- to 12-membered unsaturated carbocyclic group which is unsubstituted or substituted, a 5- to 12-membered unsaturated heterocyclic group which is unsubstituted or substituted and a 4- to 12-membered saturated heterocyclic group which is unsubstituted or substituted;

m is 0, 1 or 2;

$R^3$ is H or $C_1$-$C_6$ alkyl; and $R^4$ is an indole group which is unsubstituted or substituted;

or a pharmaceutically acceptable salt thereof.

DETAILED DESCRIPTION OF THE INVENTION

As used herein, the term "fused" indicates that two rings are joined together by a common bond between two adjacent ring atoms. The term "spiro-fused" indicates that two rings are linked through a single common carbon atom, The term "bridgehead" denotes a linking group, of one or more atoms in length, which connects two non-adjacent ring atoms. In each of these three cases a polycyclic (typically a bicyclic) structure is the result.

When any group, ring, group, ring, substituent or moiety defined herein is substituted, it is typically substituted by Z or $R^5$ as defined below.

A $C_1$-$C_6$ alkyl group is linear or branched. A $C_1$-$C_6$ alkyl group is typically a $C_1$-$C_4$ alkyl group, for example a methyl, ethyl, n-propyl, i-propyl, n-butyl, sec-butyl or tert-butyl group. A $C_1$-$C_6$ alkyl group is unsubstituted or substituted, typically by one or more groups Z or $R^5$ as defined below. Typically it is $C_1$-$C_4$ alkyl, for example methyl, ethyl, i-propyl, n-propyl, t-butyl, s-butyl or n-butyl.

Z is selected from H, unsubstituted $C_1$-$C_6$ alkyl, halo, —OR, —SR, —$(C(R^6)_2)_q$R, —$CH_2$OR, —$CF_3$, -(halo)-$C_1$-$C_6$ alkyl, —$(C(R^6)_2)_q$O-(halo)-$C_1$-$C_6$ alkyl, —$CO_2$R, —$(C(R^6)_2)_q CO_2$R, —$(C(R^6)_2)_q$COR, $CF_2$OH, $CH(CF_3)$OH, $C(CF_3)_2$OH, —$(CH_2)_q$OR, —$(C(R^6)_2)_q$OR, —$(CH_2)_q NR_2$, —$(C(R^6)_2)_q NR_2$, —$C(O)N(R)_2$, —$(C(R^6)_2)_q CONR_2$, —$NR_2$, —$(C(R^6)_2)_q NR_2$, —$(C(R^6)_2)_q NRC(O)R$, —$(C(R^6)_2)_q NRC(O)OR$, —$S(O)_p R$, —$S(O)_p N(R)_2$, —$(C(R^6)_2)_q S(O)_p N(R)_2$, —$OC(O)R$, —$(C(R^6)_2)_q OC(O)R$, —$OC(O)N(R)_2$, —$(C(R^6)_2)_q OC(O)N(R)_2$, —$NRS(O)_p R$, —$(C(R^6)_2)_q NRS(O)_p R$, —$NRC(O)N(R)_2$, —$(C(R^6)_2)_q NRC(O)N(R)_2$, CN, —$NO_2$, =O, a 3- to 12-membered saturated carbocyclic ring which is unsubstituted or substituted, a 5- to 12-membered unsaturated carbocyclic which is unsubstituted or substituted, a 5- to 12-membered unsaturated heterocyclic group which is unsubstituted or substituted and a 4- to 12-membered saturated heterocyclic group which is substituted or unsubstituted, wherein each R is independently selected from H, $C_1$-$C_6$ alkyl, $C_3$-$C_{10}$ cycloalkyl and a 5- to 12-membered aryl or heteroaryl group, the group being unsubstituted or substituted, or when two groups R are attached to an N atom they form, together with the N atom, a 4- to 7-membered saturated N-containing heterocyclic ring; p is 1 or 2 and q is 0, 1 or 2.

$R^5$ is selected from $C_1$-$C_6$ alkoxy, $OR^6$, $SR^6$, $S(O)_p R^6$, nitro, CN, halogen, —$C(O)R^6$, —$CO_2 R^6$, —$C(O)N(R^6)_2$ and —$N(R^6)_2$. $R^6$, each of which is the same or different when more than one is present in a given substituent, is selected from H, $C_1$-$C_6$ alkyl and $C_3$-$C_{10}$ cycloalkyl, and p is 1 or 2.

A halogen or halo group is F, Cl, Br or I. Preferably it is F, Cl or Br. A $C_1$-$C_6$ alkyl group substituted by halogen may be denoted by the term "halo-$C_1$-$C_6$ alkyl", which means an alkyl group in which one or more hydrogens is replaced by halo. A halo-$C_1$-$C_6$ alkyl group preferably contains one, two or three halo groups. A preferred example of such a group is trifluoromethyl.

A $C_1$-$C_6$ alkoxy group is linear or branched. It is typically a $C_1$-$C_4$ alkoxy group, for example a methoxy, ethoxy, propoxy, i-propoxy, n-propoxy, n-butoxy, sec-butoxy or tert-butoxy group. A $C_1$-$C_6$ alkoxy group is unsubstituted or substituted, typically by one or more groups Z or $R^5$ as defined above.

A $C_3$-$C_{10}$ cycloalkyl group may be, for instance, $C_3$-$C_8$ cycloalkyl such as cyclopropyl, cyclobutyl, cyclopentyl, cyclohexyl, or cycloheptyl. Typically it is $C_3$-$C_6$ cycloalkyl. A $C_3$-$C_{10}$ cycloalkyl group is unsubstituted or substituted, typically by one or more groups Z or $R^5$ as defined above.

A 4- to 7-membered saturated N-containing heterocyclic ring typically contains one nitrogen atom and either an additional N atom or an O or S atom, or no additional heteroatoms. It may be, for example, azetidine, pyrrolidine, piperidine, piperazine, morpholine, thiomorpholine or homopiperazine.

A 4- to 7-membered saturated N-containing heterocyclic ring as defined above is unsubstituted or substituted on one or more ring carbon atoms and/or on any additional N atom present in the ring. Examples of suitable substituents include one or more groups Z or $R^5$ as defined above, and a $C_1$-$C_6$ alkyl group which is unsubstituted or substituted by a group Z or $R^5$ as defined above.

Specific examples of a 4- to 7-membered saturated N-containing heterocyclic ring which is substituted as defined above include the following structures:

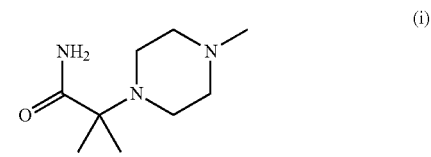

(i)

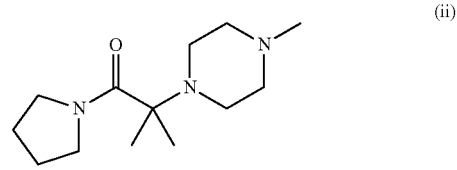

(ii)

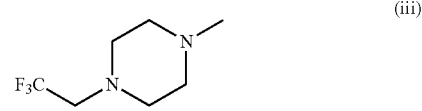

(iii)

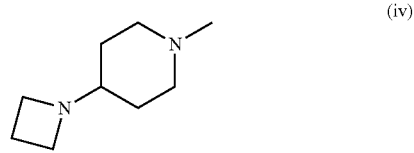

(iv)

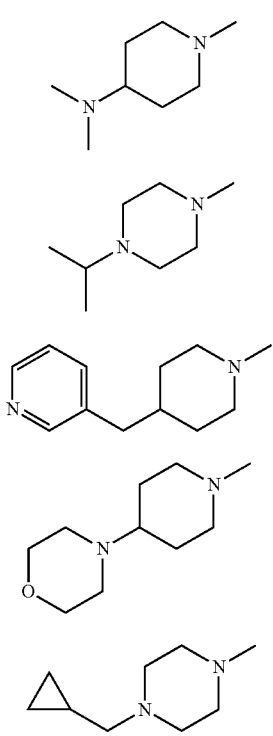

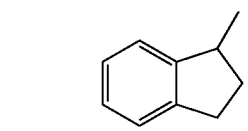

A 5- to 7-membered saturated O-containing heterocyclic ring contains at least one O atom and 0, 1 or 2, typically 0 or 1, additional heteroatoms selected from O, N and S. It is, for instance, tetrahydrofuran, tetrahydropyran, oxetane or morpholine.

A 3- to 12-membered saturated carbocyclic group is a 3-, 4-, 5-, 6-, 7-, 8-, 9-, 10, 11- or 12-membered carbocyclic ring containing only saturated bonds. It is a monocyclic or fused bicyclic ring system. It is, for instance, a 3- to 7-membered saturated carbocyclic ring. Examples include cyclopropane, cyclobutane, cyclopentane, cyclohexane and cycloheptane, and bicyclic ring systems in which two such rings are fused together. Specific examples of a 3- to 12-membered saturated carbocyclic group include the following structures:

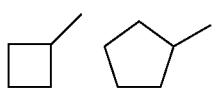

A 5- to 12-membered unsaturated carbocyclic group is a 5-, 6-, 7-, 8-, 9-, 10, 11- or 12-membered carbocyclic ring containing at least one unsaturated bond. It is a monocyclic or fused bicyclic ring system. The group is non-aromatic or aromatic, for instance aryl. Thus, in one embodiment, a 5- to 12-membered unsaturated carbocyclic group is a 5- to 12-membered aryl group. Examples of a 5- to 12-membered unsaturated carbocyclic group include benzene, naphthalene, indane, indene and tetrahydronaphthalene rings, or phenyl, naphthyl, indanyl, indenyl and tetrahydronaphthyl groups. The group is unsubstituted or substituted, typically by one or more groups Z or $R^5$ as defined above. Specific examples of a 5- to 12-membered unsaturated carbocyclic group include the following structure:

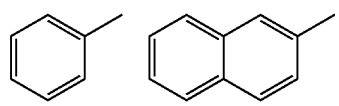

An aryl group is a 5- to 12-membered aromatic carbocyclic group. It is monocyclic or bicyclic. Examples include phenyl and naphthyl groups. The group is unsubstituted or substituted, for instance by a group Z or $R^5$ as defined above. Specific examples of an aryl group include the following structures.

A 5- to 12-membered unsaturated heterocyclic group is a 5-, 6-, 7-, 8-, 9-, 10, 11- or 12-membered heterocyclic ring containing at least one unsaturated bond and at least one heteroatom selected from O, N and S. It is a monocyclic or fused bicyclic ring system. The group is non-aromatic or aromatic, for instance heteroaryl. Thus, in one embodiment a 5- to 12-membered unsaturated heterocyclic group is a 5- to 12-membered heteroaryl group. The 5- to 12-membered unsaturated heterocyclic group may be, for example, furan, thiophene, pyrrole, pyrrolopyrazine, pyrrolopyrimidine, pyrrolopyridine, pyrrolopyridazine, indole, isoindole, pyrazole, pyrazolopyrazine, pyrazolopyrimidine, pyrazolopyridine, pyrazolopyridazine, imidazole, imidazopyrazine, imidazopyrimidine, imidazopyridine, imidazopyridazine, benzimidazole, benzodioxole, benzodioxine, benzoxazole, benzothiophene, benzothiazole, benzofuran, indolizinyl, isoxazole, oxazole, oxadiazole, thiazole, isothiazole, thiadiazole, dihydroimidazole, dihydrobenzofuran, dihydrodioxinopyridine, dihydropyrrolopyridine, dihydrofuranopyridine, dioxolopyridine, pyridine, quinoline, isoquinoline, purine, quinoxaline, tetrahydrobenzofuran, tetrahydroquinoline, tetrahydroisoquinoline, 5,6,7,8-tetrahydro-imidazo[1,5-a]pyrazine, 5,6,7,8-tetrahydro-imidazo[1,2-a]pyrazine, thienopyrazine, pyrimidine, pyridazine, pyrazine, triazine, triazole or tetrazole. The group is unsubstituted or substituted, typically by one or more groups Z or $R^5$ as defined above. Specific examples of a 5- to 12-membered unsaturated heterocyclic group include the following structures:

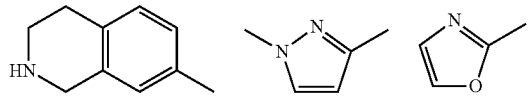

Heteroaryl is a 5- to 12-membered aromatic heterocyclic group which contains 1, 2, 3, or 4 heteroatoms selected from O, N and S. It is monocyclic or bicyclic. Typically it contains one N atom and 0, 1, 2 or 3 additional heteroatoms selected from O, S and N. It may be, for example, a 5- to 7-membered heteroaryl group. Typically it is selected from the heteroaryl groups included in the above list of options for a 5 to 12-membered unsaturated heterocyclic group.

A 4- to 12-membered saturated heterocyclic group is a 4-, 5-, 6-, 7-, 8-, 9-, 10, 11- or 12-membered heterocyclic ring which contains 1, 2, 3, or 4 heteroatoms selected from O, N and S. It is a monocyclic or fused bicyclic ring system. Examples of such heterocyclic rings include, but are not limited to, pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, dithianyl, dithiolanyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. In one embodiment the saturated 4- to 12-membered saturated heterocyclic group is a 4- to 7-membered saturated N-containing heterocyclic ring as defined above, which is unsubstituted or substituted. The saturated 4- to 12-membered heterocyclic group is unsubstituted or substituted, typically by one or more groups Z or $R^5$ as defined above. Further specific examples of a 4- to 12-membered saturated heterocyclic group (in which the heteroatom is O) include the following structures:

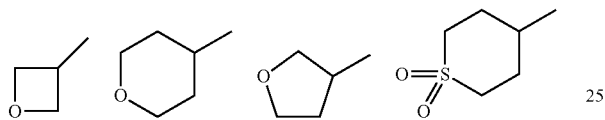

Examples of a 4- to 7-membered saturated N-containing heterocyclic ring which is fused to a second ring as defined above to form a heteropolycyclic ring system include a group selected from azetidine, pyrrolidine, piperidine, piperazine, morpholine, thiomorpholine and homopiperazine, said group being fused to a second ring as defined above. The second ring is typically a 4- to 7-membered saturated N-containing heterocyclic ring as defined above or a 5- to 12-membered unsaturated heterocyclic group. More typically the second ring is a 5-, 6- or 7-membered saturated N-containing heterocyclic ring or a 5- to 7-membered unsaturated heterocyclic ring. Typical examples of the second ring include azetidine, pyrrolidine, piperidine, piperazine, morpholine, thiomorpholine, homopiperazine, pyrrole, imidazole, pyridine, pyridazine, pyrimidine, pyrazine, tetrahydrofuran and tetrahydropyran. Examples of the resulting heteropolycyclic system include octahydro-pyrrolo[1,2-a]pyrazine and octahydro-pyrrolo[3,4-c]pyrrole. Specific examples of the heteropolycyclic system include the following structures:

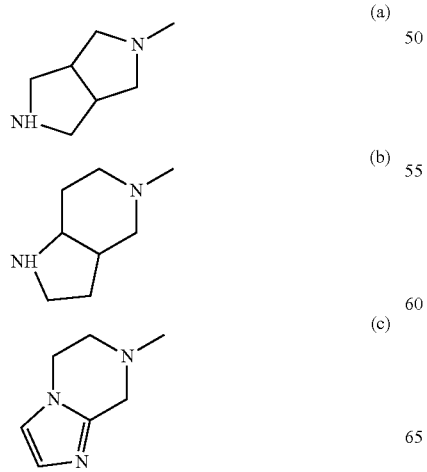

(a)

(b)

(c)

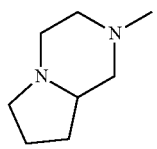

(d)

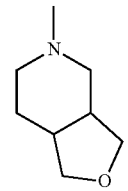

(e)

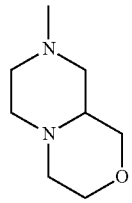

(f)

Examples of a 4- to 7-membered saturated N-containing heterocyclic group as defined above which includes a bridgehead group —(CR'$_2$)$_n$— or —(CR'$_2$)$_r$—O—(CR'$_2$)$_s$— as defined above include 3,8-diaza-bicyclo[3.2.1]octane, 2,5-diaza-bicyclo[2.2.1]heptane, 8-aza-bicyclo[3.2.1]octane, 2-aza-bicyclo[2.2.1]heptane, 3,6-diaza-bicyclo[3.1.1]heptane, 6-aza-bicyclo[3.1.1]heptane, 3,9-diaza-bicyclo[4.2.1]nonane and 3-oxa-7,9-diazabicyclo[3.3.1]nonane.

Specific examples of this group include the following structures:

(a')

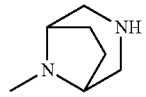

(b')

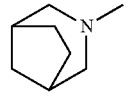

(c')

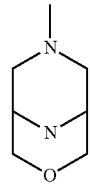

(d')

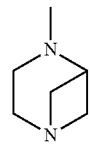

(e')

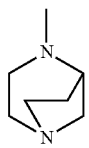

Examples of a group of formula (IIb) as defined above include groups derived from a 4- to 7-membered saturated N-containing heterocyclic group as defined above which is spiro-fused at any available ring carbon atom to a 3 to 12-membered saturated carbocyclic ring, typically to a 3- to 6-membered saturated carbocyclic ring, or to a 4- to 7-membered saturated N-containing heterocyclic group. Examples include a group selected from azetidine, pyrrolidine, piperidine and piperazine which is spiro-fused at a ring carbon atom to a group selected from cyclopropane, cyclobutane, cyclopentane, cyclohexane, azetidine, pyrrolidine, piperidine, piperazine and tetrahydropyran.

The group of formula (IIb) may, for instance, be a group derived from 3,9-diazaspiro[5.5]undecane, 2,7-diazaspiro[3.5]nonane, 2,8-diazaspiro[4.5]decane or 2,7-diazaspiro[4.4]nonane. Specific examples of a group of formula (IIb) include the following structures:

 (i')

 (ii')

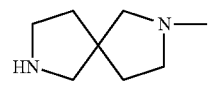 (iii')

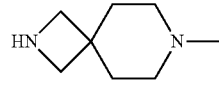 (iv')

 (v')

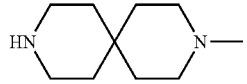 (vi')

 (vii')

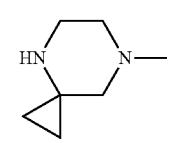 (viii')

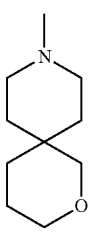 (ix')

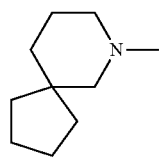 (x')

$R^4$ is an indolyl group which is unsubstituted or substituted. The indolyl group may be linked to the thiazolopyrimidine core via any available ring position. It may, for instance, be an indol-4-yl, indol-5-yl, indol-6-yl or indol-7-yl group. Typically it is indol-4-yl or indol-6-yl, more typically an indol-4-yl group.

When substituted, the indolyl may be substituted at one or more available ring positions. Typically it bears a substituent on the benzene moiety of the indole group. For instance, an indol-4-yl group is typically substituted at the 5-, 6- or 7-position, more typically at the 5- or 6-position. An indol-5-yl group is typically substituted at the 4-, 6- or 7-position, more typically at the 4- or 6-position. An indol-6-yl group is typically substituted at the 4-, 5- or 7-position, more typically at the 4- or 5-position. An indol-7-yl group is typically substituted at the 4-, 5- or 6-position, more typically at the 5- or 6-position.

When the indolyl group is substituted it may be substituted by a group Z or $R^5$ as defined above. In a typical embodiment the indolyl group is substituted by a group selected from R, —OR, —SR, —S(O)$_p$R, CH$_2$OR, —C(O)R, —CO$_2$R, CF$_3$, CF$_2$OH, CH(CF$_3$)OH, C(CF$_3$)$_2$OH, —(CH$_2$)$_q$OR, —(CH$_2$)$_q$NR$_2$, —C(O)N(R)$_2$, —NR$_2$, —N(R)C(O)R, —S(O)$_p$N(R)$_2$, —OC(O)R, OC(O)N(R)$_2$, —N(R)S(O)$_p$R, —NRC(O)N(R)$_2$, CN, halo, —NO$_2$ and a 5-membered heteroaryl group containing 1, 2, 3 or 4 heteroatoms selected from O, N and S, wherein R, p and q are as defined above in the definition of Z. In another typical embodiment the indolyl group is substituted by a group selected from C$_1$-C$_6$ alkyl, CN, halo, —C(O)NR$_2$, halo(C$_1$-C$_6$)alkyl such as CF$_3$, NO$_2$, OR, SR, NR$_2$, C(O)R, SOR, SO$_2$R, SO$_2$NR$_2$, NRC(O)R, CO$_2$R and a 5-membered heteroaryl group as defined above. In another more typical embodiment the indolyl group is substituted by a group selected from CN, halo, —C(O)NR$_2$, halo(C$_1$-C$_6$) alkyl such as CF$_3$, —SO$_2$R, —SO$_2$NR$_2$, and a 5-membered heteroaryl group containing 1, 2, 3 or 4 heteroatoms selected from O, N and S. In the above embodiments R is typically H or C$_1$-C$_6$ alkyl.

Typically the substituent on the indolyl group is an electron-withdrawing group. When the substituent is a 5-membered heteroaryl group it may be, for example, furan, thiophene, pyrrole, imidazole, pyrazole, triazole, tetrazole, oxazole, isoxazole, oxadiazole, thiazole, isothiazole, or thiadiazole.

In one embodiment a substituted indolyl group is an indol-4-yl group substituted at the 5- or 6-position, in particular the 6-position, by CN, halo, —C(O)NH$_2$, —CF$_3$, —SO$_2$Me, —SO$_2$NMe$_2$ or a 5-membered heteroaryl group as defined above. Typically the indol-4-yl group is substituted at the 5- or 6-position by halo, in particular by F. More typically the indol-4-yl group is substituted at the 6-position by halo, in particular by F.

The parameter m in formula (I) is 0, 1 or 2. Typically m is 1 or 2. More typically m is 1.

In formulae (I), a 4- to 12-membered saturated heterocyclic group in the definitions of $R^1$ and $R^2$ may be a 4- to 7-membered saturated N-containing heterocyclic ring which includes 0 or 1 additional heteroatoms selected from N, S and O. A 5- to 12-membered unsaturated heterocyclic group in the definitions of $R^1$ and $R^2$ may be a 5- to 12-membered heteroaryl group. A 5- to 12-membered unsaturated carbocyclic group in the definitions of $R^1$ and $R^2$ may be a 5- to 12-membered aryl group.

In one aspect the invention provides a compound which is a thiazolopyrimidine of formula (I):

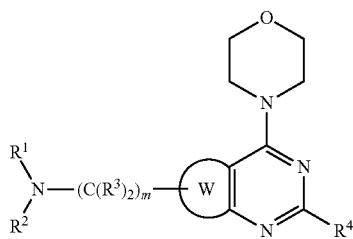

wherein
W represents a thiazole ring;
$R^1$ and $R^2$ form, together with the N atom to which they are attached, a group of the following formula (IIa):

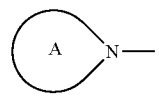

in which A is selected from:
(a) a 4- to 7-membered saturated N-containing heterocyclic ring which includes 0 or 1 additional heteroatoms selected from N, S and O, the ring being unsubstituted or substituted;
(b) a 4- to 7-membered saturated N-containing heterocyclic ring which includes 0 or 1 additional heteroatoms selected from N, S and O, the ring being fused to a second ring selected from a 4- to 7-membered saturated N-containing heterocyclic ring as defined above, a 5- to 12-membered unsaturated heterocyclic ring, a 5- to 7-membered saturated O-containing heterocyclic ring, a 3- to 12-membered saturated carbocyclic ring and an unsaturated 5- to 12-membered carbocyclic ring to form a heteropolycyclic ring system, the heteropolycyclic ring system being unsubstituted or substituted;
(c) a 4- to 7-membered saturated N-containing heterocyclic ring which includes 0 or 1 additional heteroatoms selected from N, S and O and which further comprises, linking two constituent atoms of the ring, a bridgehead group selected from —(CR'$_2$)$_n$— and —(CR'$_2$)$_r$—O—(CR'$_2$)$_s$— wherein each R' is independently H or $C_1$-$C_6$ alkyl, n is 1, 2 or 3, r is 0 or 1 and s is 0 or 1, the remaining ring positions being unsubstituted or substituted; and (d) a group of formula (IIb):

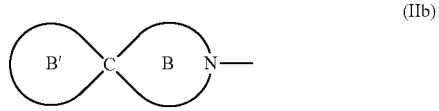

wherein ring B is a 4- to 7-membered saturated N-containing heterocyclic ring which includes 0 or 1 additional heteroatoms selected from N, S and O and ring B' is a 3- to 12-membered saturated carbocyclic ring, a 5- to 7-membered saturated O-containing heterocyclic ring or a 4- to 7-membered saturated N-containing heterocyclic ring as defined above, each of B and B' being unsubstituted or substituted;

or one of $R^1$ and $R^2$ is $C_1$-$C_6$ alkyl and the other is a 4- to 7-membered saturated N-containing heterocyclic ring as defined above or a $C_1$-$C_6$ alkyl group which is substituted by a 4- to 7-membered saturated N-containing heterocyclic ring group as defined above;

m is 0, 1 or 2;
$R^3$ is H or $C_1$-$C_6$ alkyl; and
$R^4$ is an indole group which is unsubstituted or substituted;
or a pharmaceutically acceptable salt thereof.

The thiazole ring W in formula (I) adopts either of the two available regiochemical orientations. Thus, in one embodiment the thiazolopyrimidine is of the following formula (Ia):

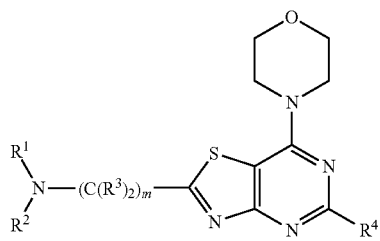

wherein $R^1$, $R^2$, $R^3$, $R^4$ and m are as defined above for formula (I).

In a second embodiment the thiazolopyrimidine is of the following formula (Ib):

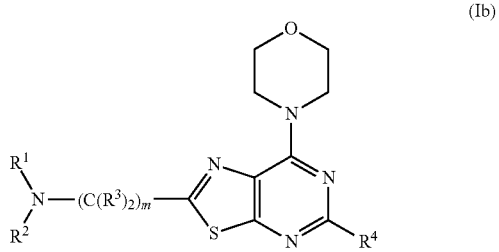

wherein $R^1$, $R^2$, $R^3$, $R^4$ and m are as defined above for formula (I).

Specific examples of compounds of the invention include the compound listed in the following Table:

TABLE 1

| Compound No. | Structure | Name |
|---|---|---|
| 1 | 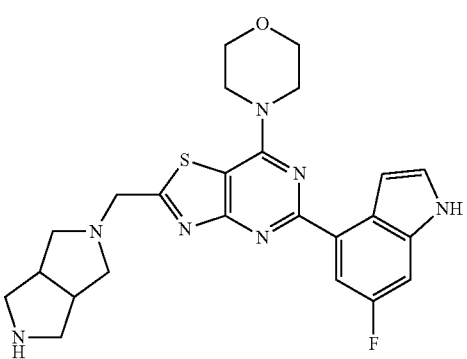 | 5-(6-Fluoro-1H-indol-4-yl)-2-(hexahydro-pyrrolo[3,4-c]pyrrol-2-ylmethyl)-7-morpholin-4-yl-thiazolo[4,5-d]pyrimidine |
| 2 | 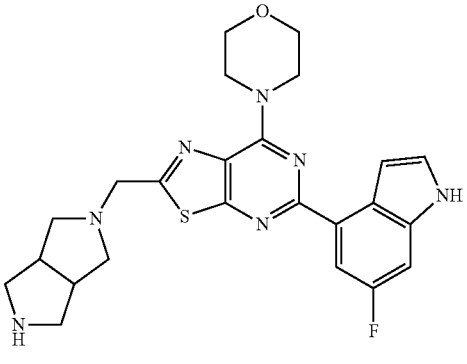 | 5-(6-Fluoro-1H-indol-4-yl)-2-(hexahydro-pyrrolo[3,4-c]pyrrol-2-ylmethyl)-7-morpholin-4-yl-thiazolo[5,4-d]pyrimidine |
| 3 | 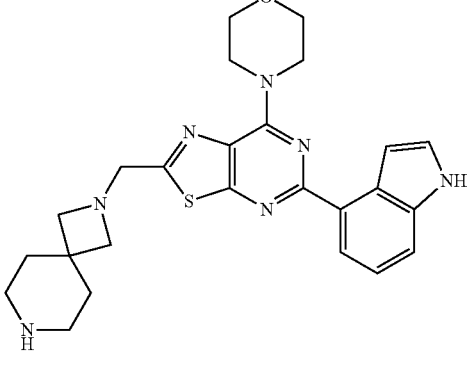 | 2-(2,7-Diaza-spiro[3.5]non-2-ylmethyl)-5-(1H-indol-4-yl)-7-morpholin-4-yl-thiazolo[5,4-d]pyrimidine |
| 4 | 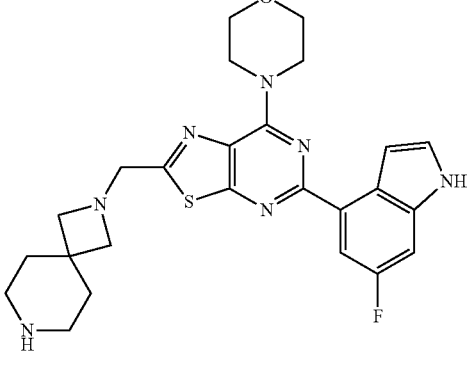 | 2-(2,7-Diaza-spiro[3.5]non-2-ylmethyl)-5-(6-fluoro-1H-indol-4-yl)-7-morpholin-4-yl-thiazolo[5,4-d]pyrimidine |

TABLE 1-continued

| Compound No. | Structure | Name |
|---|---|---|
| 5 | 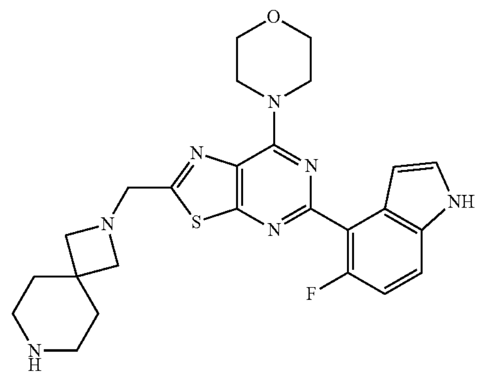 | 2-(2,7-Diaza-spiro[3.5]non-2-ylmethyl)-5-(5-fluoro-1H-indol-4-yl)-7-morpholin-4-yl-thiazolo[5,4-d]pyrimidine |
| 6 | 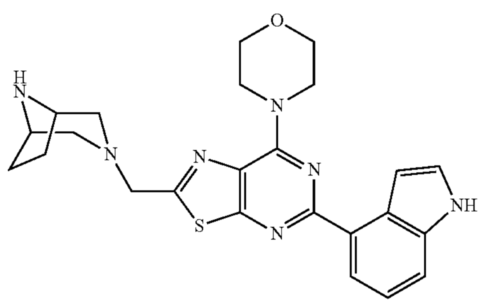 | 2-(3,8-Diaza-bicyclo[3.2.1]oct-3-ylmethyl)-5-(1H-indol-4-yl)-7-morpholin-4-yl-thiazolo[5,4-d]pyrimidine |
| 7 | 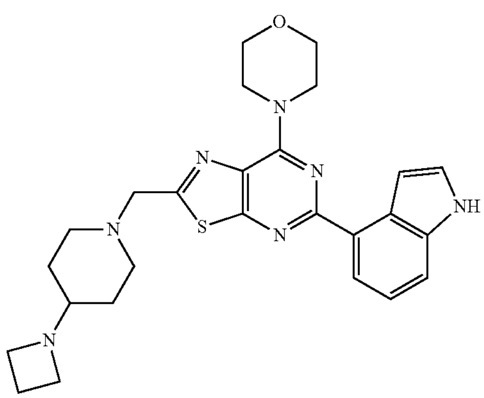 | 2-(4-Azetidin-1-yl-piperidin-1-ylmethyl)-5-(1H-indol-4-yl)-7-morpholin-4-yl-thiazolo[5,4-d]pyrimidine |
| 8 | 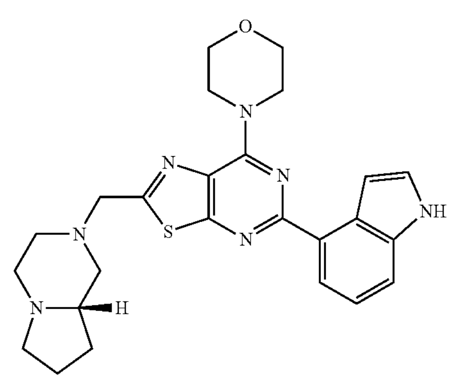 | 2-[(S)-1-(Hexahydro-pyrrolo[1,2-a]pyrazin-2-yl)methyl]-5-(1H-indol-4-yl)-7-morpholin-4-yl-thiazolo[5,4-d]pyrimidine |

TABLE 1-continued

| Compound No. | Structure | Name |
| --- | --- | --- |
| 9 | 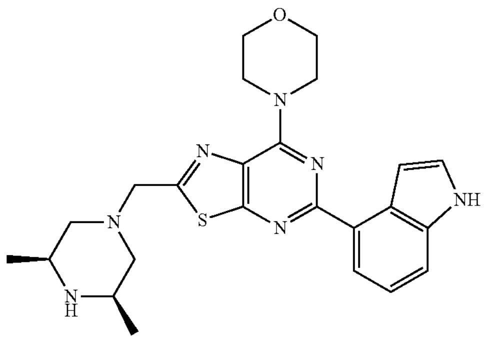 | 2-(3,5-Dimethyl-piperazin-1-ylmethyl)-5-(1H-indol-4-yl)-7-morpholin-4-yl-thiazolo[5,4-d]pyrimidine |
| 10 | 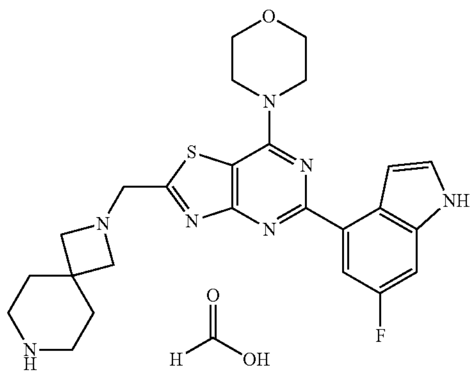 | 2-(2,7-Diaza-spiro[3.5]non-2-ylmethyl)-5-(6-fluoro-1H-indol-4-yl)-7-morpholin-4-yl-thiazolo[4,5-d]pyrimidine formate |
| 11 | 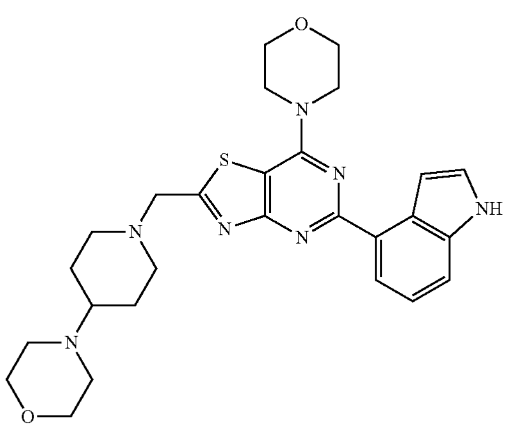 | 5-(1H-Indol-4-yl)-7-morpholin-4-yl-2-(4-morpholin-4-yl-piperidin-1-ylmethyl)-thiazolo[4,5-d]pyrimidine |
| 12 | 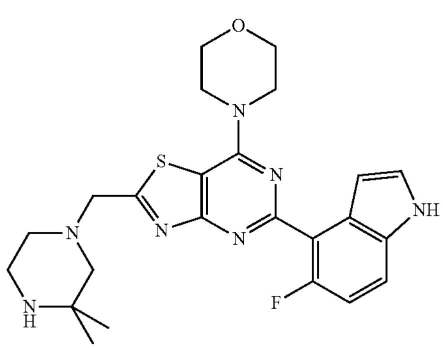 | 2-(3,3-Dimethylpiperazin-1-ylmethyl)-5-(5-fluoro-1H-indol-4-yl)-7-morpholin-4-ylthiazolo[4,5-d]pyrimidine |

TABLE 1-continued

| Compound No. | Structure | Name |
|---|---|---|
| 13 | 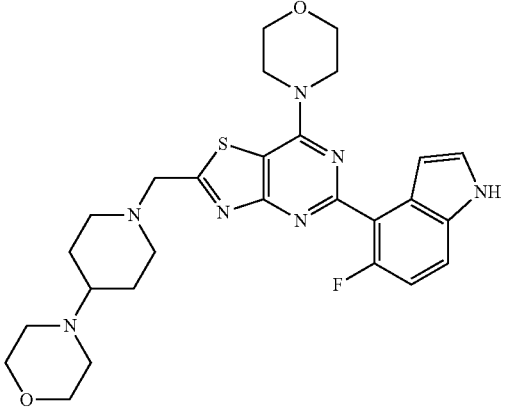 | 5-(5-Fluoro-1H-indol-4-yl)-7-morpholin-4-yl-2-(4-morpholin-4-ylpiperidin-1-ylmethyl)thiazolo[4,5-d]pyrimidine |
| 14 | 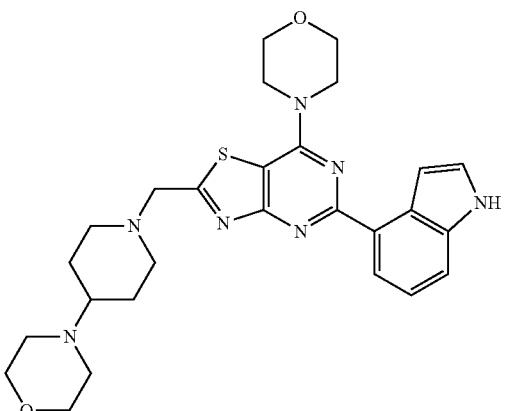 | 5-(1H-Indol-4-yl)-7-morpholin-4-yl-2-(4-morpholin-4-ylpiperidin-1-ylmethyl)thiazolo[4,5-d]pyrimidine |
| 15 | 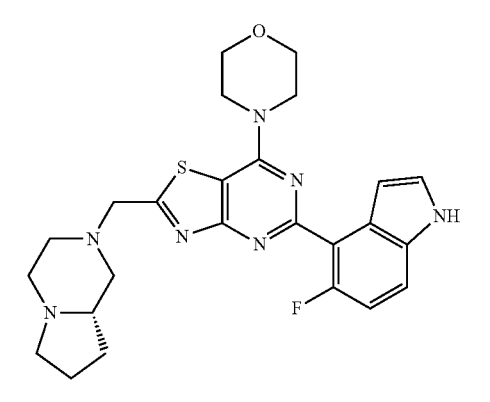 | 5-(5-Fluoro-1H-indol-4-yl)-2-[(S)-1-(hexahydro-pyrrolo[1,2-a]pyrazin-2-yl)methyl]-7-morpholin-4-ylthiazolo[4,5-d]pyrimidine |
| 16 | 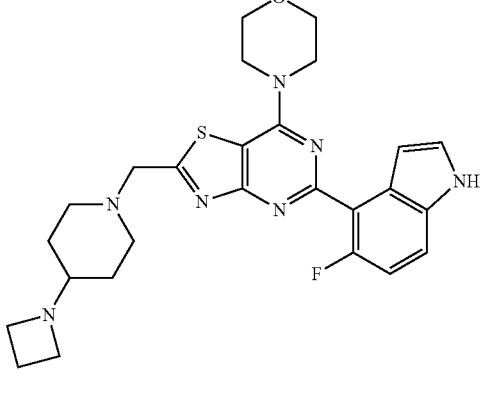 | 2-(4-Azetidin-1-ylpiperidin-1-ylmethyl)-5-(5-fluoro-1H-indol-4-yl)-7-morpholin-4-ylthiazolo[4,5-d]pyrimidine |

TABLE 1-continued

| Compound No. | Structure | Name |
|---|---|---|
| 17 | 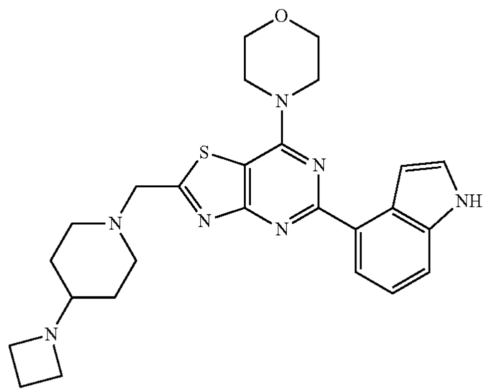 | 2-(4-Azetidin-l-ylpiperidin-1-ylmethyl)-5-(1H-indol-4-yl)-7-morpholin-4-ylthiazolo[4,5-d]pyrimidine |
| 18 | 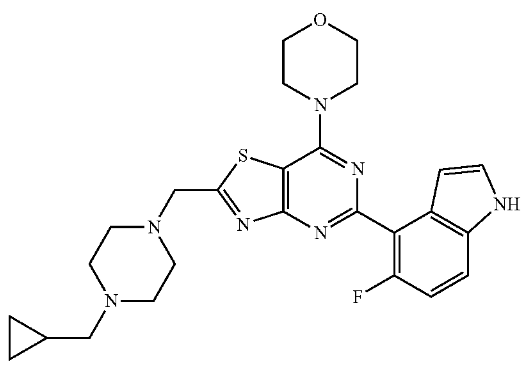 | 2-(4-Cyclopropylmethylpiperazin-1-ylmethyl)-5-(5-fluoro-1H-indol-4-yl)-7-morpholin-4-ylthiazolo[4,5-d]pyrimidine |
| 19 | 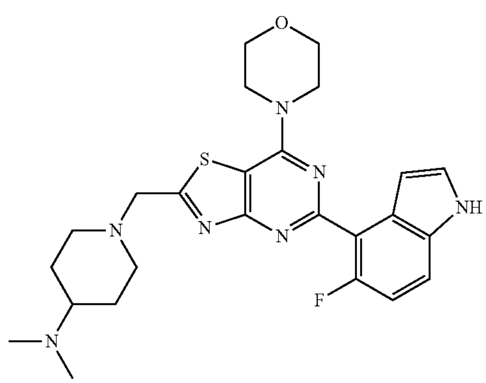 | {1-[5-(5-Fluoro-1H-indol-4-yl)-7-morpholin-4-ylthiazolo[4,5-d]pyrimidin-2-ylmethyl]piperidin-4-yl(dimethylamine |
| 20 | 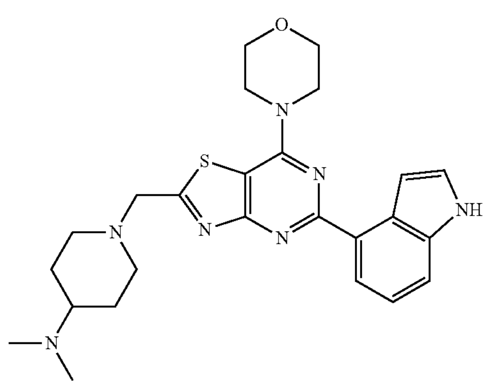 | {1-[5-(1H-Indol-4-yl)-7-morpholin-4-ylthiazol[4,5-d]pyrimidin-2-ylmethyl]piperidin-4-yl}dimethylamine |

TABLE 1-continued

| Compound No. | Structure | Name |
|---|---|---|
| 21 | 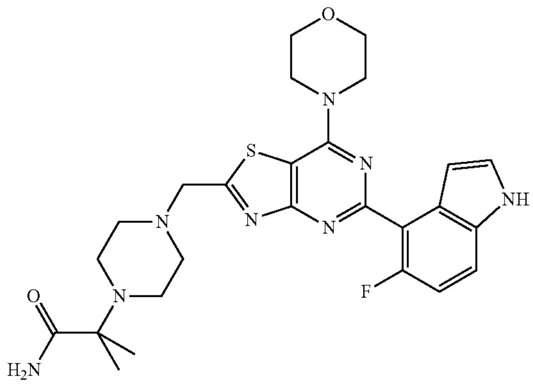 | 2-{4-[5-(5-Fluoro-1H-indol-4-yl)-7-morpholin-4-yl-thiazolo[4,5-d]pyrimidin-2-ylmethyl]-piperazin-1-yl}-isobutyramide |
| 22 | 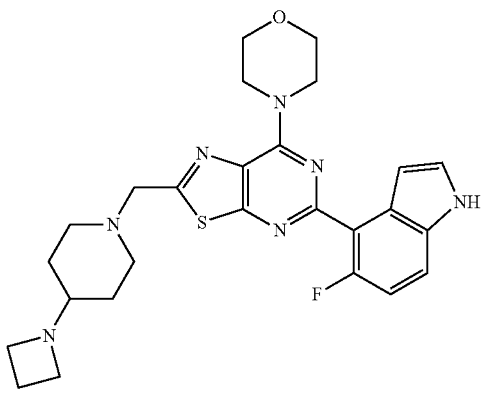 | 2-(4-Azetidin-1-ylpiperidin-1-ylmethyl)-5-(5-fluoro-1H-indol-4-yl)-7-morpholin-4-ylthiazolo[5,4-d]pyrimidine |
| 23 | 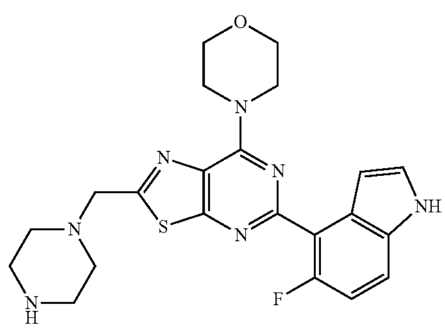 | 5-(5-Fluoro-1H-indol-4-yl)-7-morpholin-4-yl-2-piperazin-1-ylmethylthiazolo[5,4-d]pyrimidine |
| 24 | 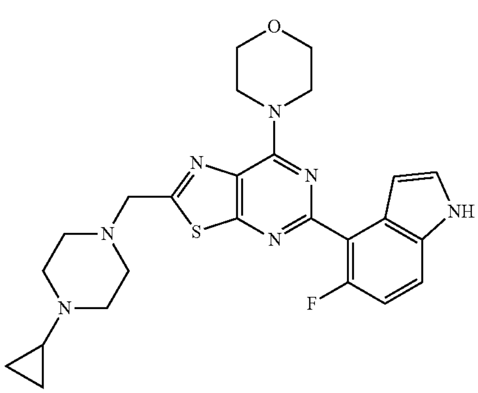 | 2-(4-Cyclopropylpiperazin-1-ylmethyl)-5-(5-fluoro-1H-indol-4-yl)-7-morpholin-4-ylthiazolo[5,4-d]pyrimidine |

TABLE 1-continued

| Compound No. | Structure | Name |
|---|---|---|
| 25 | 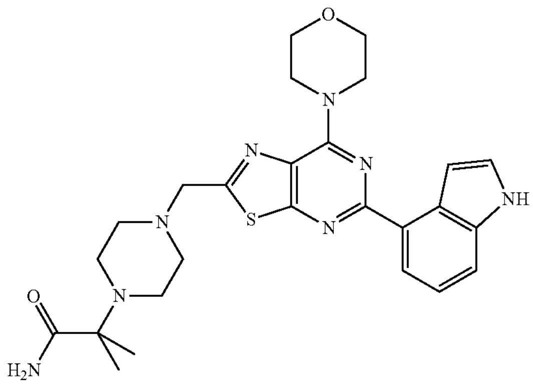 | 2-{4-[5-(1H-Indol-4-yl)-7-morpholin-4-ylthiazolo[5,4-d]pyrimidin-2-ylmethyl]piperazin-1-yl}isobutyramide |
| 26 | 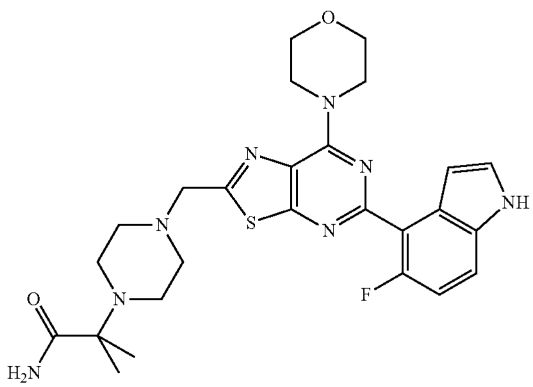 | 2-{4-[5-(5-Fluoro-1H-indol-4-yl)-7-morpholin-4-ylthiazolo[5,4-d]pyrimidin-2-ylmethyl]piperazin-1-yl}isobutyramide |
| 27 | 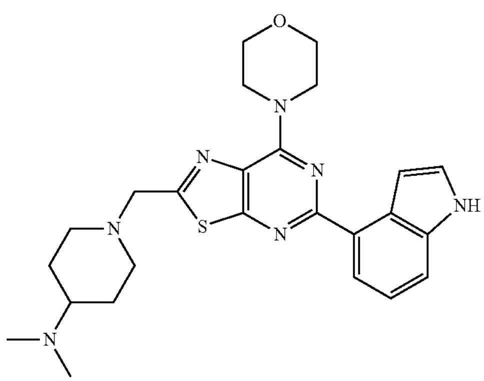 | {1-[5-(1H-Indol-4-yl)-7-morpholin-4-ylthiazolo[5,4-d]pyrimidin-2-ylmethyl]piperidin-4-yl}dimethylamine |
| 28 | 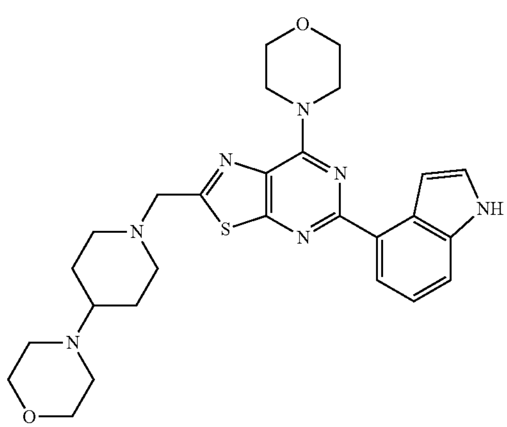 | 5-(1H-Indol-4-yl)-7-morpholin-4-yl-2-(4-morpholin-4-ylpiperidin-1-ylmethyl)thiazolo[5,4-d]pyrimidi |

TABLE 1-continued

| Compound No. | Structure | Name |
|---|---|---|
| 29 | 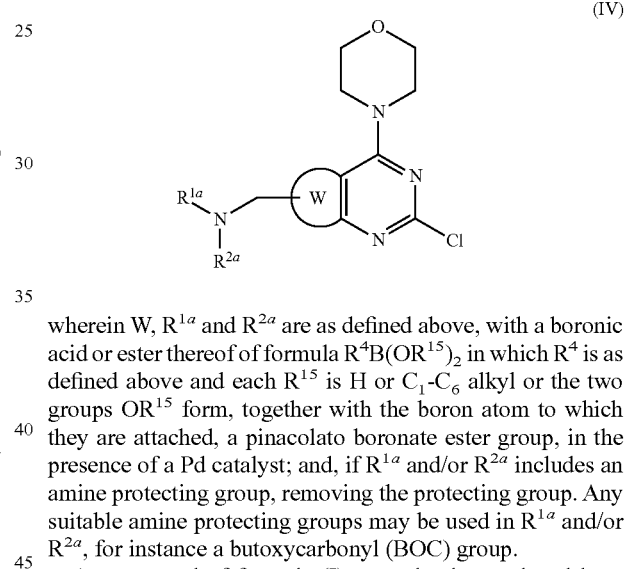 | 5-(5-Fluoro-1H-indol-4-yl)-7-morpholin-4-yl-2-(4-morpholin-4-ylpiperidin-1-ylmethyl)thiazolo[5,4-d]pyrimidine | and the pharmaceutically acceptable salts thereof.

A suitable synthetic strategy for producing a thiazolopyrimidine of formula (I) employs the precursor carboxaldehyde of formula (III):

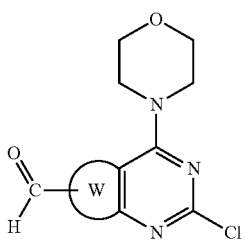

(III)

wherein W is as defined above. Starting from this precursor the synthesis comprises performing, in either order, a reductive amination and a palladium-mediated (Suzuki-type) cross-coupling reaction.

A compound of the invention may thus be produced by a process which comprises in treating a compound of formula (III):

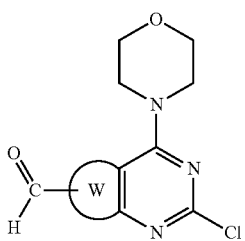

(III)

wherein W is as defined above, with an amine of formula NHR$^{1a}$R$^{2a}$ in which R$^{1a}$ and R$^{2a}$ are as defined above for R$^1$ and R$^2$ or R$^{1a}$ and R$^{2a}$ are as defined above for R$^1$ and R$^2$ wherein an N atom is present and is protected by an amine protecting group, in the presence of a suitable reducing agent; treating the resulting compound of formula (IV):

(IV)

wherein W, R$^{1a}$ and R$^{2a}$ are as defined above, with a boronic acid or ester thereof of formula R$^4$B(OR$^{15}$)$_2$ in which R$^4$ is as defined above and each R$^{15}$ is H or C$_1$-C$_6$ alkyl or the two groups OR$^{15}$ form, together with the boron atom to which they are attached, a pinacolato boronate ester group, in the presence of a Pd catalyst; and, if R$^{1a}$ and/or R$^{2a}$ includes an amine protecting group, removing the protecting group. Any suitable amine protecting groups may be used in R$^{1a}$ and/or R$^{2a}$, for instance a butoxycarbonyl (BOC) group.

A compound of formula (I) may also be produced by a process which comprises treating a compound of formula (III):

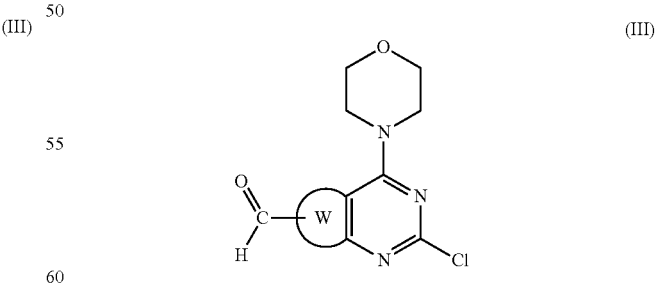

(III)

wherein W is as defined above, with a boronic acid or ester thereof of formula R$^4$B(OR$^{15}$)$_2$ in which R$^4$ is as defined above and each R$^{15}$ is H or C$_1$-C$_6$ alkyl, or the two groups OR$^{15}$ form, together with the boron atom to which they are attached, a pinacolato boronate ester group, in the presence of a Pd catalyst; treating the resulting compound of formula (V):

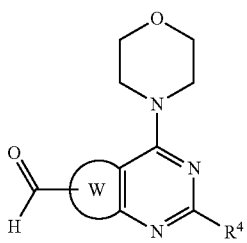

(V)

wherein W and $R^4$ are as defined above, with an amine of formula $NHR^{1a}R^{2a}$ in which $R^{1a}$ and $R^{2a}$ are as defined above, in the presence of a suitable reducing agent; and, if $R^{1a}$ and/or $R^{2a}$ includes an amine protecting group, removing the protecting group. In this embodiment of the process the N atom of the indole group $R^4$ may, if necessary, be protected before the compound of formula (V) is treated with the amine of formula $NHR^{1a}R^{2a}$, for instance as discussed further below and as shown in scheme 5 which follows. In that case the indole protecting group is removed in a subsequent step.

Both the reductive amination step and the Pd-mediated cross-coupling step take place under conventional conditions. The palladium catalyst may be any that is typically used for Suzuki-type cross-couplings, such as $PdCl_2(PPh_3)_2$. The reducing agent in the amination step is typically a borohydride, for instance $NaBH(OAc)_3$, $NaBH_4$ or $NaCNBH_3$, in particular $NaBH(OAc)_3$.

A compound of formula (III) as defined above may be produced by a process which comprises oxidizing a compound of formula (VI):

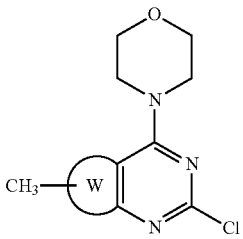

(VI)

wherein W is as defined above under suitable conditions. The oxidation may be performed, for instance, using $SeO_2$ in dioxane.

A compound of formula (III) as defined above may also be produced by a process which comprises treating a compound of formula (VII):

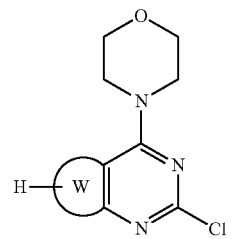

(VII)

wherein W is as defined above, with a deprotonating agent and then with dimethylformamide at −78° C. rising to room temperature. A suitable deprotonating agent is a lithiating agent, for instance an alkyllithium such as n-butyllithium in the presence of trimethylethylenediamine in THF at −78° C.

A compound of formula (VI) or (VII) as defined above may be produced by a process which comprises treating a compound of formula (VIII):

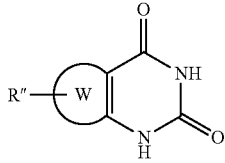

(VIII)

wherein W is as defined above and R" is H or $CH_3$ with a chlorinating agent followed by morpholine in a suitable solvent, for instance methanol at room temperature. A suitable chlorinating agent is $POCl_3$ in $PhNMe_2$. This reaction is suitably conducted at about 100° C.

A compound of formula (VIII) may be prepared by known methodologies or by analogy with known methodologies. For instance, included within formula (VIII) are compounds of the following formulae (VIIIa) and (VIIIb):

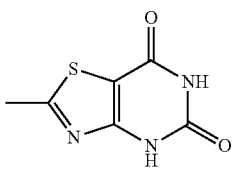

(VIIIa)

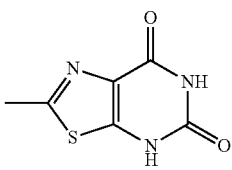

(VIIIb)

These may be prepared, respectively, as shown in schemes 1 and 2 which follow, where they feature as synthetic intermediates.

A further compound of formula (VIII) has the following formula (VIIIc):

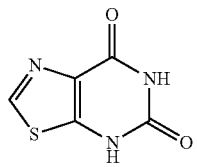

(VIIIc)

This compound may be prepared as described in the literature, for instance in M. Sekiya, Y. Osaki Chem. Pharm. Bull., 1965, 13, 1319-1325; S. J. Childress, R. L. McKee, J. Am. Chem. Soc., 1952, 73, 3862-3864; and U.S. Pat. No. 2,933, 498.

An alternative synthetic strategy for producing a thiazolopyrimidine of formula (I) entails attaching the group $R^4$ to the thiazolopyrimidine core by Suzuki coupling and then protecting the indole N atom of the group $R^4$, prior to introduction of the —CHO moiety which is submitted to reductive amination. The process comprises oxidising a compound of formula (IX):

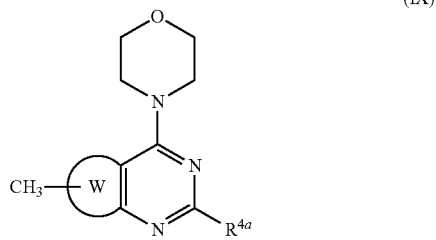

in which W is as defined above and $R^{4a}$ is a group $R^4$ as defined above in which the indole N atom is protected, under suitable conditions. The indole N atom is protected by any suitable protecting group, for instance a toluenesulphonyl group. The oxidation may be performed, for instance, using $SeO_2$ in dioxane. This reaction yields a compound of the following formula (X):

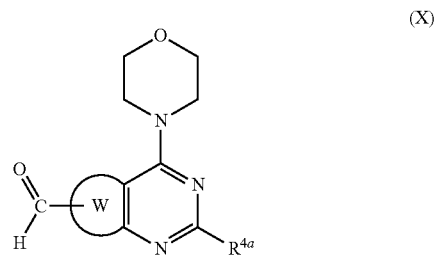

in which W and $R^{4a}$ are as defined above. The compound of formula (X) is then subjected to reductive amination by treatment with a compound $NHR^{1a}R^{2a}$ as defined above. Any protecting groups are removed subsequently. This strategy is illustrated in scheme 5 which follows.

Thiazolopyrimidines of formula (I) may be converted into pharmaceutically acceptable salts, and salts may be converted into the free compound, by conventional methods. Pharmaceutically acceptable salts include salts of inorganic acids such as hydrochloric acid, hydrobromic acid and sulfuric acid, and salts of organic acids such as acetic acid, oxalic acid, malic acid, methanesulfonic acid, trifluoroacetic acid, benzoic acid, citric acid and tartaric acid. In the case of compounds of the invention bearing a free carboxy substituent, the salts include both the above-mentioned acid addition salts and the salts of sodium, potassium, calcium and ammonium. The latter are prepared by treating the free thiazolopyrimidine of formula (I), or an acid addition salt thereof, with the corresponding metal base or ammonia.

Compounds of the present invention have been found in biological tests to be inhibitors of PI3 kinase. The compounds are selective for the p110δ isoform, which is a class Ia PI3 kinase, over other class Ia PI3 kinases. They are thus selective for the p110δ isoform over both the p110α isoform and the p110β isoform. In particular they are selective for p110δ over p110β. The compounds are also selective for the p110δ isoform over p110γ, which is a class Ib kinase.

The selectivity exhibited by compounds of the invention for p110δ (delta) over other isoforms of PI3 kinase is at least 2-fold. Typically the selectivity is 5-fold, or 10-fold, or 20-fold, or 50-fold, rising to 100-fold or higher in many cases.

Thus the compounds may be 2-fold, 5-fold, 10-fold, 20-fold, 50-fold or 100-fold selective for p110δ over p110β. They may also be 2-fold, 5-fold, 10-fold, 20-fold, 50-fold or 100-fold selective for p110δ over p110α or over p110γ.

A compound of the present invention may be used as an inhibitor of PI3 kinase, in particular of a class Ia PI3 kinase. Accordingly, a compound of the present invention can be used to treat a disease or disorder arising from abnormal cell growth, function or behaviour associated with PI3 kinase, in particular the p110δ isoform of PI3 kinase. Examples of such diseases and disorders are discussed by Drees et al in Expert Opin. Ther. Patents (2004) 14(5):703-732. These include proliferative disorders such as cancer, immune disorders, cardiovascular disease, viral infection, inflammation, metabolism/endocrine disorders and neurological disorders. Examples of metabolism/endocrine disorders include diabetes and obesity. Examples of cancers which the present compounds can be used to treat include leukaemia, brain tumours, renal cancer, gastric cancer and cancer of the skin, bladder, breast, uterus, lung, colon, prostate, ovary and pancreas.

A compound of the present invention may be used as an inhibitor of PI3 kinase. A human or animal patient suffering from a disease or disorder arising from abnormal cell growth, function or behaviour associated with PI3 kinase, in particular with the p110δ isoform of PI3 kinase such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A compound of the invention is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolize to glucose or which only metabolize a very small amount to glucose.

Such formulations may also contain a demulcent, a preservative and flavouring and coloring agents.

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables.

C) By inhalation, in the form of aerosols or solutions for nebulizers

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols.

E) Topically, in the form of creams, ointments, jellies, collyriums, solutions or suspensions.

The invention will be further described in the Examples which follow:

EXAMPLES

General Synthetic Procedure

The following general schemes 1 to 6 illustrate routes to compounds of formula (I). Schemes 7 and 8 illustrate routes to intermediates used in the synthesis of compounds of formula (I).

Scheme 1

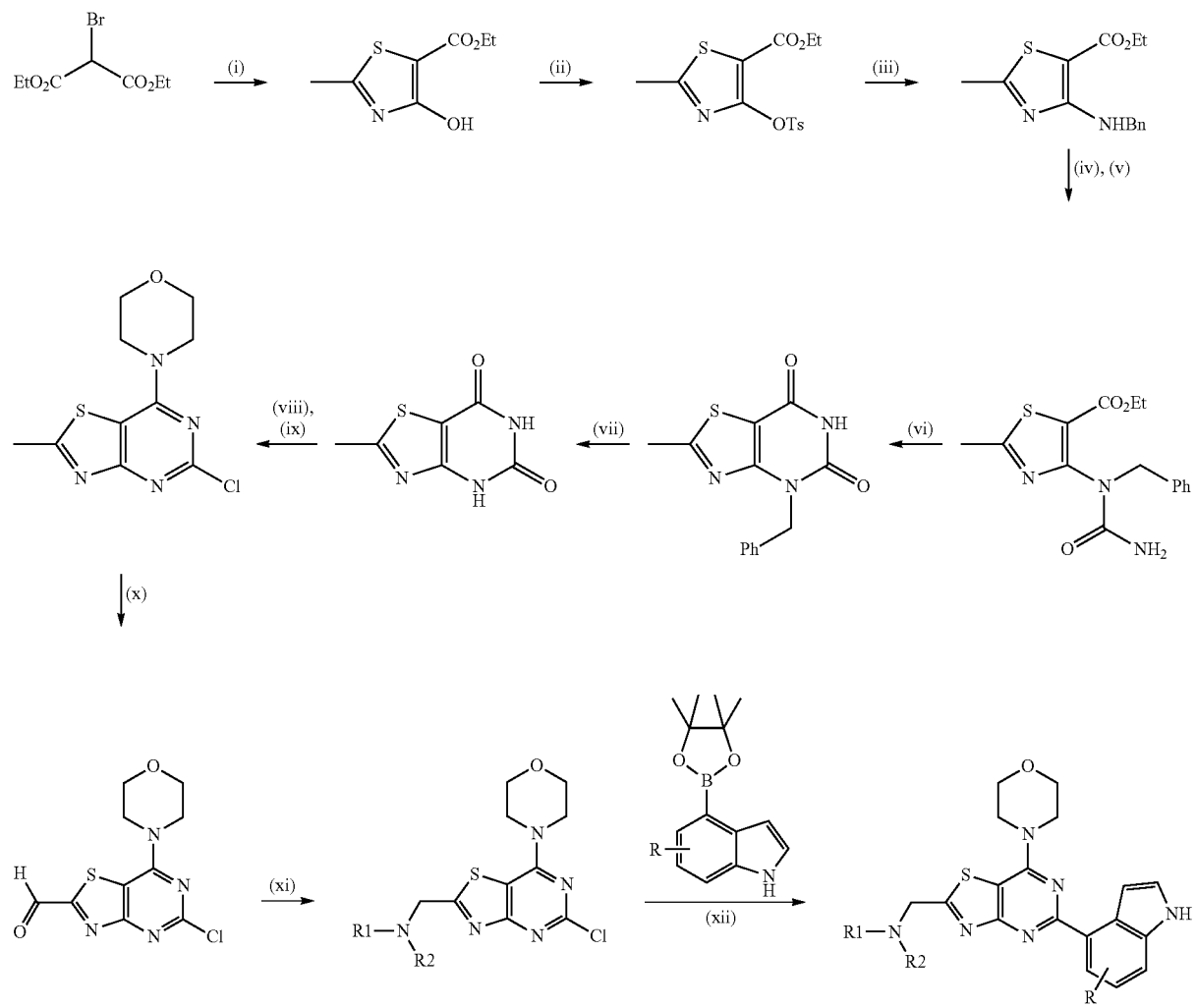

Conditions: (i) thioacetamide, toluene, 111° C. (ii) TsCl, Et₃N. (iii) BnNH₂, dioxane, 80° C. (iv) ClSO₂NCO, CH₂Cl₂, −78° C. (v) 6N HCl, 100° C. 2 h. (vi) NaOMe, MeOH, 67° C. (vii) BBr₃, xylene, 150° C. (viii) POCl₃, DMA, 150° C. (ix) morpholine, MeOH, RT. (x) SeO₂, dioxane, 80° C. (xi) R1R2NH, DCE, Na(AcO)₃BH, AcOH. (xii) Dioxane-water, Cs₂CO₃, Pd (PPh₃)₄, 120° C., microwave.

Scheme 1A

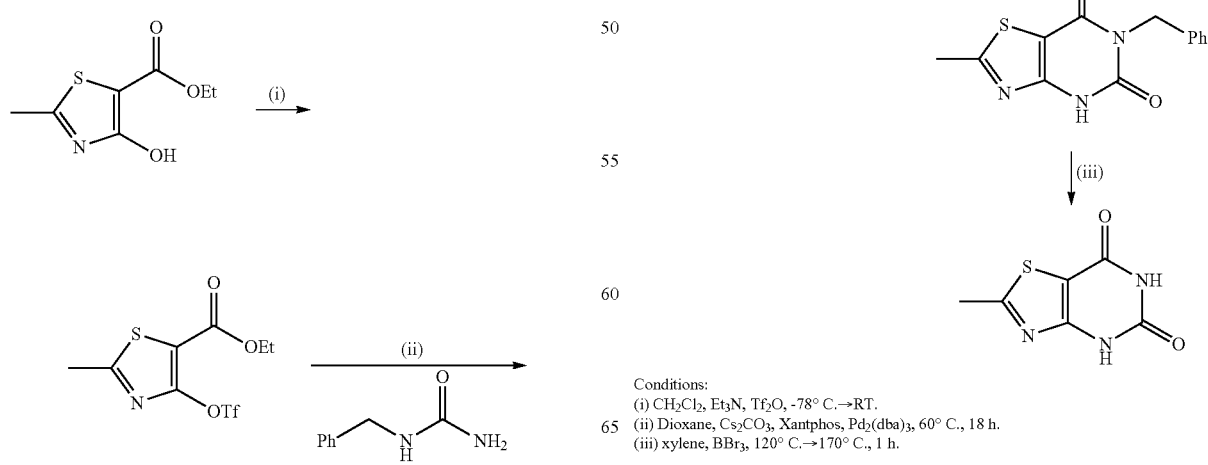

Conditions:
(i) CH₂Cl₂, Et₃N, Tf₂O, −78° C.→RT.
(ii) Dioxane, Cs₂CO₃, Xantphos, Pd₂(dba)₃, 60° C., 18 h.
(iii) xylene, BBr₃, 120° C.→170° C., 1 h.

Scheme 2
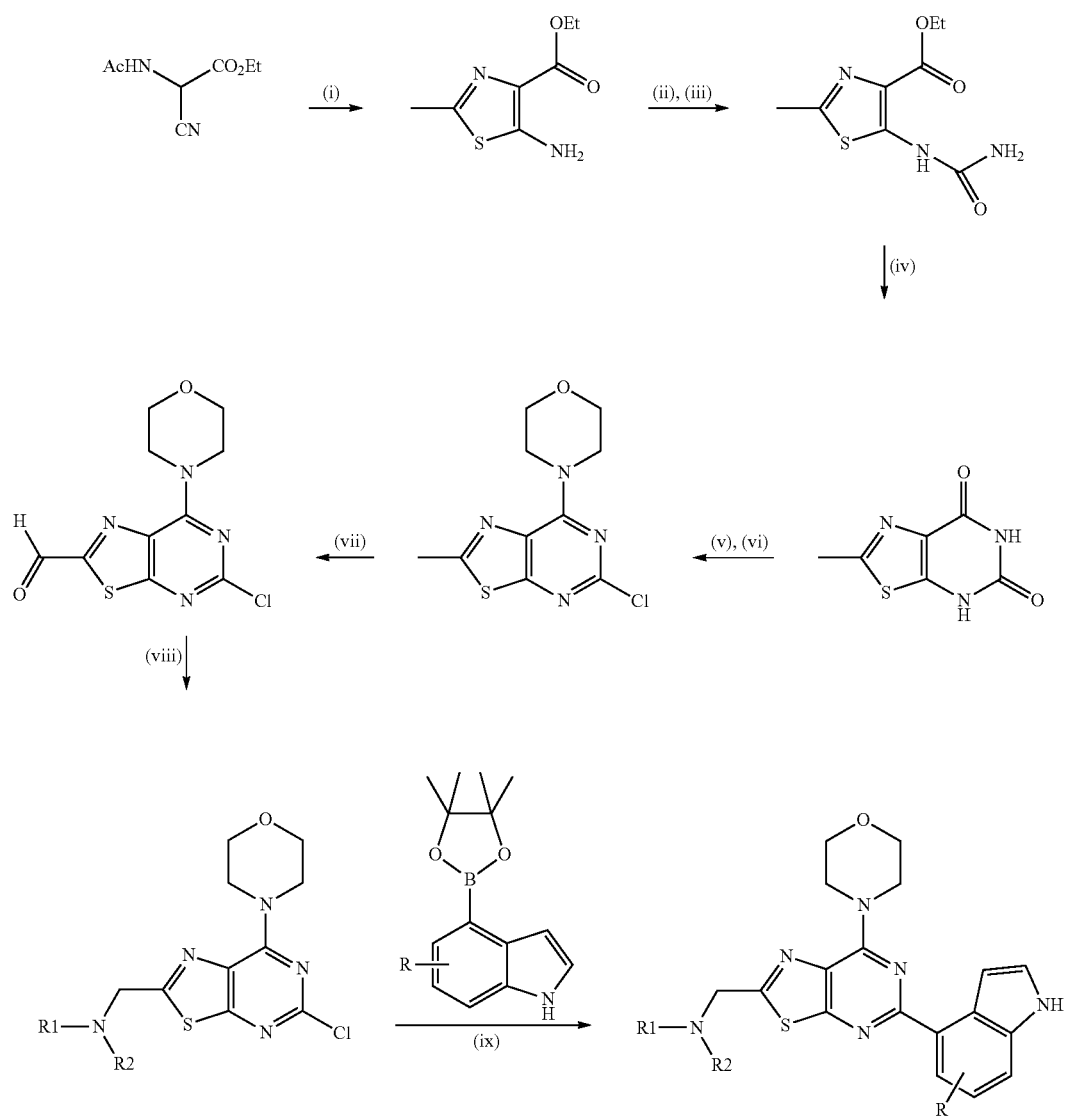
Conditions: (i) Lawesson's reagent, toluene, 111° C. (ii) ClSO₂NCO, CH₂Cl₂, -78° C. (iii) 6N HCl, 100° C. 2 h. (iv) 2N NaOH, iPrOH, 80° C. 2 h. (v) POCl₃, PhNMe₂, 100° C., 4 h. (vi) morpholine, MeOH, RT. (vii) oxidation (viii) R1R2NH, DCE, Na(AcO)₃BH, AcOH. (ix) Dioxane-water, Cs₂CO₃. Pd (PPh₃)₄, 120° C., microwave.
Scheme 3
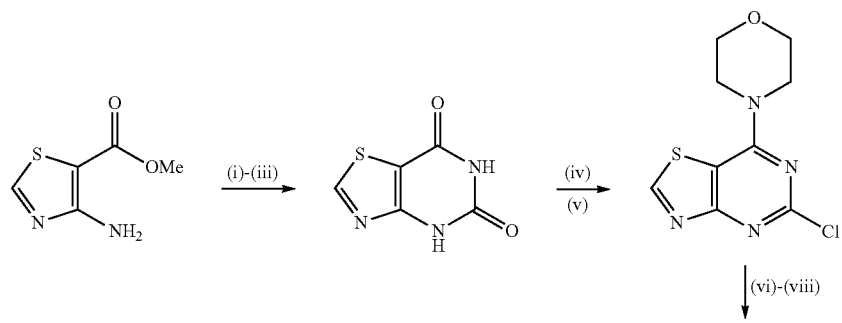

-continued

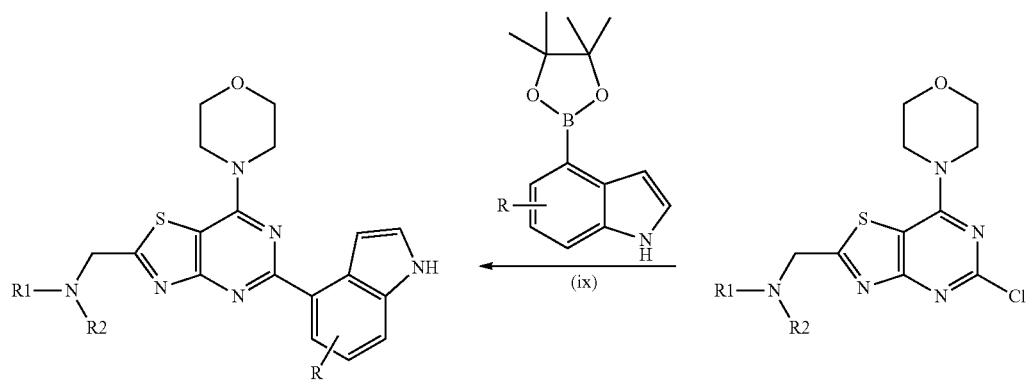

Conditions:
(i) ClSO₂NCO, CH₂Cl₂, -78° C..
(ii) 6N HCl, 100° C. 2 h.
(iii) 2N NaOH, MeOH, 100° C. 2 h.
(iv) POCl₃, 100° C..
(v) morpholine, MeOH, RT.
(vi) nBuLi, TMEDA, THF, -78° C..
(vii) DMF -78° C.→RT.
(viii) R1R2NH, DCE, Na(AcO)₃BH, AcOH.
(ix) CH₃CN—H₂O, Na₂CO₂, PdCl₂(PPh₃)₂, microwave, 120° C..

Scheme 4

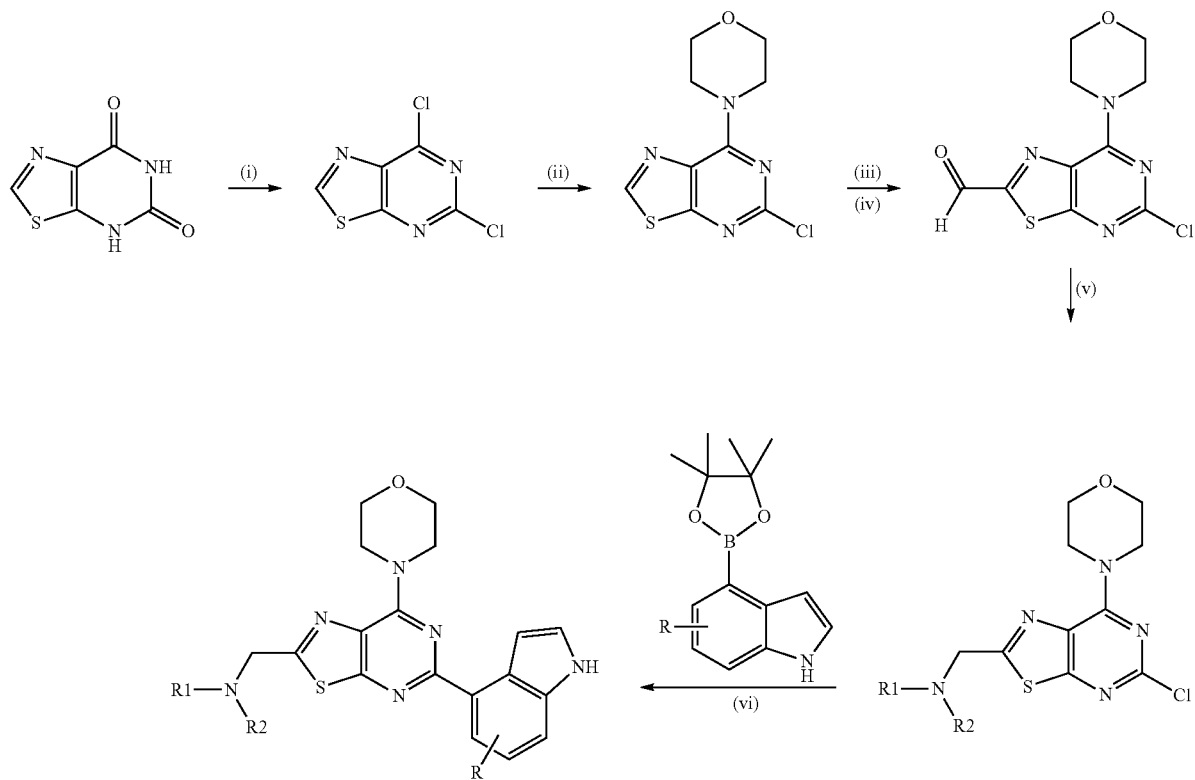

Conditions: (i) POCl₃, 80° C. (ii) morpholine, MeOH, RT. (iii) nBuLi, TMEDA, THF, -78° C. (iv) DMF -78° C. → RT. (v) R1R2NH, DCE, Na(AcO)₃BH, AcOH.
(vi) CH₃CN—H₂O, Na₂CO₃, PdCl₂(PPh₃)₂, microwave, 120° C.

Scheme 5

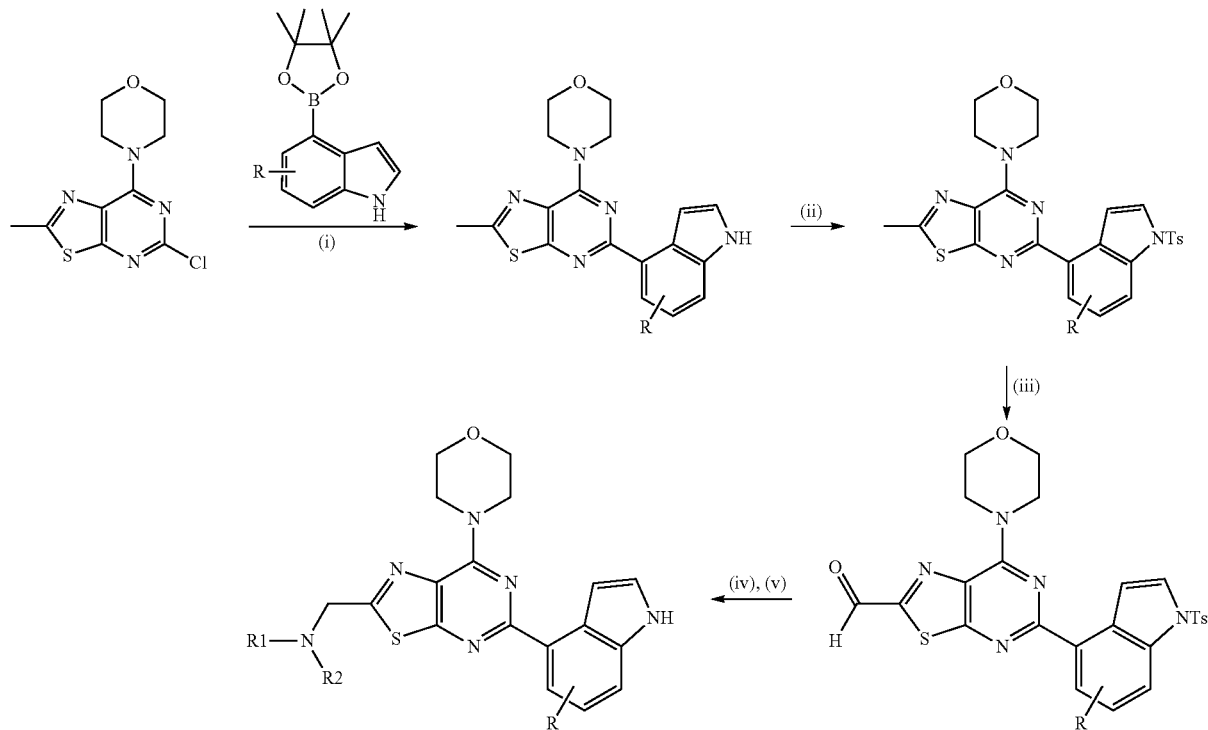

Conditions: (i) dioxane-H$_2$O, Cs$_2$CO$_3$, Pd(PPh$_3$)$_4$, microwave, 120° C. (ii) THF, NaH, TsCl. (iii) SeO$_2$, dioxane, 100° C. (iv) R1R2NH, DCE, Na(AcO)$_3$BH, AcOH. (v) Dioxane-IMS, NaOH, H$_2$O, RT.

Scheme 6

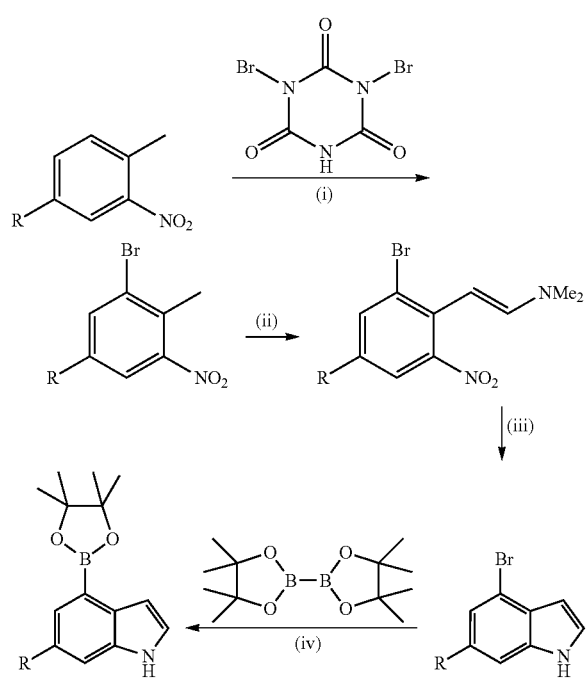

Conditions: (i) H$_2$SO$_4$, 21 h. (ii) Dioxane, DMF—DMA, 80° C. 24 h, 90° 16 h. (iii) MeOH—THF Raney® Nickel, NH$_2$NH$_2$·H$_2$O, RT, 40 min. (iv) DMSO, KOAc, Pd(dppf)$_2$Cl$_2$, 80° C.

Scheme 7

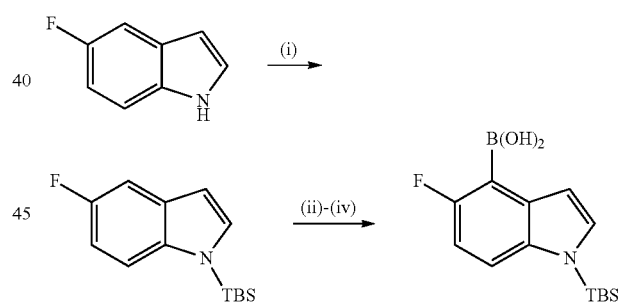

Conditions:
(i) THF, NaH 0° C. then TBSCl, RT, 25 h, 74%.
(ii) sBuLi, TMEDA, THF, -78° C., 2 h.
(iii) B(OiPr)$_3$, THF, -78° C.→-10° C., 15 min.
(iv) 2.4M HCl (71%, 3 steps).

Scheme 8

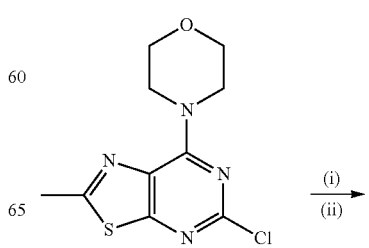

Scheme 11

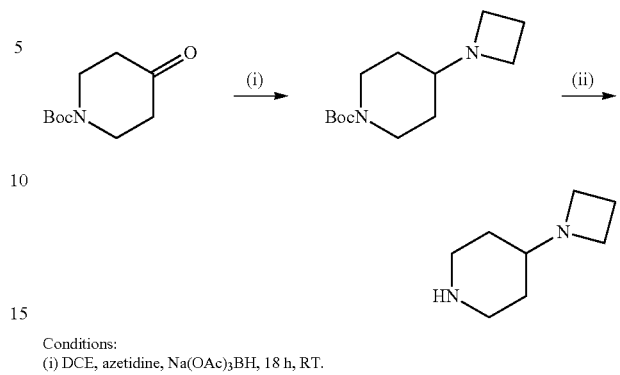

Conditions:
(i) DCE, azetidine, Na(OAc)₃BH, 18 h, RT.
(ii) TFA—CH₂Cl₂.

General Experimental Details:

NMR Spectroscopy

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Purification by Column Chromatography

Compounds purified by column chromatography were purified using silica gel or Isolute® cartridge or Redisep® cartridge, eluting with gradients from 100-0 to 0-100% of cyclohexane/EtOAc, or from 100-0 to 0-100% pentane/EtOAc or from 100-0 to 70-30% DCM/MeOH (with or without the addition of NH₃ 0.1%). 'Silica gel' refers to silica gel for chromatography, 0.035 to 0.070 mm (220 to 440 mesh) (e.g. Fluka silica gel 60), and an applied pressure of nitrogen up to 10 p.s.i accelerated column elution. Where thin layer chromatography (TLC) has been used, it refers to silica gel TLC using plates, typically 3×6 cm silica gel on aluminium foil plates with a fluorescent indicator (254 nm), (e.g. Fluka 60778).

Purification by Preparative HPLC:

Compounds purified by preparative HPLC were purified using a C18-reverse-phase column (100×22.5 mm i.d Genesis column with 7 μm particle size, UV detection at 230 or 254 nm, flow 5-15 mL/min), or a Phenyl-Hexyl column (250× 21.2 mm i.d. Gemini column with 5 μm particle size, UV detection at 230 or 254 nm, flow 5-20 mL/min), eluting with gradients from 100-0% to 0-100% water/acetonitrile or water/MeOH containing 0.1% TFA or water/acetonitrile containing 0.1% formic acid. The free base was liberated by partitioning between EtOAc and a sat. solution of sodium bicarbonate. The organic layer was dried (MgSO₄) and concentrated in vacuo. Alternatively, the free base was liberated by passing through an Isolute® SCX-2 cartridge, eluting with NH₃ in methanol.

Microwave Reactions:

Microwave experiments were carried out using either a Personal Chemistry Smith Synthesiser or a Biotage Initiator™, which uses a single-mode resonator and dynamic field

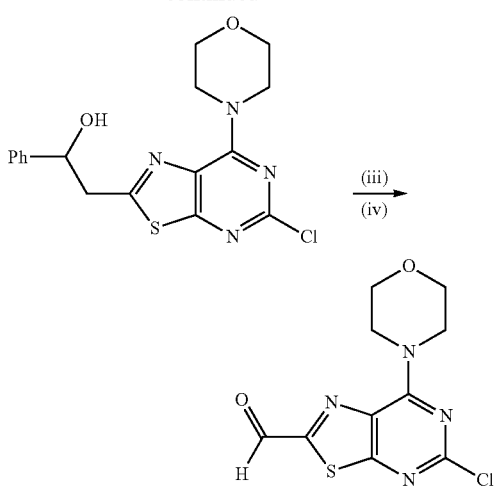

Conditions: (i) THF, TMEDA, nBuLi, -78° C., 15 min. (ii) PhCHO, -78° C.→RT (66%; 2 steps). (iii) toluene, pTsOH, 120° C., 24 h. (iv) THF, CH₃CN, H₂O, RuCl₃, H₅IO₆, RT 2 h (42%; 2 steps).

Scheme 9

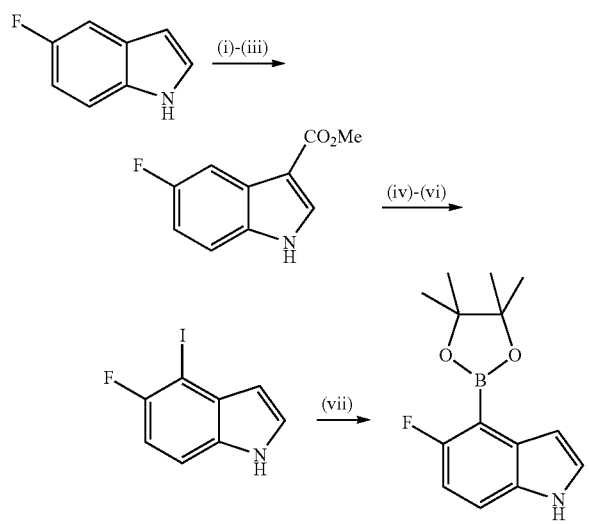

Conditions: (i) DMF, TFAA, 0° C. (ii) 10% aq NaOH, 100° C., 1 h. (iii) MeOH, H₂SO₄, 65° C., 18 h. (iv) Tl(OCOCF₃)₃, TFA, RT, 2 h. (v) H₂O, KI, RT. (vi) MeOH, 40% aq NaOH, 65° C., 2 h. (vii) pinacol borane, Et₃N, Dioxane, Pd(OAc)₂, bis(cyclohexyl)phosphino-2-biphenyl, 80° C., 30 min.

Scheme 10

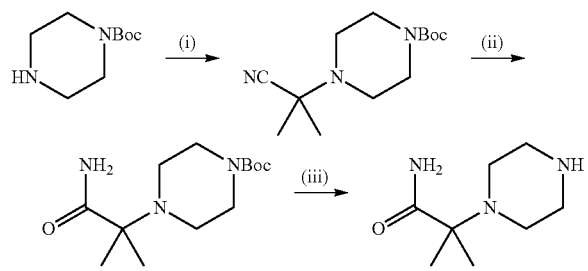

Conditions: (i) NaCN, acetone-H₂O, 48 h, RT. (ii) DMSO, K₂CO₃, H₂O₂, 40° C. (iii) HCl Et₂O.

tuning, both of which give reproducibility and control. Temperatures from 40-250° C. can be achieved and pressures of up to 20 bar can be reached.

All solvents and commercial reagents were used as received. Non-commercially available reagents/reactants were prepared according to procedures described in the literature.

Abbreviations used in the experimental section:

| | |
|---|---|
| aq. = | aqueous |
| BOC = | t-Butoxycarbonyl |
| bs = | broad singlet (NMR) |
| $Cs_2CO_3$ = | cesium carbonate |
| d = | doublet (NMR) |
| DCM = | dichloromethane |
| DIPEA = | diisopropylethylamine |
| DMA = | dimethylacetamide |
| DMAP = | dimethylaminopyridine |
| DMF = | dimethylformamide |
| DMSO = | dimethylsulfoxide |
| eq. = | equivalents |
| EtOAc = | ethyl acetate |
| EtOH = | ethanol |
| h = | hour(s) |
| HATU = | O-(7-Azabenzotriazol-1-yl)-N,N,N',N'-tetramethyluronium hexafluorophosphate |
| HCl = | hydrochloric acid |
| $H_2O$ = | water |
| HPLC = | high pressure liquid chromatography |
| IMS = | industrial methylated spirit |
| iPrOH = | isopropanol |
| LCMS = | liquid chromatography mass spectrometry |
| M = | molar |
| m = | multiplet (NMR) |
| MeOH = | methanol |
| mg = | milligram |
| $MgSO_4$ = | magnesium sulphate |
| min = | minute(s) |
| mL = | milliliter |
| $Na_2CO_3$ = | sodium carbonate |
| $NaHCO_3$ = | sodium hydrogen carbonate |
| NaOH = | sodium hydroxide |
| $Na_2SO_4$ = | sodium sulfate |
| NMR = | nuclear magnetic resonance |
| q = | quartet (NMR) |
| Rt = | retention time |
| RT = | room temperature |
| sat = | saturated |
| t = | triplet (NMR) |
| TBAF = | tetrabutylammonium fluoride |
| TBS = | t-butyldimethylsilyl |
| TFA = | trifluoroacetic acid |
| THF = | tetrahydrofuran |
| TLC = | thin layer chromatography |
| Xant phos = | 4,5-bis(diphenylphosphino)-9,9-dimethylxanthene |

Reference Example 1

Formation of Boronate Ester

The boronate ester product of the final step of schemes 1 to 4 above was prepared as follows. To a solution of halide (1 eq.) and bis(pinacolato)diboron (1.3 eq.) in DMSO were added KOAc (3 eq.) and [1,1'-bis(diphenylphosphine)ferrocene]-dichloropalladium (0.05 eq.). The mixture was heated at 90° C. until completion of the reaction. The reaction mixture was partioned between EtOAc and $H_2O$. The organic layer was washed successively with $H_2O$ and brine, dried over $Na_2SO_4$ and evaporated to dryness. The resultant residue was then purified by column chromatography.

Reference Example 2

Suzuki Coupling

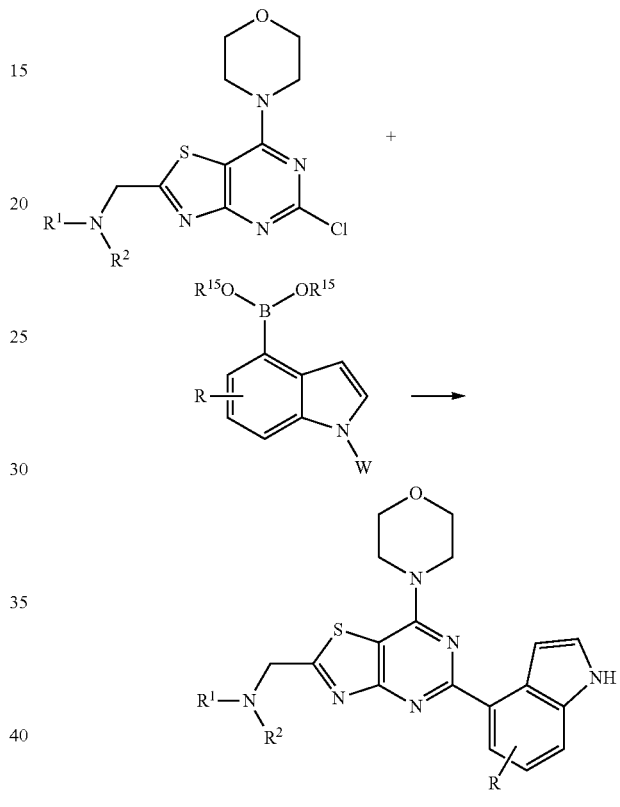

W = H, or protecting group, e.g. TBS

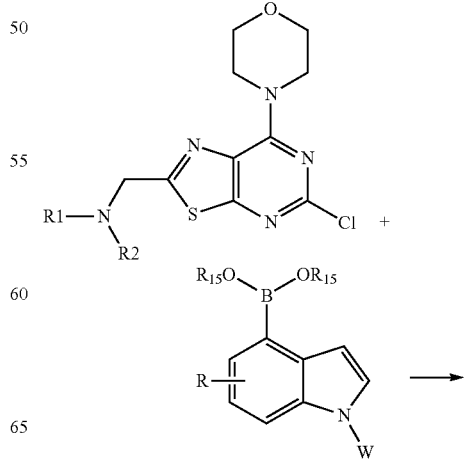

-continued

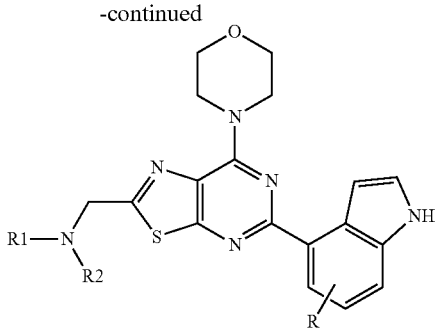

W = H, or protecting group, e.g. TBS

The following methods were used for the Suzuki coupling reactions depicted in schemes A and B above:

Method A

A mixture of the appropriate 5-chlorothiazolopyrimidine (1 eq.), Na$_2$CO$_3$ (2 eq.), the appropriate indole boronate ester (1.5 eq.) and bis(triphenylphosphine)palladium (II) chloride (0.1 eq.) in acetonitrile/water (2:1) was heated at 140° C. for 20-50 min in a microwave reactor. The resulting mixture was diluted with water then extracted with ethyl acetate. The combined organic extracts were dried (Na$_2$SO$_4$), filtered and concentrated in vacuo then purified by either preparative HPLC or column chromatography to give the desired product. Alternatively, the reaction mixture was loaded onto an Isolute® SCX-2 cartridge, washed with MeOH then eluted with 2 M NH$_3$ in MeOH. The resulting residue was then purified by either preparative HPLC or column chromatography to give the desired product.

Method B

A mixture of the appropriate 5-chlorothiazolopyrimidine (1 eq.), Cs$_2$CO$_3$ (1.5 eq.), the appropriate indole boronate ester or boronic acid (1.2 eq.) and tetrakis(triphenylphosphine)palladium (0.05 eq.) in dioxane/water (3:1) was heated at 125° C., for 10-30 min in a microwave reactor. The resulting mixture was diluted with water then extracted with ethyl acetate. The combined organic extracts were dried (MgSO$_4$), filtered and concentrated in vacuo then purified by either preparative HPLC or column chromatography to give the desired product. Alternatively, the reaction mixture was loaded onto an Isolute® SCX-2 cartridge, washed with MeOH then eluted with 2 M NH$_3$ in MeOH. The resulting residue was then purified by either preparative HPLC or column chromatography to give the desired product.

Method C

A mixture of the appropriate 5-chlorothiazolopyrimidine (1 eq.), Cs$_2$CO$_3$ (1.5 eq.), the appropriate indole boronic acid (1.2 eq.) and tetrakis(triphenylphosphine)palladium (0.05 eq.) in dioxane/water (3:1) was heated at 125° C., for 10-30 min in a microwave reactor. The resulting mixture was diluted with water then extracted with ethyl acetate. The combined organic extracts were dried (MgSO$_4$), filtered and concentrated in vacuo then purified by either preparative HPLC or column chromatography to give the desired product. Alternatively, the reaction mixture was loaded onto an Isolute® SCX-2 cartridge, washed with MeOH then eluted with 2 M NH$_3$ in MeOH. The resulting residue was then purified by either preparative HPLC or column chromatography to give the desired product.

Method D

A mixture of the appropriate 5-chlorothiazolopyrimidine (1 eq.), Cs$_2$CO$_3$ (1.5 eq.), the appropriate indole boronic acid (1.2 eq.) and tetrakis(triphenylphosphine)palladium (0.05 eq.) in acetonitrile/water (3:1) was heated at 125° C.-140° C., for 10-30 min in a microwave reactor. The resulting mixture was diluted with water then extracted with ethyl acetate. The combined organic extracts were dried (MgSO$_4$), filtered and concentrated in vacuo then purified by either preparative HPLC or column chromatography to give the desired product. Alternatively, the reaction mixture was loaded onto an Isolute® SCX-2 cartridge, washed with MeOH then eluted with 2 M NH$_3$ in MeOH. The resulting residue was then purified by either preparative HPLC or column chromatography to give the desired product.

Method E

A mixture of the appropriate 5-chloro-thiazolopyrimidine (1 eq.), Cs$_2$CO$_3$ (1.5 eq.), the appropriate indole boronate ester (1.2 eq.) and tetrakis(triphenylphosphine)palladium (0.05 eq.) in acetonitrile/water (3:1) was heated at 140° C., for 10-30 min in a microwave reactor. The resulting mixture was diluted with water then extracted with ethyl acetate. The combined organic extracts were dried (MgSO$_4$), filtered and concentrated in vacuo then purified by either preparative HPLC or column chromatography to give the desired product. Alternatively, the reaction mixture was loaded onto an Isolute® SCX-2 cartridge, washed with MeOH then eluted with 2 M NH$_3$ in MeOH. The resulting residue was then purified by either preparative HPLC or column chromatography to give the desired product.

Method F

A mixture of the appropriate 5-chloro-thiazolopyrimidine (1 eq.), Na$_2$CO$_3$ (1.5 eq.), the appropriate indole boronate ester (1.2 eq.) and tetrakis(triphenylphosphine)palladium (0.1 eq.) in acetonitrile/water (2:1) was heated at 140° C., for 10-30 min in a microwave reactor. The resulting mixture was diluted with water then extracted with ethyl acetate. The combined organic extracts were dried (MgSO$_4$), filtered and concentrated in vacuo then purified by either preparative HPLC or column chromatography to give the desired product. Alternatively, the reaction mixture was loaded onto an Isolute® SCX-2 cartridge, washed with MeOH then eluted with 2 M NH$_3$ in MeOH. The resulting residue was then purified by either preparative HPLC or column chromatography to give the desired product.

Method G

A mixture of the appropriate 5-chloro-thiazolopyrimidine (1 eq.), Na$_2$CO$_3$ (1.5 eq.), the appropriate indole boronic acid (1.2 eq.) and tetrakis(triphenylphosphine)palladium (0.1 eq.) in acetonitrile/water (2:1) was heated at 140° C., for 10-30 min in a microwave reactor. The resulting mixture was diluted with water then extracted with ethyl acetate. The combined organic extracts were dried (MgSO$_4$), filtered and concentrated in vacuo then purified by either preparative HPLC or column chromatography to give the desired product. Alternatively, the reaction mixture was loaded onto an Isolute® SCX-2 cartridge, washed with MeOH then eluted with 2 M NH$_3$ in MeOH. The resulting residue was then purified by either preparative HPLC or column chromatography to give the desired product Reference Example 3 t-Butoxycarbonyl Deprotection

To a solution of the relevant BOC-protected thiazolopyrimidine in DCM was added TFA and the resulting solution was stirred at RT for 30-180 min. The resulting mixture was diluted with water, neutralised with saturated aqueous solution of NaHCO$_3$ then extracted with DCM. The combined organic extracts were dried (MgSO$_4$ or Na$_2$SO$_4$), filtered and concentrated in vacuo, then purified by either preparative HPLC or column chromatography to give the desired product. Alternatively, the reaction mixture was loaded onto an Isolute® SCX-2 cartridge, washed with MeOH then eluted with 2 M NH₃ in MeOH. The resulting residue was then purified by either preparative HPLC or column chromatography to give the desired product.

Reference Example 4

TBS-Deprotection

To a solution of the relevant TBS-protected 1H-indol-4-yl-thiazolopyrimidine in THF was added TBAF and the resulting solution was stirred at RT for 30 min, then concentrated in vacuo. Alternatively, the resulting solution was diluted with brine then extracted with DCM. The combined organic extracts were dried (MgSO₄ or Na₂SO₄), filtered and concentrated in vacuo. In either case, the resultant residue was purified by either preparative HPLC or column chromatography to give the desired product.

Reference Example 5

5-Amino-2-methyl-thiazole-4-carboxylic acid ethyl ester

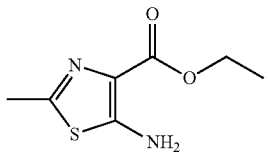

To a solution of acetylamino-cyano-acetic acid ethyl ester (27.2 g, 0.160 mol) in anhydrous toluene (300 mL) was added Lawesson's reagent (32.0 g, 0.079 mol) and the resulting mixture heated at reflux for 18 h. The resulting yellow suspension was partitioned between an aqueous solution of HCl (1 M) and tert-butyl methyl ether. The layers were separated and the organic layer extracted with an aqueous solution of HCl (1 M). The combined aqueous layers was basified to pH 10 with an aqueous solution of NaOH (2 M), then extracted with EtOAc. The organic layer was isolated, dried (Na₂SO₄) and concentrated in vacuo to give the title compound as a pale yellow solid (17.0 g, 57%).

[M+H]⁺ 187.0

Reference Example 6

2-Methyl-5-ureido-thiazole-4-carboxylic acid ethyl ester

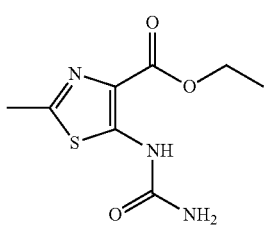

To a solution of 5-amino-2-methyl-thiazole-4-carboxylic acid ethyl ester (15.0 g, 0.081 mol) in DCM (550 mL) was added chlorosulfonyl isocyanate (8.92 mL, 0.102 mol) dropwise at −78° C. The thick suspension was allowed to warm to RT and stirred for 45 minutes. The resulting precipitate was collected by filtration and dried in vacuo. The resultant white solid was suspended in an aqueous solution of HCl (6 M, 400 mL) and heated at 90° C. for 1 h. The resulting solution was cooled to 0° C. and pH adjusted to 5 with an aqueous solution of NaOH (6 M). The resultant precipitate was collected by filtration and dried in vacuo at 60° C. for 36 h to give the title compound (16.4 g, 89%).

[M+H]⁺ 230.0

Reference Example 7

2-Methyl-4H-thiazolo[5,4-d]pyrimidine-5,7-dione

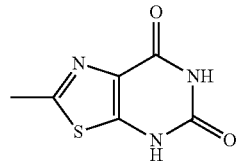

To a suspension of 2-methyl-5-ureido-thiazole-4-carboxylic acid ethyl ester (21.0 g, 0.079 mol) in iPrOH (300 mL) was added an aqueous solution of NaOH (3 M, 26 mL, 0.078 mol) at 80° C. The thick white suspension was heated at 80° C. for 45 min, then diluted with H₂O and cooled to 0° C. The reaction mixture was acidified to pH 3 and the precipitate collected by filtration. The white solid was washed with H₂O and dried in vacuo at 60° C. for 17 h to give the title compound as a white solid (12.3 g, 83%).

$^{1}$H NMR (300 MHz, DMSO-$d_6$): δ 2.56 (s, 3H).

Reference Example 8

5,7-Dichloro-2-methyl-thiazolo[5,4-d]pyrimidine

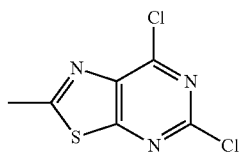

To a mixture of 2-methyl-4H-thiazolo[5,4-d]pyrimidine-5,7-dione (7.5 g, 0.041 mol) in N,N-dimethylaniline (3.7 mL, 0.029 mol) was added phosphorous oxychloride (38.0 mL, 0.410 mol) and the mixture heated at 130° C. for 4 h. The resulting black solution was cooled to RT, then carefully quenched with crushed ice and H₂O, before being extracted with EtOAc. The organic layer was isolated, dried (MgSO₄) and concentrated in vacuo to give a yellow solid. The solid was dissolved in DCM, then washed with an aqueous solution of NaHCO₃ followed by brine, dried (Na₂SO₄) and concentrated in vacuo to give the title compound as a pale yellow solid (4.90 g, 54%).

$^{1}$H NMR (300 MHz, CDCl₃): δ 2.95 (s, 3H).

Reference Example 9

5-Chloro-2-methyl-7-morpholin-4-yl-thiazolo[5,4-d]pyrimidine

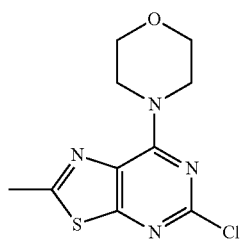

To a solution of 5,7-dichloro-2-methyl-thiazolo[5,4-d]pyrimidine (4.1 g, 18.72 mmol) in MeOH (100 mL) was added morpholine (3.26 mL, 37.44 mmol) at 0° C. and the mixture stirred at 0° C. for 30 minutes. The resultant precipitate was collected by filtration and dried in vacuo at 40° C. to give the title compound as a cream solid (4.42 g, 89%).

$^1$H NMR (300 MHz, CDCl$_3$): δ 2.74 (s, 3H), 3.80-3.86 (m, 4H) and 4.35 (m, 4H).

Reference Example 10

5-(1H-Indol-4-yl)-2-methyl-7-morpholin-4-yl-thiazolo[5,4-d]pyrimidine

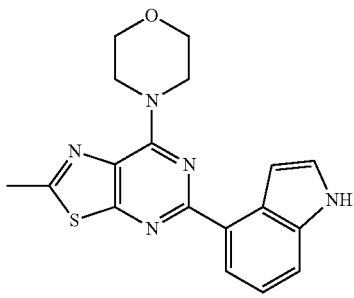

Prepared via the Suzuki coupling method of Reference Example 2, using 5-Chloro-2-methyl-7-morpholin-4-yl-thiazolo[5,4-d]pyrimidine. The title compound was obtained as a white solid (130 mg, 50%).

[M+H]$^+$ 352.9

Reference Example 11

4-Hydroxy-2-methyl-thiazole-5-carboxylic acid ethyl ester

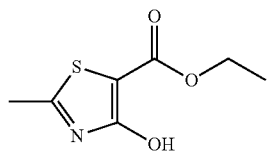

To a solution of thioacetamide (17.2 g, 0.229 mol) in toluene (130 mL) was added diethyl bromomalonate (55.0 g, 0.230 mol) and the mixture heated at reflux for 3 h. The reaction mixture was cooled to RT, filtered through Celite, then concentrated in vacuo. The resultant solid was triturated with hexane to give the title compound as a yellow solid (11.0 g, 26%).

$^1$H NMR (400 MHz, CDCl$_3$): δ 1.36 (t, J=7.1 Hz, 3H), 2.67 (s, 3H) and 4.35 (q, J=7.1 Hz, 2H).

Reference Example 12

2-Methyl-4-(toluene-4-sulfonyloxy)-thiazole-5-carboxylic acid ethyl ester

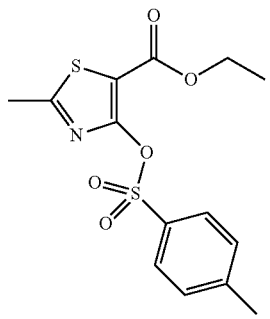

To a solution of 4-hydroxy-2-methyl-thiazole-5-carboxylic acid ethyl ester (5.0 g, 26.74 mmol) in chloroform (80 mL) were added p-toluenesulfonyl chloride (5.61 g, 29.41 mmol) and triethylamine (4.84 mL, 34.76 mmol) at 0° C. The reaction mixture was allowed to warm to RT over 4 h, then diluted with DCM and H$_2$O. The organic layer was isolated, washed with H$_2$O and brine, then dried (MgSO$_4$) and concentrated in vacuo. The resultant residue was purified by column chromatography to give the title compound as a pale brown solid (8.1 g, 89%).

$^1$H NMR (400 MHz, CDCl$_3$): δ 1.34 (t, J=7.1 Hz, 3H), 2.47 (s, 3H), 2.64 (s, 3H), 4.30 (q, J=7.1 Hz, 2H), 7.37 (d, J=8.1 Hz, 2H) and 7.94 (d, J=8.1 Hz, 2H).

Reference Example 13

4-Benzylamino-2-methyl-thiazole-5-carboxylic acid ethyl ester

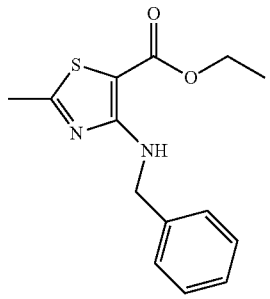

To a solution of 2-methyl-4-(toluene-4-sulfonyloxy)-thiazole-5-carboxylic acid ethyl ester (2.0 g, 5.865 mmol) in 1,4-dioxane (50 mL) was added benzylamine (1.92 mL, 17.6 mmol) and the mixture was heated at 120° C. for 6 h. The reaction mixture was cooled to RT and partitioned between EtOAc and an aqueous solution of HCl (1 M). The organic layer was isolated, washed with brine, then dried (MgSO$_4$) and concentrated in vacuo. The resultant residue was purified by column chromatography to give the title compound as a yellow solid (0.80 g, 49%).

$^1$H NMR (300 MHz, CDCl$_3$): δ 1.31 (t, J=7.1 Hz, 3H), 2.60 (s, 3H), 4.24 (q, J=7.1 Hz, 2H), 4.76 (d, J=6.1 Hz, 2H), 7.07 (bs, 1H) and 7.21-7.38 (m, 5H).

Reference Example 14

4-Benzyl-2-methyl-4H-thiazolo[4,5-d]pyrimidine-5,7-dione

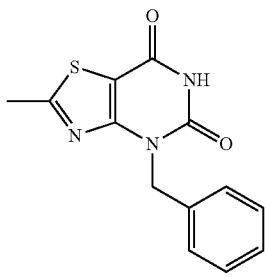

To a solution of 4-benzylamino-2-methyl-thiazole-5-carboxylic acid ethyl ester (0.40 g, 1.45 mmol) in DCM (10 mL) was added chlorosulfonyl isocyanate (140 μL, 1.59 mmol) dropwise at −78° C. The mixture was allowed to warm to RT and stirred for 30 minutes. The resulting solution was concentrated in vacuo then dissolved in acetone (5 mL), before H$_2$O (2 mL) was added dropwise. The mixture was stirred at RT for 30 minutes, then concentrated in vacuo. The resultant oil was partitioned between EtOAc and H$_2$O. The organic layer was isolated, washed with brine, dried (MgSO$_4$) and concentrated in vacuo to give 4-(1-benzyl-ureido)-2-methyl-thiazole-5-carboxylic acid ethyl ester as a pale brown oil. To a solution of 4-(1-benzyl-ureido)-2-methyl-thiazole-5-carboxylic acid ethyl ester in MeOH (10 mL) was added a solution of sodium methoxide in MeOH (25% w/w, 1.33 mL, 5.80 mmol) and the mixture was stirred at RT for 18 h. The crude reaction mixture was concentrated in vacuo and partitioned between EtOAc and an aqueous solution of HCl (1 M). The organic layer was isolated, washed with brine, then dried (MgSO$_4$) and concentrated in vacuo. The resultant residue was triturated with EtOAc to give the title compound as a pale yellow solid (0.25 g, 63%).

$^1$H NMR (300 MHz, DMSO-d$_6$): δ 2.76 (s, 3H), 5.25 (s, 2H), 7.19-7.40 (m, 5H) and 11.71 (s, 1H).

Reference Example 15

2-Methyl-4H-thiazolo[4,5-d]pyrimidine-5,7-dione

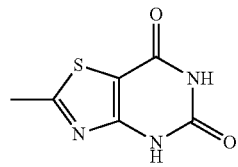

Method A

To a solution of 4-benzyl-2-methyl-4H-thiazolo[4,5-d]pyrimidine-5,7-dione (3.80 g, 13.87 mmol) in xylene (40 mL) was added boron tribromide (5.34 mL, 55.47 mmol) dropwise at 120° C. The reaction mixture was heated at 170° C. for 1 h, then cooled to 0° C., before MeOH (30 mL) was carefully added. The resultant precipitate was collected by filtration, washed with MeOH followed by H$_2$O, then dried in vacuo at 80° C. to give the title compound as a white solid (2.3 g, 91%).

$^1$H NMR (400 MHz, DMSO-d$_6$): δ 2.73 (s, 3H).

Method B

To a solution of 6-benzyl-2-methyl-4H-thiazolo[4,5-d]pyrimidine-5,7-dione (6 g, 22 mmol) in xylene (120 mL) was added boron tribromide (8.3 mL, 88 mmol) dropwise at 120° C. The reaction mixture was heated at 170° C. for 1 h, then cooled to 0° C., before MeOH (30 mL) was carefully added. The resultant precipitate was collected by filtration, washed with MeOH followed by H$_2$O, then dried in vacuo at 50° C. to give the title compound as a white solid (4.0 g, 100%).

$^1$H NMR (400 MHz, DMSO): δ 2.73 (s, 3H).

Reference Example 16

5,7-Dichloro-2-methyl-thiazolo[4,5-d]pyrimidine

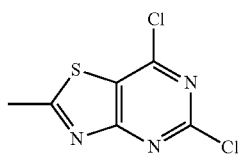

Prepared using the method used in the preparation of 5,7-dichloro-2-methyl-thiazolo[5,4-d]pyrimidine using 2-methyl-4H-thiazolo[4,5-d]pyrimidine-5,7-dione in place of 2-methyl-4H-thiazolo[5,4d]pyrimidine-5,7-dione. The title compound was obtained as an solid solid (140 mg, 28%).

$^1$H NMR (400 MHz, DMSO-d$_6$): δ 2.97 (s, 3H).

Reference Example 17

5-Chloro-2-methyl-7-morpholin-4-l-thiazolo[4,5-d]pyrimidine

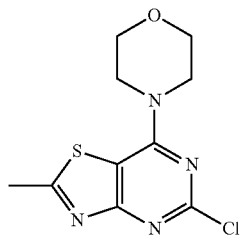

To a solution of 5,7-dichloro-2-methyl-thiazolo[4,5-d]pyrimidine (92 mg, 0.42 mmol) in MeOH (3 mL) was added morpholine (81 μL, 0.93 mmol) and the mixture stirred at RT for 1 h. The reaction mixture was diluted with EtOAc and H$_2$O. The organic layer was isolated, washed with brine, then dried (MgSO$_4$) and concentrated in vacuo. The resultant residue was purified by column chromatography to give the title compound as a cream solid (102 mg, 90%).

$^1$H NMR (400 MHz, CDCl$_3$): δ 2.85 (s, 3H), 3.80-3.86 (m, 4H) and 3.88-3.94 (m, 4H).

Reference Example 18

5-Chloro-7-morpholin-4-yl-thiazolo[4,5-d]pyrimidine-2-carbaldehyde

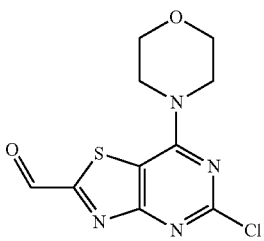

To a solution of 5-chloro-2-methyl-7-morpholin-4-yl-thiazolo[4,5-d]pyrimidine (102 mg, 0.38 mmol) in 1,4-dioxane (5 mL) was added selenium dioxide (51 mg, 0.46 mmol) and the solution heated at 105° C. for 6 h. The reaction mixture was cooled to RT and partitioned between DCM and brine. The organic layer was isolated, then dried (MgSO$_4$) and concentrated in vacuo. The resultant residue was purified by column chromatography to give the title compound as an orange solid (53 mg, 49%).

$^1$H NMR (400 MHz, DMSO-d$_6$): δ 3.73-3.78 (m, 4H), 3.85-3.96 (m, 4H) and 10.12 (s, 1H).

Reference Example 19

5-(5-Chloro-7-morpholin-4-yl-thiazolo[4,5-d]pyrimidin-2-ylmethyl)-hexahydro-pyrrolo[3,4-c]pyrrole-2-carboxylic acid tert-butyl ester

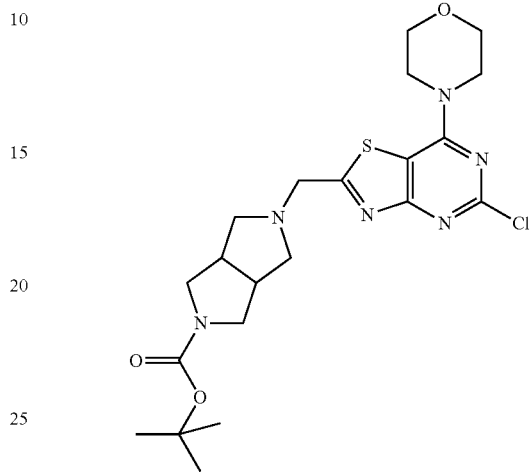

To a solution of 5-chloro-7-morpholin-4-yl-thiazolo[4,5-d]pyrimidine-2-carbaldehyde (25 mg, 0.088 mmol) in 1,2-dichloroethane (1 mL) was added hexahydro-pyrrolo[3,4-c]pyrrole-2-carboxylic acid tert-butyl ester (21 mg, 0.10 mmol). The mixture was stirred at RT for 5 min before sodium triacetoxyborohydride (28 mg, 0.130 mmol) was added. The resulting solution was stirred at RT for 1 h. The crude reaction mixture was partitioned between DCM and brine. The organic layer was isolated, then dried (MgSO$_4$) and concentrated in vacuo. The resultant residue was purified by column chromatography to give the title compound as a white solid (26 mg, 61%).

$^1$H NMR (400 MHz, CDCl$_3$): δ 1.55 (s, 9H), 2.70-2.83 (m, 4H), 2.88 (s, 2H), 3.30 (s, 2H), 3.63 (s, 2H), 3.82-3.87 (m, 4H), 3.93-4.01 (m, 4H) and 4.05-4.17 (m, 2H).

Reference Example 20

1-(tert-Butyl-dimethyl-silanyl)-5-fluoro-1H-indole

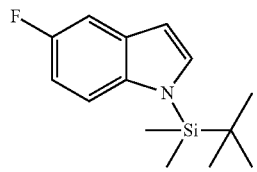

To a solution of 5-fluoro-1H-indole (30.0 g, 0.222 mol) in anhydrous THF (250 mL) was added sodium hydride (60% suspension in mineral oil, 10.22 g, 0.255 mol) portionwise and maintaining the solution at 0° C. The reaction mixture was stirred at 0° C. for 20 min, then a solution of tert-butyl-chloro-dimethyl-silane (40.15 g, 0.266 mol) in anhydrous THF (20 mL) was added and the solution stirred at RT for 25 h. The reaction mixture was poured into H₂O and the layers separated. The aqueous layer was extracted with EtOAc and the combined organic layers were dried (MgSO₄), then concentrated in vacuo. The resultant residue was purified by column chromatography (silica gel, cyclohexane:DCM 100% to 50:50) to provide the title compound as a colourless oil (41.2 g, 74%).

¹H NMR (400 MHz, CDCl₃): δ 0.60 (s, 6H), 0.94 (s, 9H), 6.58 (dd, J=3.2, 1.0 Hz, 1H), 6.87-6.93 (m, 1H), 7.23 (d, J=3.2 Hz, 1H), 7.24-7.29 (m, 1H) and 7.41 (m, 1H).

Reference Example 21

[1-(tert-Butyl-dimethyl-silanyl)-5-fluoro-1H-indol-4-yl]boronic acid

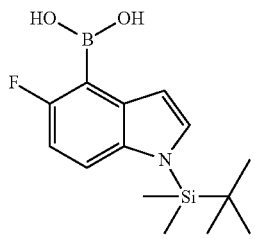

To a solution of 1-(tert-butyl-dimethyl-silanyl)-5-fluoro-1H-indole (30.0 g, 0.12 mol) in anhydrous THF (1000 mL) were added N,N,N',N'-tetramethylethylenediamine (36.6 mL, 0.241 mol) and a solution of s-butyl lithium (1.4 M in cyclohexane, 172 mL, 0.241 mmol) at −78° C. The resulting mixture was stirred at −78° C. for 2 h, then triisopropyl borate (37.5 mL, 162.7 mmol) was added dropwise. The resulting solution was stirred at −78° C. for 40 min, then allowed to warm to −20° C. An aqueous solution of HCl (2.4 M, 250 mL) was added and the resulting mixture was poured into H₂O. The layers were separated and the aqueous layer extracted with EtOAc. The combined organic layers were dried (MgSO₄) and concentrated in vacuo. The resultant yellow solid was then crystallised from DCM and cyclohexane to give the title compound as a white solid (25.0 g, 71%).

¹H NMR (400 MHz, CD₃OD): δ 0.62 (s, 6H), 0.92 (s, 9H), 6.51 (d, J=3.2 Hz, 1H), 6.79-6.90 (m, 1H), 7.30-7.36 (m, 1H) and 7.54 (dd, J=9.0, 4.6 Hz, 1H).

Reference Example 22

5-Fluoro-4-(4,4,5,5-tetramethyl-[1,3,2]dioxaborolan-2-yl)-1H-indole

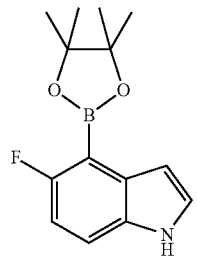

Step 1

A solution of 5-fluoroindole (5 g, 37.0 mmol) in DMF (40 mL) was treated at 0° C. with trifluoroacetic anhydride (6.1 mL, 42.6 mmol). After 30 min, the reaction was poured into water and the resulting precipitate collected by filtration, washed with water, then dried in vacuo. The solid was then dissolved in 10% aqueous NaOH (200 mL) and heated at reflux for 1 h. The reaction mixture was cooled to RT, washed with DCM and acidified with aqueous HCl. The resulting white precipitate was collected by filtration, washed with water, taken up in DCM, washed with water, dried (MgSO₄) and evaporated in vacuo. The resulting material (5 g, 75%) was dissolved in methanol (80 mL) and treated with concentrated sulfuric acid (2 mL) then heated at reflux overnight. The reaction was cooled and the resulting precipitate collected, washed with water and concentrated in vacuo to give 5-fluoro-1H-indole-3-carboxylic acid methyl ester as a peach-coloured solid (4.5 g, 83%).

Step 2

A solution of thallium tris(trifluoroacetate) (8.45 g, 15.6 mmol) in TFA (35 mL) was added to a solution of 5-fluoro-1H-indole-3-carboxylic acid methyl ester (2 g, 10.4 mmol) in TFA (10 mL) at room temperature and stirred for 2 h. The reaction mixture was evaporated in vacuo and the resulting residue suspended in water (25 mL) before being treated with a solution of potassium iodide (5.2 g, 31.3 mmol) in water (50 mL). The reaction mixture was treated with dichloromethane (100 mL) and methanol (5 mL) and the resulting precipitate removed by filtration through celite. The organic layer was separated, washed successively with sodium thiosulfate solution and brine, then dried (MgSO₄) and evaporated in vacuo. The resultant material was dissolved in methanol (60 mL) and treated with 40% aqueous NaOH solution (60 mL) then refluxed for 2 h. The reaction mixture was cooled to RT and extracted with DCM/MeOH (ratio 95:5). The organic layer was dried (MgSO₄), filtered and concentrated in vacuo. The resultant residue was purified by column chromatography (silica gel, pentane:EtOAc 75:25) to provide 5-fluoro-4-iodo-1H-indole as a pale brown solid (1.05 g, 39%).

NMR δ_H (300 MHz, CDCl₃) 6.49-6.52 (m, 1H), 6.95 (apparent dt, J=0.4, 8.6, 1H), 7.26-7.33 (m, 2H) and 8.35 (s, 1H).

Step 3

A solution of 5-fluoro-4-iodo-1H-indole (1.28, 4.90 mmol) in dioxane (5 mL) was treated with triethylamine (1.0 mL, 7.18 mmol), palladium acetate (22.0 mg, 0.098 mmol) and bis(cyclohexyl)phosphino-2-biphenyl (137 mg, 0.40 mmol) then heated to 80° C. A solution of pinacolborane (1 M in THF, 13.0 mL, 13.0 mmol) was added via syringe. After 30 min, the reaction mixture was cooled to RT, then diluted with water (50 mL) and DCM (50 mL). The resulting mixture was passed through a phase separation cartridge, and the organic layer was concentrated in vacuo. The resultant residue was purified by column chromatography (silica gel, pentane:EtOAc 75:25) to provide the title compound as a tan solid (1.06 g, 83%).

[M+H]⁺ 262.1

Reference Example 23

1-Bromo-5-fluoro-2-methyl-3-nitrobenzene

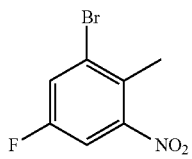

To a solution of 4-fluoro-2-nitrotoluene (10.0 g, 64.4 mmol) in trifluoroacetic acid (40 mL) was added concentrated sulfuric acid (12.5 mL) followed by N-bromosuccinimide (17.2 g, 96.6 mmol) and the reaction mixture was stirred at RT for 16 h. The reaction mixture was then poured onto ice and water and stirred for 15 min. The product was then extracted into EtOAc and the organic layer washed with brine, dried (MgSO$_4$) and concentrated in vacuo to give the title compound as a pale oil which crystallised out on standing (11.76 g, 77%).

NMR $\delta_H$ (300 MHz, CDCl$_3$) 2.59 (s, 3H), 7.50 (dd, J=2.8, 7.6, 1H) and 7.58 (dd, J=2.9, 7.4, 1H).

Reference Example 24

4-Bromo-6-fluoro-1H-indole

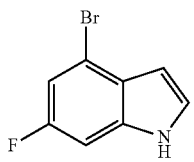

To a solution of 1-bromo-5-fluoro-2-methyl-3-nitro-benzene (7.49 g, 31.8 mmol) in dioxane (40 mL) were added DMF-DMA (21.0 mL, 158 mmol) and pyrrolidine (2.6 mL, 31.1 mmol). The reaction mixture was heated at 100° C. for 3 h. The mixture was cooled to RT and concentrated in vacuo to give 1-[2-(2-bromo-4-fluoro-6-nitro-phenyl)-1-methyl vinyl]-pyrrolidine as a dark red residue. To a suspension of the pyrrolidine (10.0 g, 31.7 mmol) and Raney®-Nickel (suspension in H$_2$O, 15 mL) in MeOH:THF (1:1, 150 mL) was added hydrazine monohydrate (2.3 mL, 47.4 mmol) at 0° C. and the mixture stirred at RT for 5 hours. The reaction mixture was then filtered through Celite and the filter cake washed with EtOAc. The filtrate was concentrated in vacuo and the resulting residue was purified by column chromatography (silica gel, pentane:EtOAc 75:25) to provide the title compound as a pale oil (2.57 g, 37%).

NMR $\delta_H$ (300 MHz, CDCl$_3$) 6.57 (apparent t, J=2.7, 1H), 7.04 (dd, J=2.1, 9.1, 1H), 7.12 (dd, J=2.1, 9.1, 1H), 7.20-7.25 (m, 1H) and 8.25 (s, 1H).

Reference Example 25

6-Fluoro-4-(4,4,5,5-tetramethyl-[1,3,2]dioxaborolan-2-yl)-1H-indole

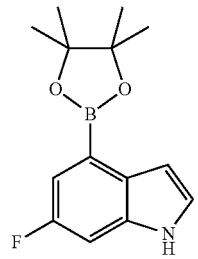

To a solution of 4-bromo-6-fluoro-1H-indole (6.0 g, 25.53 mmol) and bis(pinacolato)diboron (9.7 g, 38.19 mmol) in anhydrous DMSO (120 mL) were added KOAc (7.5 g, 76.41 mmol) and [1,1'-bis(diphenylphosphine)ferrocene]-dichloropalladium (1.0 g, 1.22 mmol). The mixture was heated at 80° C. for 18 h. The reaction mixture was cooled to RT and partioned between EtOAc and H$_2$O. The organic layer was washed successively with H$_2$O and brine, dried (Na$_2$SO$_4$) and concentrated in vacuo. The resulting residue was purified by column chromatography (silica gel, pentane:EtOAc 75:25) to provide the title compound as a white solid (4.6 g, 61%).

NMR $\delta_H$ (300 MHz, CDCl$_3$) 1.39 (s, 12H), 7.02 (m, 1H), 7.14-7.19 (m, 1H), 7.20-7.26 (m, 1H), 7.38 (dd, J=2.4, 9.9, 1H) and 8.16 (s, 1H).

Reference Example 26

2-(5-Chloro-7-morpholin-4-yl-thiazolo[5,4-d]pyrimidin-2-yl)-1-phenyl-ethanol

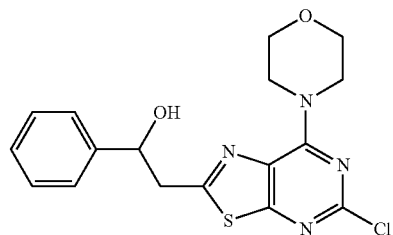

To a solution of 5-chloro-2-methyl-7-morpholin-4-yl-thiazolo[5,4-d]pyrimidine (1.33 g, 4.91 mmol) and N,N,N',N'-tetramethylethylenediamine (0.74 mL, 5.40 mmol) in anhydrous THF (50 mL) was added a solution of n-BuLi (2.5 M in hexanes, 2.4 mL, 6.0 mmol) dropwise at −78° C. The reaction mixture was stirred for 15 min, then a solution of benzaldehyde (0.65 mL, 6.29 mmol) in anhydrous THF (5 mL) was added rapidly. The mixture was stirred at −78° C. for 15 min, then allowed to warm to RT and partitioned between EtOAc and H$_2$O. The organic layer was isolated, washed with brine, then dried (Na$_2$SO$_4$) and concentrated in vacuo. The resultant residue was purified by column chromatography to give the title compound as a yellow solid (1.20 g, 66%).

[M+H]$^+$ 377.0

Reference Example 27

5-Chloro-7-morpholin-4-yl-thiazolo[5,4-d]pyrimidine-2-carbaldehyde

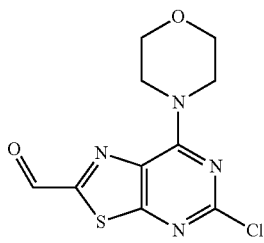

To a suspension of 2-(5-chloro-7-morpholin-4-yl-thiazolo[5,4-d]pyrimidin-2-yl)-1-phenyl-ethanol (1.1 g, 2.9 mmol) in toluene (25 mL) was added p-toluenesulfonic acid (0.11 g, 0.58 mmol) and the resulting solution stirred at 120° C. for 24 h. The reaction mixture was concentrated in vacuo to give 5-chloro-7-morpholin-4-yl-2-styryl-thiazolo[5,4-d]pyrimidine as a crude yellow solid which was used without purification. To a suspension of 5-chloro-7-morpholin-4-yl-2-styryl-thiazolo[5,4-c]pyrimidine (2.9 mmol) in THF (9 mL), acetonitrile (9 mL) and H$_2$O (3 mL) were added ruthenium (III) chloride (18 mg, 0.081 mmol) and periodic acid (1.3 g, 5.80 mmol). The resulting solution was stirred at RT for 2 h, then partitioned between EtOAc and an aqueous solution of sodium thiosulfate. The aqueous layer was isolated and extracted with EtOAc. The combined organic layers were washed with brine, dried (Na$_2$SO$_4$) and concentrated in vacuo. The resultant residue was purified by column chromatography to give the title compound as a yellow solid (0.34 g, 42%).

$^1$H NMR (400 MHz, CDCl$_3$): δ 3.83-3.88 (m, 4H), 4.06-4.15 (m, 2H), 4.72 (m, 2H) and 9.95 (s, 1H).

Reference Example 28

5-(5-Chloro-7-morpholin-4-yl-thiazolo[5,4-d]pyrimidin-2-ylmethyl)-hexahydro-pyrrolo[3,4-c]pyrrole-2-carboxylic acid tert-butyl ester

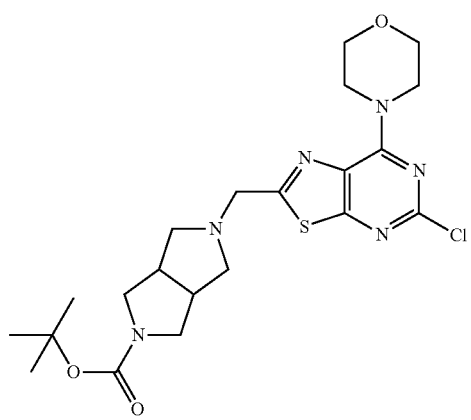

To a solution of 5-chloro-7-morpholin-4-yl-thiazolo[5,4-d]pyrimidine-2-carbaldehyde (57 mg, 0.20 mmol) in 1,2-dichloroethane (2 mL) was added hexahydro-pyrrolo[3,4-c]pyrrole-2-carboxylic acid tert-butyl ester (46 mg, 0.22 mmol). The mixture was stirred at RT for 5 min before sodium triacetoxyborohydride (64 mg, 0.30 mmol) was added. The resulting solution was stirred at RT for 1 h. The crude reaction mixture was partitioned between DCM and brine. The organic layer was isolated, then dried (MgSO$_4$) and concentrated in vacuo. The resultant residue was purified by column chromatography to give the title compound as a white solid (83 mg, 86%).

$^1$H NMR (400 MHz, CDCl$_3$): δ 1.45 (s, 9H), 1.55 (m, 2H), 2.61 (m, 2H), 2.75-2.87 (m, 4H), 3.23 (m, 2H), 3.57 (s, 2H), 3.80 (t, J=4.8 Hz, 4H), 3.91 (m, 2H) and 4.31 (m, 2H).

Reference Example 29

2-(5-Chloro-7-morpholin-4-yl-thiazolo[5,4-d]pyrimidin-2-ylmethyl)-2,7-diaza-spiro[3.5]nonane-7-carboxylic acid tert-butyl ester

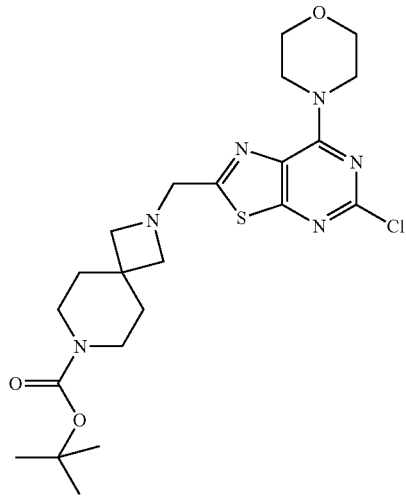

Prepared according to the method used in the preparation of 5-(5-chloro-7-morpholin-4-yl-thiazolo[5,4-d]pyrimidin-2-ylmethyl)-hexahydro-pyrrolo[3,4-c]pyrrole-2-carboxylic acid tert-butyl ester using 2,7-diaza-spiro[3.5]nonane-7-carboxylic acid tert-butyl ester hydrochloride in place of hexahydro-pyrrolo[3,4-c]pyrrole-2-carboxylic acid tert-butyl ester. The title compound was obtained as a white solid (70 mg, 71%).

[M+H]$^+$495.3

Reference Example 30

3-(5-Chloro-7-morpholin-4-yl-thiazolo[5,4-d]pyrimidin-2-ylmethyl)-3,8-diaza-bicyclo[3.2.1]octane-8-carboxylic acid tert-butyl ester

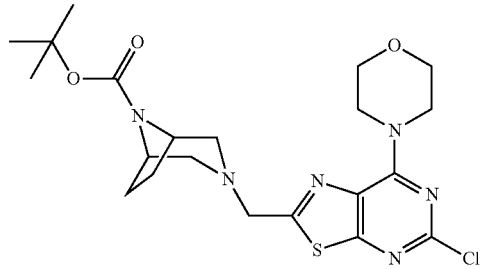

Prepared according to the method used in the preparation of 5-(5-chloro-7-morpholin-4-yl-thiazolo[5,4-d]pyrimidin-2-ylmethyl)-hexahydro-pyrrolo[3,4-c]pyrrole-2-carboxylic acid tert-butyl ester using 3,8-diaza-bicyclo[3.2.1]octane-8-carboxylic acid tert-butyl ester in place of hexahydro-pyrrolo[3,4-c]pyrrole-2-carboxylic acid tert-butyl ester. The title compound was obtained as a white solid (91 mg, 95%).

$^1$H NMR (400 MHz, CDCl$_3$): δ 1.47 (s, 9H), 1.90 (m, 2H), 1.93-2.00 (m, 2H), 2.54 (bs, 2H), 2.74 (dd, J=10.6, 2.6 Hz, 2H), 3.79 (s, 2H), 3.82 (m, 4H) and 4.12-4.43 (m, 6H).

Reference Example 31

2-(4-Azetidin-1-yl-piperidin-1-ylmethyl)-5-chloro-7-morpholin-4-yl-thiazolo[5,4-d]pyrimidine

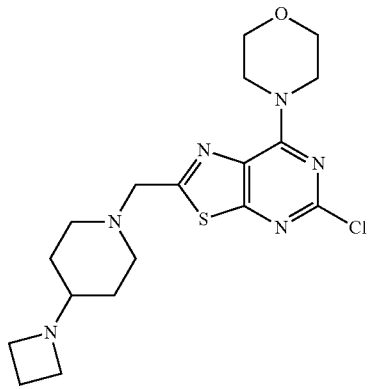

Prepared according to the method used in the preparation of 5-(5-chloro-7-morpholin-4-yl-thiazolo[5,4-d]pyrimidin-2-ylmethyl)-hexahydro-pyrrolo[3,4-c]pyrrole-2-carboxylic acid tert-butyl ester using 4-azetidin-1-yl-piperidine in place of hexahydro-pyrrolo[3,4-c]pyrrole-2-carboxylic acid tert-butyl ester. The title compound was obtained as a cream solid (54 mg, 66%).

[M+H]$^+$ 409.3

Reference Example 32

5-Chloro-2-[(S)-1-(hexahydro-pyrrolo[1,2-a]pyrazin-2-yl)methyl]-7-morpholin-4-yl-thiazolo[5,4-d]pyrimidine

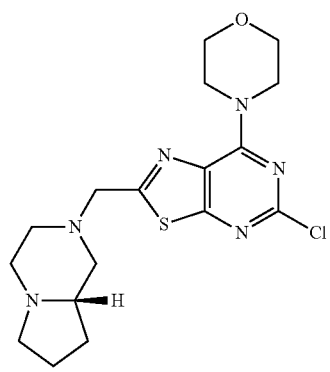

Prepared according to the method used in the preparation of 5-(5-chloro-7-morpholin-4-yl-thiazolo[5,4-d]pyrimidin-2-ylmethyl)-hexahydro-pyrrolo[3,4-c]pyrrole-2-carboxylic acid tert-butyl ester using (S)-octahydro-pyrrolo[1,2-a]pyrazine in place of hexahydro-pyrrolo[3,4-c]pyrrole-2-carboxylic acid tert-butyl ester. The title compound was obtained as a white solid (34 mg, 43%).

[M+H]$^+$ 395.3

Reference Example 33

8-(5-Chloro-7-morpholin-4-yl-thiazolo[5,4-d]pyrimidin-2-ylmethyl)-2,8-diaza-spiro[4.5]decane-2-carboxylic acid tert-butyl ester

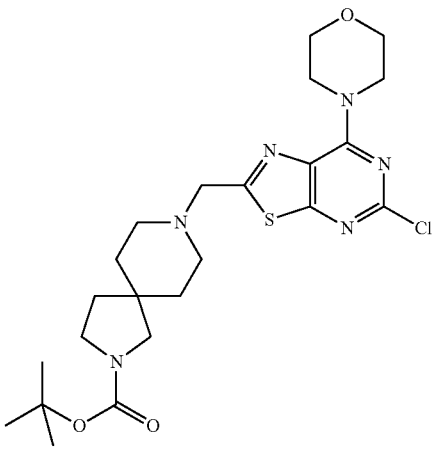

Prepared according to the method used in the preparation of 5-(5-chloro-7-morpholin-4-yl-thiazolo[5,4d]pyrimidin-2-ylmethyl)-hexahydro-pyrrolo[3,4-c]pyrrole-2-carboxylic acid tert-butyl ester using 2,8-diaza-spiro[4.5]decane-2-carboxylic acid tert-butyl ester in place of hexahydro-pyrrolo[3,4-c]pyrrole-2-carboxylic acid tert-butyl ester. The title compound was obtained as a white solid (81 mg, 80%).

[M+H]$^+$ 509.3

Reference Example 34

5-Chloro-2-(cis-3,5-dimethyl-piperazin-1-ylmethyl)-7-morpholin-4-yl-thiazolo[5,4-d]pyrimidine

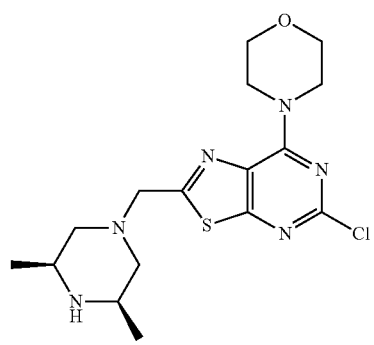

Prepared according to the method used in the preparation of 5-(5-chloro-7-morpholin-4-yl-thiazolo[5,4-d]pyrimidin- 2-ylmethyl)-hexahydro-pyrrolo[3,4-c]pyrrole-2-carboxylic acid tert-butyl ester using cis-2,6-dimethyl-piperazine in place of hexahydro-pyrrolo[3,4-c]pyrrole-2-carboxylic acid tert-butyl ester. The title compound was obtained as a pale yellow solid (32 mg, 42%).

[M+H]+ 383.3

Reference Example 35

2-(5-Chloro-7-morpholin-4-yl-thiazolo[4,5-d]pyrimidin-2-ylmethyl)-2,7-diaza-spiro[3.5]nonane-7-carboxylic acid tert-butyl ester

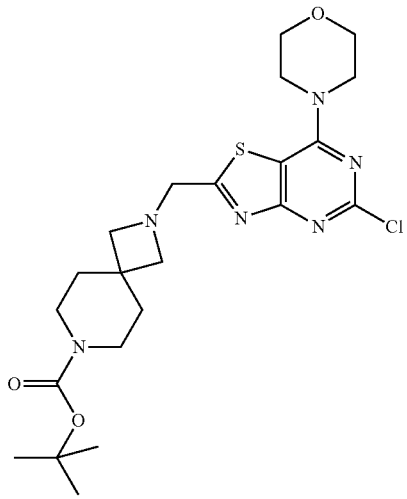

Prepared according to the method used in the preparation of 5-(5-chloro-7-morpholin-4-yl-thiazolo[4,5-d]pyrimidin-2-ylmethyl)-hexahydro-pyrrolo[3,4-c]pyrrole-2-carboxylic acid tert-butyl ester using 2,7-diaza-spiro[3.5]nonane-7-carboxylic acid tert-butyl ester in place of hexahydro-pyrrolo[3,4-c]pyrrole-2-carboxylic acid tert-butyl ester. The title compound was obtained as a white solid (46.4 mg, 72%).

$^1$H NMR (400 MHz, CDCl$_3$): δ 1.43 (s, 9H), 1.73 (t, J=5.3 Hz, 4H), 3.08-3.35 (m, 4H), 3.27-3.37 (m, 4H), 3.78-3.84 (m, 4H), 3.90-3.95 (m, 5H) and 4.07 (d, J=9.0 Hz, 2H).

Reference Example 36

5-Chloro-7-morpholin-4-yl-2-(4-morpholin-4-yl-piperidin-1-ylmethyl)-thiazolo[4,5-d]pyrimidine

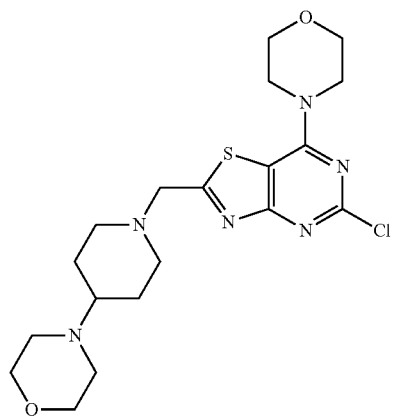

Prepared according to the method used in the preparation of 5-(5-chloro-7-morpholin-4-yl-thiazolo[4,5-d]pyrimidin-2-ylmethyl)-hexahydro-pyrrolo[3,4-c]pyrrole-2-carboxylic acid tert-butyl ester using 4-piperidin-4-yl-morpholine in place of hexahydro-pyrrolo[3,4-c]pyrrole-2-carboxylic acid tert-butyl ester. The title compound was obtained as a cream solid (28 mg, 80%).

$^1$H NMR (400 MHz, CDCl$_3$): δ 1.63 (q, J=12.3 Hz, 2H), 1.92 (d, J=12.3 Hz, 2H), 2.24 (m, 1H), 2.34 (t, J=11.5 Hz, 2H), 2.60 (m, 4H), 3.04 (d, J=11.5 Hz, 2H), 3.76 (t, J=4.4 Hz, 4H), 3.81-3.86 (m, 4H) and 3.92-3.98 (m, 6H).

Reference Example 37

2-Methyl-4-(trifluoromethanesulfonyloxy)thiazole-5-carboxylic acid ethyl ester

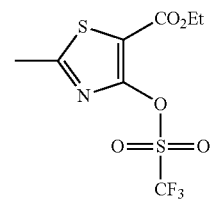

To a solution of 4-hydroxy-2-methylthiazole-5-carboxylic acid ethyl ester (1.87 g, 10 mmol) in DCM (50 mL) at −78° C. under an atmosphere of N$_2$ was added triethylamine (2.08 mL, 15 mmol), followed by dropwise addition of trifluoromethanesulfonic anhydride (1.85 mL, 11 mmol). The resulting mixture was stirred at −78° C. for 1 h then warmed to RT. The solvent was removed in vacuo and the resulting residue was purified by column chromatography to give the title compound as a yellow oil (2.86 g, 90%).

[M+H]+ 320.0

Reference Example 38

6-Benzyl-2-methyl-4H-thiazoo[4,5-d]pyrimidine-5,7-dione

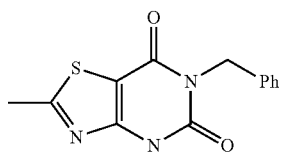

To a solution of 2-methyl-4-(trifluoromethanesulfonyloxy)thiazole-5-carboxylic acid ethyl ester (6.38 g, 20 mmol) in dioxane (80 mL) under an atmosphere of $N_2$ was added cesium carbonate (13.0 g, 40 mmol), benzylurea (3.3 g, 22 mmol), Xantphos (0.58 g, 1 mmol) and tris(dibenzylideneacetone)dipalladium(0) (0.46 g, 0.5 mmol). The resulting mixture was stirred at 60° C. for 18 h, cooled to RT, then poured onto water (500 mL) and stirred for 15 min. The resulting mixture was filtered, the filtrate collected and reduced in volume in vacuo to approximately one-third. The resultant precipitate was collected by filtration, washed with ether and dried in vacuo to give the title compound as a white solid (3.9 g, 72%).

[M+H]$^+$ 274.1

Reference Example 39

4-(5-Chloro-7-morpholin-4-ylthiazolo[4,5-d]pyrimidin-2-ylmethyl)-2,2-dimethylpiperazine-1-carboxylic acid tert-buty ester

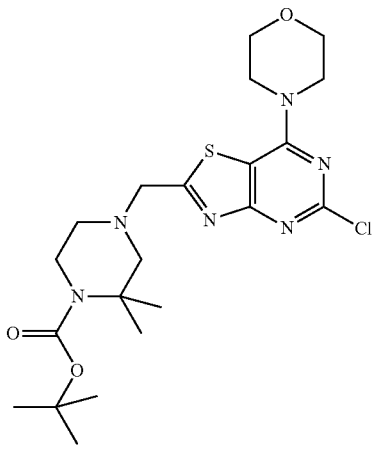

Prepared according to the method used in the preparation of 5-(5-chloro-7-morpholin-4-ylthiazolo[4,5-d]pyrimidin-2-ylmethyl)-hexahydro-pyrrolo[3,4-c]pyrrole-2-carboxylic acid tert-butyl ester using 2,2-dimethylpiperazine-1-carboxylic acid tert-butyl ester in place of hexahydro-pyrrolo[3,4-c]pyrrole-2-carboxylic acid tert-butyl ester. The title compound was obtained as a yellow solid (100 mg, 38%).

[M+H]$^+$ 483.2

Reference Example 40

5-Chloro-7-morpholin-4-yl-2-(4-morpholin-4-ylpiperidin-1-ylmethyl)thiazolo[4,5-d]pyrimidine

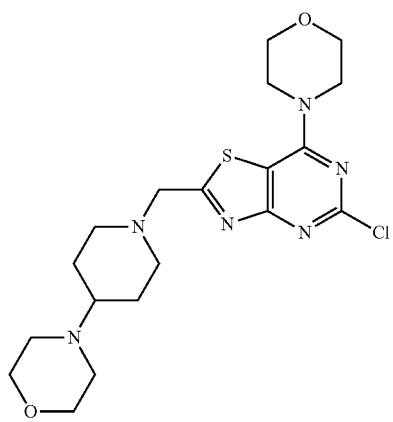

Prepared according to the method used in the preparation of 5-(5-chloro-7-morpholin-4-ylthiazolo[4,5-d]pyrimidin-2-ylmethyl)-hexahydro-pyrrolo[3,4-c]pyrrole-2-carboxylic acid tert-butyl ester using 4-piperidin-4-ylmorpholine in place of hexahydro-pyrrolo[3,4-c]pyrrole-2-carboxylic acid tert-butyl ester. The title compound was obtained as a yellow solid (220 mg, 39%).

[M+H]$^+$ 439.2

Reference Example 41

5-Chloro-2-[(S)-1-(hexahydro-pyrrolo[1,2-a]pyrazin-2-yl)methyl]-7-morpholin-4-ylthiazolo[4,5-d]pyrimidine

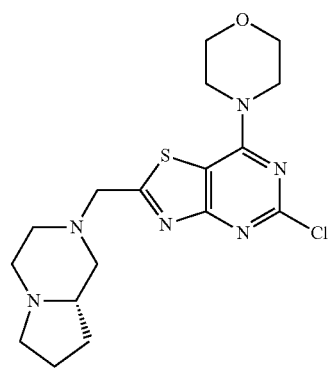

Prepared according to the method used in the preparation of 5-(5-chloro-7-morpholin-4-ylthiazolo[4,5-d]pyrimidin-2-ylmethyl)-hexahydro-pyrrolo[3,4-c]pyrrole-2-carboxylic acid tert-butyl ester using (S)-octahydro-pyrrolo[1,2-a]pyrazine in place of hexahydro-pyrrolo[3,4-c]pyrrole-2-carboxylic acid tert-butyl ester. The title compound was obtained as an orange solid (131 mg, 46%).

[M+H]$^+$ 395.4

Reference Example 42

4-Azetidin-1-yl-piperidine

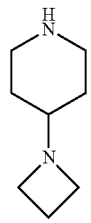

To a solution of 4-oxo-piperidine-1-carboxylic acid tert-butyl ester (1.75 g, 8.88 mmol) in dichloroethane (80 mL) was added azetidine (0.6 g, 10.53 mmol) and the mixture was stirred at RT for 30 min. Sodium triacetoxyborohydride (3.9 g, 18.44 mmol) was added and the resulting solution was stirred at RT for 18 h. The reaction mixture was partitioned between water and DCM and the layers separated. The organic layer was extracted further with DCM and the combined aqueous layers were concentrated in vacuo. The resultant white semi-solid was suspended in DCM and a saturated aqueous solution of $NaHCO_3$ was added. The layers were thoroughly mixed, the organic layer isolated and the aqueous layer further extracted with DCM. The combined organic layers were washed with brine, dried ($Na_2SO_4$) and concentrated in vacuo to give 4-azetidin-1-yl-piperidine-1-carboxylic acid tert-butyl ester as a white solid (2.0 g, 95%). BOC-deprotection of 4-azetidin-1-yl-piperidine-1-carboxylic acid tert-butyl ester (400 mg, 1.67 mmol) using TFA:DCM (1:4) gave the title compound as a yellow oil (185 mg, 79%)

NMR $\delta_H$ (400 MHz, $CDCl_3$) 1.04-1.16 (m, 2H), 1.68 (d, J=12.8 Hz, 2H), 1.98-2.08 (m, 3H), 2.55 (td, J=12.1, 2.6 Hz, 2H), 3.06 (dt, J=12.8, 3.6 Hz, 2H) and 3.15 (t, J=6.9 Hz, 4H).

Reference Example 43

2-(4-Azetidin-1-ylpiperidin-ylmethyl)-5-chloro-7-morpholin-4-ylthiazolo[4,5-d]pyrimidine

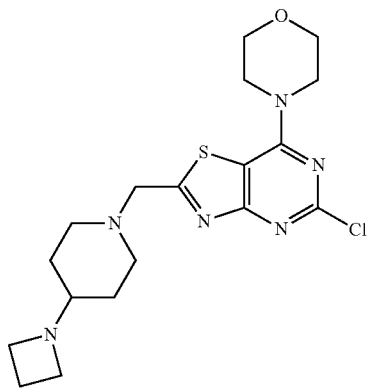

Prepared according to the method used in the preparation of 5-(5-chloro-7-morpholin-4-ylthiazolo[4,5-d]pyrimidin-2-ylmethyl)-hexahydro-pyrrolo[3,4-c]pyrrole-2-carboxylic acid tert-butyl ester using 4-azetidin-1-yl piperidine in place of hexahydro-pyrrolo[3,4-c]pyrrole-2-carboxylic acid tert-butyl ester. The title compound was obtained as a yellow solid (97 mg, 33%).

$[M+H]^+$ 409.3 ($^{35}Cl$) and 411.3 ($^{37}Cl$)

Reference Example 44

5-Chloro-2-(4-cyclopropylmethylpiperazin-1-ylmethyl)-7-morpholin-4-ylthiazolo[4,5-d]pyrimidine

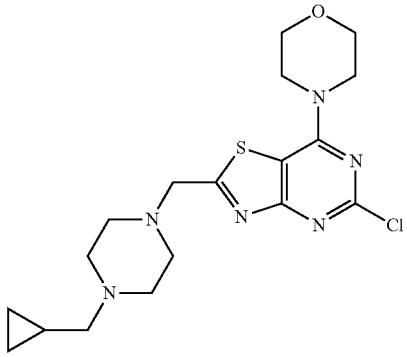

Prepared according to the method used in the preparation of 5-(5-chloro-7-morpholin-4-ylthiazolo[4,5-d]pyrimidin-2-ylmethyl)-hexahydro-pyrrolo[3,4-c]pyrrole-2-carboxylic acid tert-butyl ester using 1-cyclopropylmethylpiperazine in place of hexahydro-pyrrolo[3,4-c]pyrrole-2-carboxylic acid tert-butyl ester. The title compound was obtained as a yellow solid (170 mg, 58%).

$[M+H]^+$ 409.5

Reference Example 45

[1-(5-Chloro-7-morpholin-4-ylthiazolo[4,5-d]pyrimidin-2-ylmethyl)-piperidin-4-yl]dimethylamine

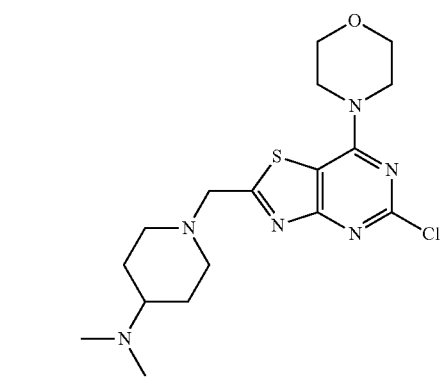

Prepared according to the method used in the preparation of 5-(5-chloro-7-morpholin-4-ylthiazolo[4,5-d]pyrimidin-2-ylmethyl)-hexahydro-pyrrolo[3,4-c]pyrrole-2-carboxylic acid tert-butyl ester using dimethylpiperidin-4-ylamine in place of hexahydro-pyrrolo[3,4-c]pyrrole-2-carboxylic acid tert-butyl ester. The title compound was obtained as an orange solid (244 mg, 40%).

$[M+H]^+$ 397.2 ($^{35}Cl$) and 399.2 ($^{37}Cl$)

Reference Example 46

2-[4-(5-Chloro-7-morpholin-4-yl-thiazolo[4,5-d]pyrimidin-2-ylmethyl)-piperazin-1-yl]-isobutyramide

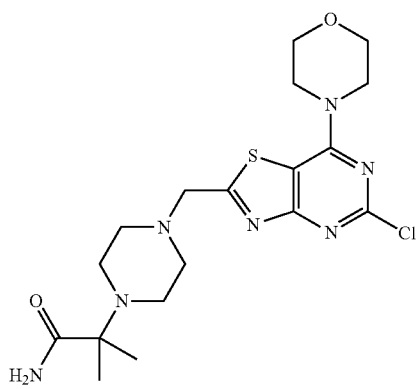

To a solution of tert-butyl-1-piperazinecarboxylate (15.0 g) in dichloromethane (150 mL) and methanol (150 mL) at 0° C. was added hydrogen chloride (40 mL; 2M solution in diethyl ether). The mixture was stirred at room temperature for 1.5 hours and reduced in vacuo to yield tent-butyl-1-piperazinecarboxylate hydrochloride (17.9 g).

To a solution of tent-butyl-1-piperazinecarboxylate hydrochloride (17.9 g) in water (200 mL) at room temperature was added sodium cyanide (3.94 g). A solution of acetone (5.9 mL) in water (20 mL) was then added dropwise and stirred at room temperature for 48 hours. The mixture was partitioned between ethyl acetate and water. The combined organic layers were washed with brine, separated, dried (MgSO$_4$) and reduced in vacuo to yield 4-(cyano-dimethyl-methyl)-piperazine-1-carboxylic acid tert-butyl ester (17.5 g).

To a solution of 4-(cyano-dimethyl-methyl)-piperazine-1-carboxylic acid tert-butyl ester (960 mg) in methyl sulfoxide (20 mL) at 0° C. was added potassium carbonate (104 mg). Hydrogen peroxide (2.0 mL; 27.5 wt % solution in water) was then added dropwise. The resulting mixture was heated to 40° C. overnight. To the cooled mixture was added water and the precipitated solid filtered and dried yielding 4-(1-carbamoyl-2-methyl-ethyl)-piperazine-1-carboxylic acid tert-butyl ester (677 mg). The BOC-group was removed using HCl in ether under standard conditions to give 2-piperazine-1-yl-isobutyramide di-hydrochloride (600 mg).

The title compounds was prepared according to the method used in the preparation of 5-(5-chloro-7-morpholin-4-ylthiazolo[4,5-d]pyrimidin-2-ylmethyl)-hexahydro-pyrrolo[3,4-c]pyrrole-2-carboxylic acid tert-butyl ester using 2-piperazin-1-yl-isobutyramide in place of hexahydro-pyrrolo[3,4-c]pyrrole-2-carboxylic acid tert-butyl ester. The title compound was obtained as an off-white solid (71 mg, 36%).

[M+H]$^+$ 440.2

Reference Example 47

2-(4-Azetidin-1-ylpiperidin-1-ylmethyl)-5-chloro-7-morpholin-4-ylthiazolo[5,4-d]pyrimidine

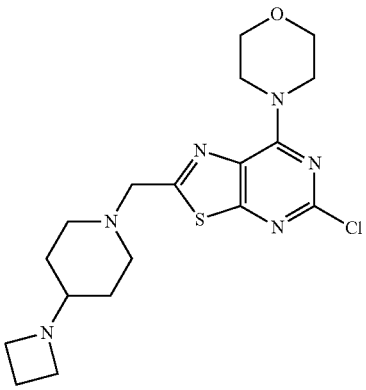

To a solution of 5-chloro-7-morpholin-4-ylthiazolo[5,4-d]pyrimidine-2-carbaldehyde (308 mg, 1.08 mmol) in DCE (8 mL) was added 4-azetidin-1-ylpiperidine (166 mg, 1.19 mmol). The resulting mixture was stirred at RT for 10 min then sodium triacetoxyborohydride (297 mg, 1.40 mmol) was added and stirring was continued for 18 h. The reaction mixture was loaded onto an Isolute® SCX-2 cartridge, washed with MeOH then eluted with 2 M NH$_3$ in MeOH and concentrated in vacuo to give the title compound as an off-white solid (263 mg, 60%).

[M+H]$^+$ 409.2

Reference Example 48

4-(5-Chloro-7-morpholin-4-ylthiazolo[5,4-d]pyrimidin-2-ylmethyl)-piperazine-1-carboxylic acid tert-butyl ester

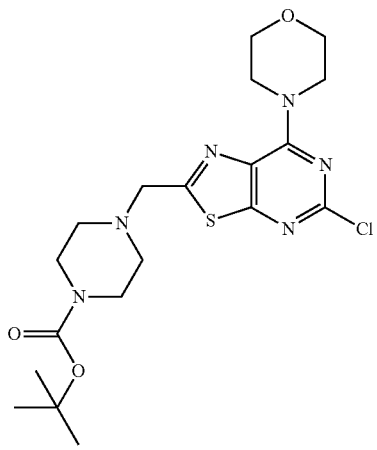

Prepared according to the method used in the preparation of 2-(4-azetidin-1-ylpiperidin-1-ylmethyl)-5-chloro-7-morpholin-4-ylthiazolo[5,4-c]pyrimidine using piperazine-1- carboxylic acid tert-butyl ester in place of 4-azetidin-1-ylpiperidine. The title compound was obtained as a white solid (129 mg, 81%).

[M+H]+ 455.2

Reference Example 49

5-Chloro-2-(4-cyclopropylpiperazin-1-ylmethyl)-7-morpholin-4-ylthiazolo[5,4-d]pyrimidine

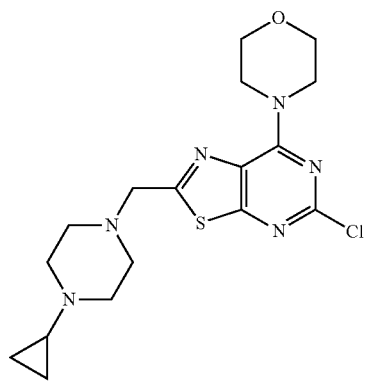

Prepared according to the method used in the preparation of 2-(4-azetidin-1-ylpiperidin-1-ylmethyl)-5-chloro-7-morpholin-4-ylthiazolo[5,4-c]pyrimidine using 1-cyclopropylpiperazine in place of 4-azetidin-1-ylpiperidine. The title compound was obtained as a white solid (117 mg, 56%).

[M+H]+ 395.5

Reference Example 50

2-[4-(5-Chloro-7-morpholin-4-ylthiazolo[5,4-d]pyrimidin-2-ylmethyl)piperazin-1-yl]isobutyramide

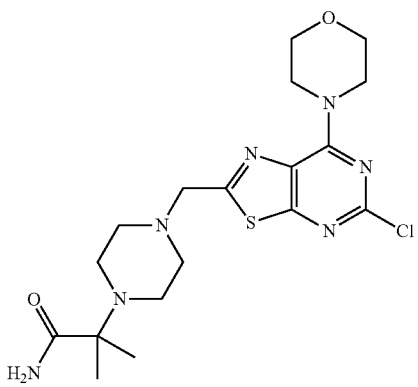

Prepared according to the method used in the preparation of 2-(4-azetidin-1-ylpiperidin-1-ylmethyl)-5-chloro-7-morpholin-4-ylthiazolo[5,4-d]pyrimidine using 2-piperazin-1-ylisobutyramide in place of 4-azetidin-1-ylpiperidine. The title compound was obtained as a white solid (70 mg, 46%).

[M+H]+ 440.3

Reference Example 51

[1-(5-Chloro-7-morpholin-4-ylthiazolo[5,4-d]pyrimidin-2-ylmethyl)piperidin-4-yl]dimethylamine

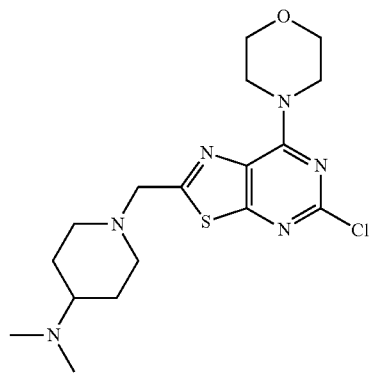

Prepared according to the method used in the preparation of 2-(4-azetidin-1-ylpiperidin-1-ylmethyl)-5-chloro-7-morpholin-4-ylthiazolo[5,4-d]pyrimidine using dimethylpiperidin-4-ylamine in place of 4-azetidin-1-ylpiperidine. The title compound was obtained as a pale yellow solid (101 mg, 72%).

[M+H]+ 397.4

Reference Example 52

5-Chloro-7-morpholin-4-yl-2-(4-morpholin-4-ylpiperidin-1-ylmethyl)-thiazolo[5,4-d]pyrimidine

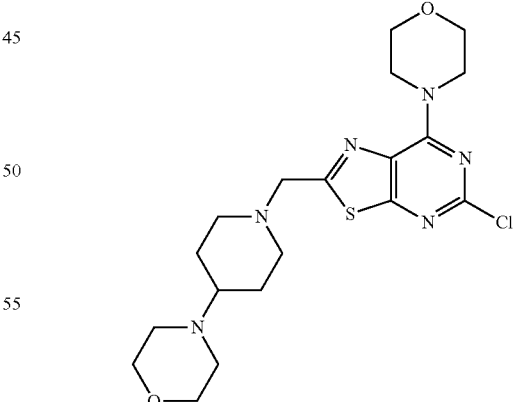

Prepared according to the method used in the preparation of 2-(4-azetidin-1-ylpiperidin-1-ylmethyl)-5-chloro-7-morpholin-4-ylthiazolo[5,4-c]pyrimidine using 4-piperidin-4-ylmorpholine in place of 4-azetidin-1-ylpiperidine. The title compound was obtained as a white solid (104 mg, 67%).

[M+H]+ 397.4

Example 1

5-(6-Fluoro-1H-indol-4-yl)-2-(hexahydro-pyrrolo[3,4-c]pyrrol-2-ylmethyl)-7-morpholin-4-yl-thiazolo[4,5-d]pyrimidine

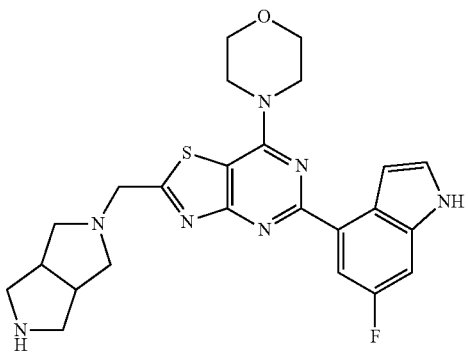

This compound was produced using the Suzuki coupling Method B described in Reference Example 2 above, followed by BOC-deprotection using TFA:DCM (1:1). The title compound was obtained as a pale yellow film (2.0 mg, 16%).

[M+H]$^+$ 480.2

$^1$H NMR (400 MHz, CH$_3$OH-d$_4$): δ 2.63 (dd, J=9.6, 5.6 Hz, 2H), 3.01 (d, J=9.6 Hz, 2H), 3.06 (m, 2H), 3.20 (dd, J=11.8, 4.3 Hz, 2H), 3.45-3.54 (m, 2H), 3.89 (t, J=4.8 Hz, 4H), 4.07 (t, J=4.8 Hz, 4H), 4.18 (s, 2H), 7.24 (dd, J=11.3, 2.4, 1H), 7.35 (d, J=3.2 Hz, 1H), 7.44 (dd, J=3.2, 1 Hz, 1H) and 7.88 (dd, J=11.3, 2.4 Hz, 1H).

Example 2

5-(6-Fluoro-1H-indol-4-yl)-2-(hexahydro-pyrrolo[3,4-c]pyrrol-2-ylmethyl)-7-morpholin-4-yl-thiazolo[5,4-d]pyrimidine

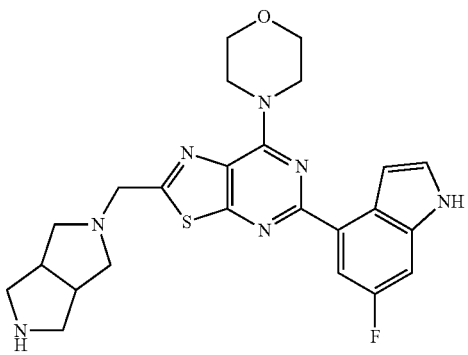

Prepared by using the Suzuki coupling Method B of Reference Example 2 (scheme B), followed by BOC-deprotection using TFA:DCM (1:2) according to Reference Example 3. The title compound was obtained as an off-white solid (2.0 mg, 16%).

[M+H]$^+$ 480.13

$^1$H NMR (400 MHz, CD$_3$OD): δ 2.57 (dd, J=9.6, 5.3 Hz, 2H), 2.98 (d, J=9.6 Hz, 2H), 2.99-3.06 (m, 2H), 3.13 (dd, J=11.7, 5.3 Hz, 2H), 3.57 (dd, J=11.7, 7.2 Hz, 2H), 3.87 (t, J=4.7 Hz, 4H), 4.06 (s, 2H), 4.45 (t, J=4.7 Hz, 4H), 7.22 (dd, J=10.6, 2.4 Hz, 1H), 7.30 (dd, J=3.2, 0.9 Hz, 1H), 7.34 (d, J=3.2 Hz, 1H) and 7.77 (dd, J=10.6, 2.4 Hz, 1H).

Example 3

2-(2,7-Diaza-spiro[3,5]non-2-ylmethyl)-5-(1H-indol-4-yl)-7-morpholin-4-yl-thiazolo[5,4-d]pyrimidine

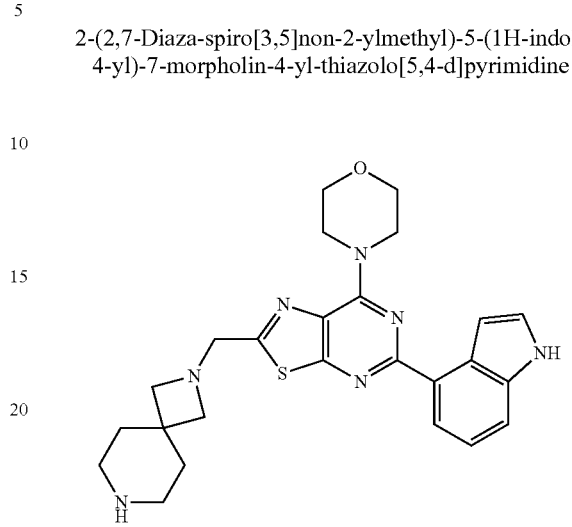

Prepared by using the Suzuki coupling Method B of Reference Example 2 (scheme B), followed by BOC-deprotection using TFA:DCM (1:2) according to Reference Example 3. The title compound was obtained as a off-white solid (15 mg, 29%).

[M+H]$^+$ 476.3

$^1$H NMR (400 MHz, CDCl$_3$): δ δ 1.74-1.79 (m, 4H), 2.79 (t, J=5.3 Hz, 4H), 3.21 (s, 4H), 3.88-3.94 (m, 4H), 3.99 (s, 2H), 4.45 (m, 4H), 7.30 (t, J=7.7 Hz, 1H), 7.33 (t, J=2.7 Hz, 1H), 7.49-7.53 (m, 2H), 8.18 (dd, J=7.7, 1.0 Hz, 1H) and 8.30 (bs, 1H).

Example 4

2-(2,7-Diaza-spiro[3,5]non-2-ylmethyl)-5-(6-fluoro-1H-indol-4-yl)-7-morpholin-4-yl-thiazolo[5,4-d]pyrimidine

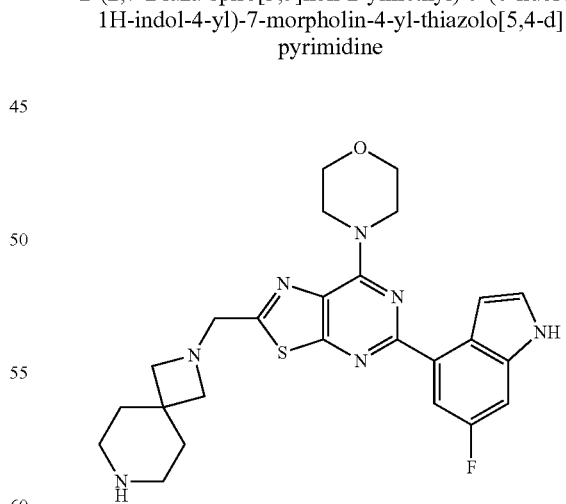

Prepared by using the Suzuki coupling Method B of Reference Example 2 (scheme B), followed by BOC-deprotection using TFA:DCM (1:2) according to Reference Example 3. The title compound was obtained as a pale grey solid (20 mg, 58%).

[M+H]$^+$ 494.3

¹H NMR (400 MHz, CDCl₃): δ 1.77 (t, J=5.4 Hz, 4H), 2.79 (t, J=5.4 Hz, 4H), 3.21 (s, 4 H), 3.90 (t, J=4.6 Hz, 4H), 3.99 (s, 2H), 4.45 (t, J=4.6 Hz, 4H), 7.18 (dd, J=8.8, 2.5 Hz, 1H), 7.31 (t, J=2.5 Hz, 1H), 7.51 (m, 1H), 7.95 (m, 1H) and 8.27 (bs, 1H).

Example 5

2-(2,7-Diaza-spiro[3.5]non-2-ylmethyl)-5-(5-fluoro-1H-indol-4-yl)-7-morpholin-4-yl-thiazolo[5,4-d]pyrimidine

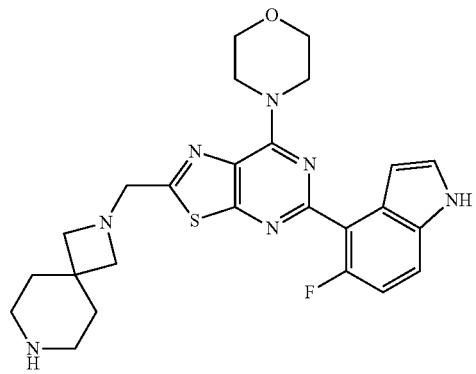

Prepared by using the Suzuki coupling Method B of Reference Example 2 (scheme B), followed by BOC-deprotection using TFA:DCM (1:2) according to Reference Example 3 and TBDMS-deprotection using TBAF:THF (1:10) according to Reference Example 4. The title compound was obtained as a grey solid (49 mg, 55%).

[M+H]⁺ 494.3
¹H NMR (400 MHz, CDCl₃): δ 1.75 (t, J=5.3 Hz, 4H), 2.78 (t, J=5.3 Hz, 4H), 3.20 (s, 4 H), 3.86 (m, 4H), 4.00 (s, 2H), 4.42 (m, 4H), 6.93 (bs, 1H), 7.04 (dd, J=11.0, 8.8 Hz, 1H), 7.28 (m, 1H), 7.37 (dd, J=8.8, 3.8 Hz, 1H) and 8.32 (bs, 1H).

Example 6

2-(3,8-Diaza-bicyclo[3.2.1]oct-3-ylmethyl)-5-(1H-indol-4-yl)-7-morpholin-4-yl-thiazolo[5,4-d]pyrimidine

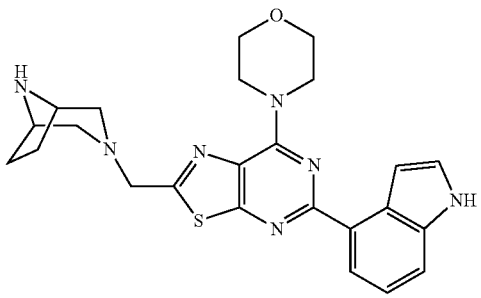

Prepared by using the Suzuki coupling Method B of Reference Example 2 (scheme B), followed by BOC-deprotection using TFA:DCM (1:2) according to Reference Example 3. The title compound was obtained as a white solid (3.0 mg, 7%).

[M+H]⁺ 462.2
¹H NMR (400 MHz, CD₃OD): δ 2.03-2.08 (m, 2H), 2.27-2.33 (m, 2H), 2.73 (d, J=12.5 Hz, 2H), 3.03 (dd, J=12.5, 2.7 Hz, 2H), 3.83-3.88 (m, 4H), 4.02 (m, 4H), 4.45 (m, 4H), 7.20 (t, J=7.8 Hz, 1H), 7.27 (dd, J=3.2, 0.9 Hz, 1H), 7.35 (d, J=3.2 Hz, 1H), 7.52 (apparent dt, J=7.8, 0.9 Hz, 1H) and 7.98 (dd, J=7.8, 0.9 Hz, 1H).

Example 7

2-(4-Azetidin-1-yl-piperidin-1-ylmethyl)-5-(1H-indol-4-yl)-7-morpholin-4-yl-thiazolo[5,4-d]pyrimidine

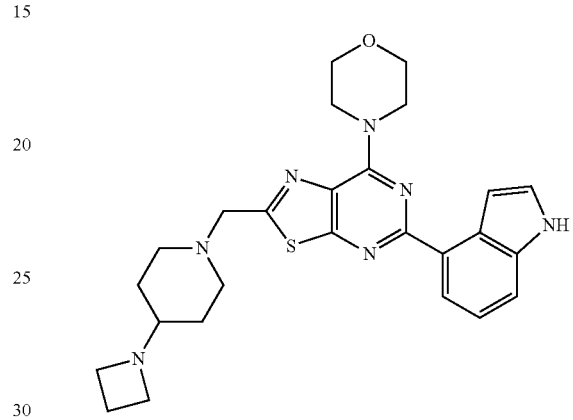

Prepared by using the Suzuki coupling Method B of Reference Example 2 (scheme B), followed by BOC-deprotection using TFA:DCM (1:2) according to Reference Example 3. The title compound was obtained as a off-white solid (15 mg, 24%).

[M+H]⁺ 490.3
¹H NMR (400 MHz, CD₃OD): δ 1.15-1.29 (m, 2H), 1.67 (d, J=12.1 Hz, 2H), 1.92-2.00 (m, 2H), 2.23 (t, J=11.30 Hz, 2H), 2.86 (d, J=11.0 Hz, 2H), 3.21 (m, 3H), 3.80 (m, 4H), 3.88 (s, 2H), 4.34 (m, 4H), 7.19 (apparent t, J=7.8 Hz, 1H), 7.33 (s, 1H), 7.45 (t, J=2.7 Hz, 1H), 7.53 (d, J=7.8 Hz, 1H), 8.09 (d, J=7.8 Hz, 1H) and 11.25 (bs, 1H).

Example 8

2-[(S)-1-(Hexahydro-pyrrolo[1,2-a]pyrazin-2-yl)methyl]-5-(1H-indol-4-yl)-7-morpholin-4-yl-thiazolo[5,4-d]pyrimidine

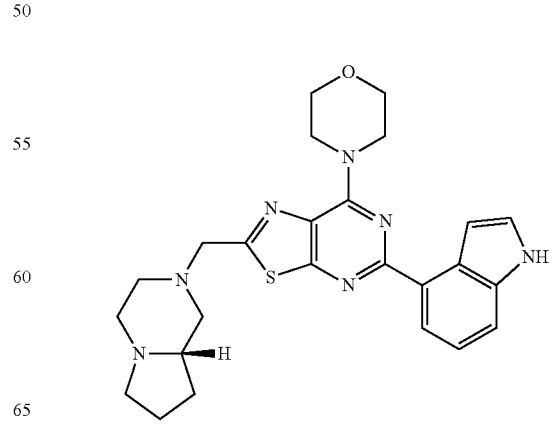

Prepared by using the Suzuki coupling Method B of Reference Example 2 (scheme B). The title compound was obtained as a pale yellow solid (34 mg, 83%).

[M+H]$^+$ 476.2

$^1$H NMR (400 MHz, CDCl$_3$): δ 1.46 (m, 1H), 1.60 (m, 1H), 1.67-1.93 (m, 3H), 2.13-2.29 (m, 2H), 2.41 (m, 1H), 2.55 (m, 1H), 2.96 (d, J=10.9 Hz, 1H), 3.01-3.14 (m, 3H), 3.86-3.94 (m, 6H), 4.44 (t, J=4.6 Hz, 4H), 7.28-7.33 (m, 2H), 7.47-7.52 (m, 2H), 8.17 (dd, J=7.5, 1.0 Hz, 1H) and 8.29 (bs, 1H).

Example 9

2-(3,5-Dimethyl-piperazin-1-ylmethyl)-5-(1H-indol-4-yl)-7-morpholin-4-yl-thiazolo[5,4-d]pyrimidine

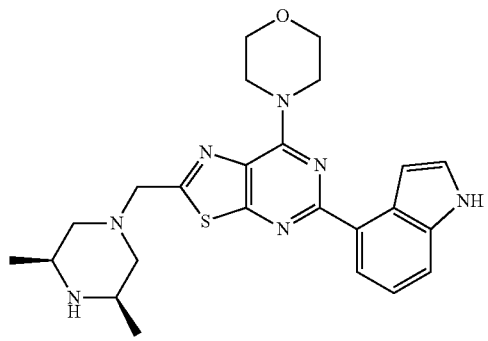

Prepared by using the Suzuki coupling Method of Reference Example 2 (scheme B). The title compound was obtained as a beige solid (24 mg, 62%).

[M+H]$^+$ 464.3

$^1$H NMR (400 MHz, CDCl$_3$): δ 1.05 (d, J=6.4 Hz, 6H), 1.86 (t, J=10.5 Hz, 2H), 2.86-2.92 (m, 2H), 2.96-3.06 (m, 2H), 3.84 (s, 2H), 3.89 (t, J=4.6 Hz, 4H), 4.44 (t, J=4.6 Hz, 4H), 7.26-7.33 (m, 2H), 7.47-7.52 (m, 2H), 8.17 (dd, J=7.7, 0.9 Hz, 1H) and 8.29 (bs, 1H).

Example 10

2-(2,7-Diaza-spiro[3.5]non-2-ylmethyl)-5-(6-fluoro-1H-indol-4-yl)-7-morpholin-4-yl-thiazolo[4,5-d]pyrimidine formate

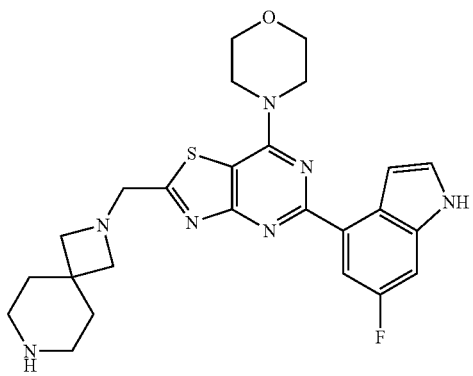

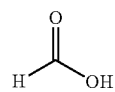

Prepared using the Suzuki coupling Method B of Reference Example 2 (scheme A), followed by BOC-deprotection using TFA:DCM (2:3) according to Reference Example 3. The formate salt of the title compound was obtained as a cream solid (2.6 mg, 12%).

[M+H]$^+$ 494.2

$^1$H NMR (400 MHz, CD$_3$OD): δ 2.02 (t, J=5.6 Hz, 4H), 3.08-3.14 (m, 4H), 3.37 (s, 4H), 3.89 (t, J=4.7 Hz, 4H), 4.07 (t, J=4.7 Hz, 4H), 4.19 (s, 2H), 7.23 (ddd, J=10.0, 2.4, 0.9 Hz, 1H), 7.34 (d, J=3.2 Hz, 1H), 7.42 (dd, J=3.2, 0.9 Hz, 1H), 7.86 (dd, J=10.0, 2.4 Hz, 1H) and 8.54 (bs, 1H).

Example 11

5-(1H-Indol-4-yl)-7-morpholin-4-yl-2-(4-morpholin-4-yl-piperidin-1-ylmethyl)-thiazolo[4,5-d]pyrimidine

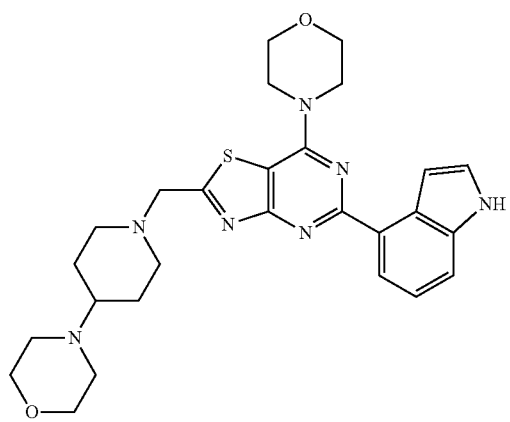

Prepared by using the Suzuki coupling Method B of Reference Example 2 (Scheme A). The title compound was obtained as tan glass (10 mg, 20%).

[M+H]$^+$ 520.2

$^1$H NMR (400 MHz, DMSO-d$_6$): δ 1.41-1.54 (m, 2H), 1.81 (d, J=12.3 Hz, 2H), 2.11-2.22 (m, 1H), 2.23-2.36 (m, 2H), 2.44-2.49 (m, 4H), 3.02 (d, J=11.2 Hz, 2H), 3.57 (t, J=4.3 Hz, 4H), 3.82 (t, J=4.6 Hz, 4H), 3.98 (t, J=4.6 Hz, 4H), 4.01 (s, 2H), 7.21 (t, J=7.8 Hz, 1H), 7.42-7.48 (m, 2H), 7.54 (d, J=8.0 Hz, 1H), 8.14 (dd, J=7.8, 1.0 Hz, 1H) and 11.25 (bs, 1H).

Example 12

2-(3,3-Dimethylpiperazin-1-ylmethyl)-5-(5-fluoro-1H-indol-4-yl)-7-morpholin-4-ylthiazolo[4,5-d]pyrimidine

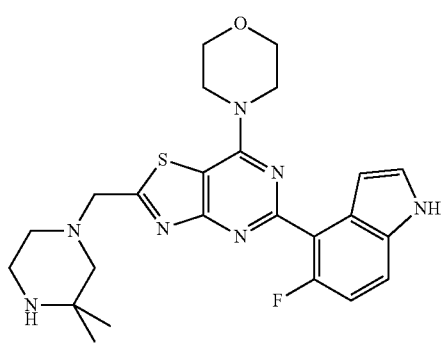

Prepared using Suzuki coupling method C, followed by TBS and BOC-deprotection. The title compound was obtained as a yellow solid (13 mg, 22%).

[M+H]+ 482.1

1H NMR (400 MHz, DMSO): δ 1.16 (s, 6H), 2.31-2.38 (m, 2H), 2.57 (m, 2H), 2.87-2.94 (m, 2H), 3.74-3.80 (m, 4H), 3.92 (m, 4H), 3.98 (s, 2H), 6.73 (m, 1H), 7.07 (dd, J=11.4, 8.8 Hz, 1H), 7.45 (m, 1H), 7.48 (dd, J=8.9, 4.0 Hz, 1H) and 11.28 (s, 1H).

Example 13

5-(5-Fluoro-1H-indol-4-yl)-7-morpholin-4-yl-2-(4-morpholin-4-ylpiperidin-1-ylmethyl)thiazolo[4,5-d]pyrimidine

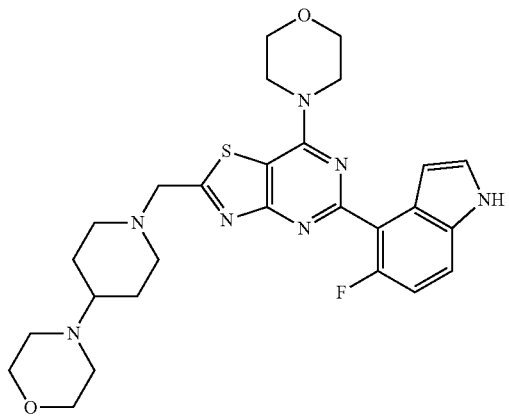

Prepared by using Suzuki coupling method G. The title compound was obtained as a pale yellow solid (101 mg, 76%).

[M+H]+ 538.1

1H NMR (400 MHz, DMSO): δ 1.42-1.55 (m, 2H), 1.80 (d, J=11.8 Hz, 2H), 2.17 (tt, J=11.1, 3.6 Hz, 1H), 2.22-2.31 (m, 2H), 2.44-2.49 (m, 4H), 3.02 (d, J=11.6 Hz, 2H), 3.58 (m, 4H), 3.77 (m, 4H), 3.92 (m, 4H), 4.01 (s, 2H), 6.73 (m, 1H), 7.02 (dd, J=11.0, 8.9 Hz, 1H), 7.43-7.50 (m, 2H) and 11.27 (bs, 1H).

Example 14

5-(1H-Indol-4-yl)-7-morpholin-4-yl-2-(4-morpholin-4-ylpiperidin-1-ylmethyl)thiazolo[4,5-d]pyrimidine

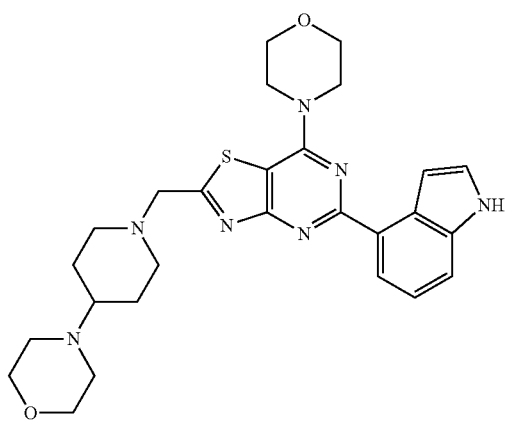

Prepared by using Suzuki coupling method F. The title compound was obtained as an off-white solid (55 mg, 43%).

[M+H]+ 520.2

1H NMR (400 MHz, CDCl3): δ 1.63 (m, 2H), 1.91 (d, J=11.8 Hz, 2H), 2.17-2.28 (m, 1H), 2.29-2.39 (m, 2H), 2.53-2.65 (m, 4H), 3.09 (d, J=11.1 Hz, 2H), 3.72-3.78 (m, 4H), 3.89-3.95 (m, 4H), 4.00 (s, 2H), 4.03-4.08 (m, 4H), 7.27-7.35 (m, 2H), 7.51 (d, J=8.2 Hz, 1H), 7.68 (m, 1H), 8.32 (bs, 1H) and 8.36 (m, 1H).

Example 15

5-(5-Fluoro-1H-indol-4-yl)-2-[(S)-1-(hexahydropyrrolo[1,2-a]pyrazin-2-yl)methyl]-7-morpholin-4-ylthiazolo[4,5-d]pyrimidine

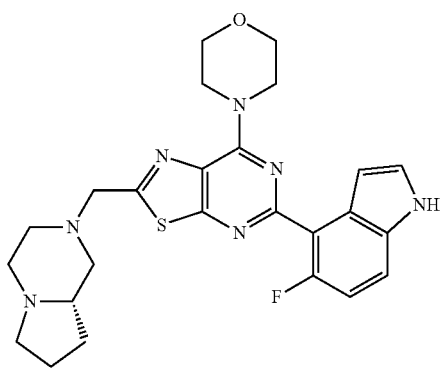

Prepared by using Suzuki coupling method G. The title compound was obtained as an orange solid (41 mg, 25%).

[M+H]+ 494.1

1H NMR (400 MHz, CDCl3): δ 1.38-1.51 (m, 1H), 1.71-1.93 (m, 3H), 2.15-2.28 (m, 3H), 2.37-2.46 (m, 1H), 2.60 (td, J=10.9, 3.0 Hz, 1H), 2.95-3.16 (m, 4H), 3.84-3.90 (m, 4H), 4.00-4.05 (m, 4H), 4.08 (d, J=5.5 Hz, 2H), 7.04 (dd, J=10.9, 8.7 Hz, 1H), 7.09-7.11 (m, 1H), 7.28 (t, J=2.9 Hz, 1H), 7.35-7.40 (m, 1H) and 8.30 (bs, 1H).

Example 16

2-(4-Azetidin-1-ylpiperidin-1-ylmethyl)-5-(5-fluoro-1H-indol-4-yl)-7-morpholin-4-ylthiazolo[4,5-d]pyrimidine

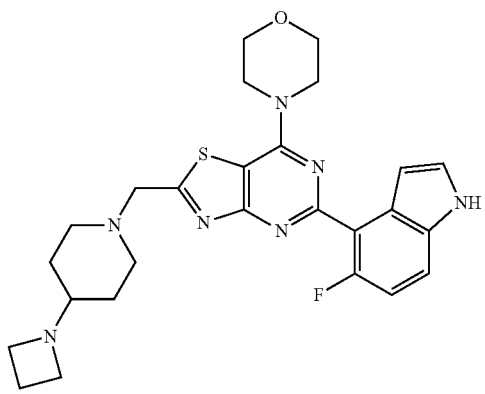

Prepared by using Suzuki coupling method G. The title compound was obtained as a yellow solid (8 mg, 7%). [M+H]⁺ 508.16. ¹H NMR (400 MHz, CDCl₃): δ 1.37-1.49 (m, 2 H), 1.71-1.79 (m, 2H), 2.00-2.11 (m, 3H), 2.37 (td, J=11.5, 2.3 Hz, 2H), 2.94-3.01 (m, 2 H), 3.20 (t, J=6.9 Hz, 4H), 3.87 (m, 4H), 4.01 (m, 6H), 7.04 (dd, J=11.2, 8.9 Hz, 1H), 7.09 (m, 1H), 7.27 (m, 1H), 7.34-7.39 (m, 1H) and 8.31 (bs, 1H).

Example 17

2-(4-Azetidin-1-ylpiperidin-1-ylmethyl)-5-(1H-indol-4-yl)-7-morpholin-4-ylthiazolo[4,5-d]pyrimidine

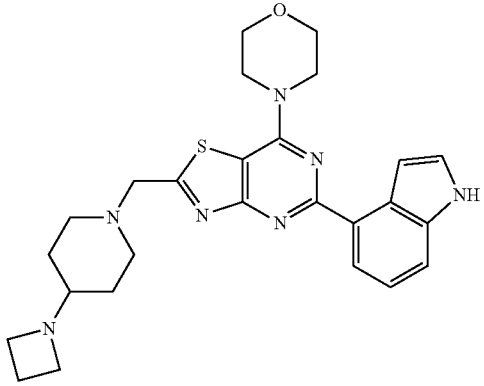

Prepared by using Suzuki coupling method E. The title compound was obtained as a yellow solid (48 mg, 52%). [M+H]⁺ 490.1. ¹H NMR (400 MHz, CDCl₃): δ 1.37-1.49 (m, 2 H), 1.71-1.79 (m, 2H), 2.01-2.12 (m, 3H), 2.37 (td, J=11.3, 2.3 Hz, 2H), 2.94-3.01 (m, 2H), 3.16-3.24 (m, 4H), 3.89-3.94 (m, 4H), 4.00 (s, 2H), 4.03-4.07 (m, 4H), 7.28-7.34 (m, 2H), 7.51 (bd, J=8.0 Hz, 1H), 7.69 (m, 1H), 8.31 (bs, 1H) and 8.36 (m, 1H).

Example 18

2-(4-Cyclopropylmethylpiperazin-1-ylmethyl)-5-(5-fluoro-1H-indol-4-yl)-7-morpholin-4-ylthiazolo[4,5-d]pyrimidine

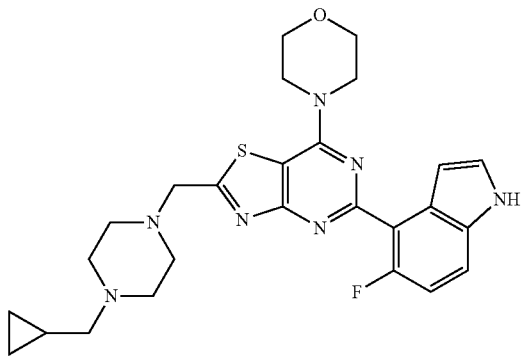

Prepared by using Suzuki coupling method G, followed by TBS-deprotection. The title compound was obtained as a yellow solid (74 mg, 35%).

[M+H]⁺ 508.1

¹H NMR (400 MHz, CDCl₃): δ 0.14 (q, J=5.0 Hz, 2H), 0.51-0.58 (m, 2H), 0.84-0.95 (m, 1H), 2.33 (d, J=5.7 Hz, 2H), 2.58-2.84 (m, 8H), 3.84-3.90 (m, 4H), 4.00-4.05 (m, 6H), 7.04 (dd, J=11.2, 8.7 Hz, 1H), 7.10 (m, 1H), 7.28 (m, 1H), 7.38 (m, 1H) and 8.31 (bs, 1H).

Example 19

{1-[5-(5-Fluoro-1H-indol-4-yl)-7-morpholin-4-ylthiazolo[4,5-d]pyrimidin-2-ylmethyl]piperidin-4-yl}dimethylamine

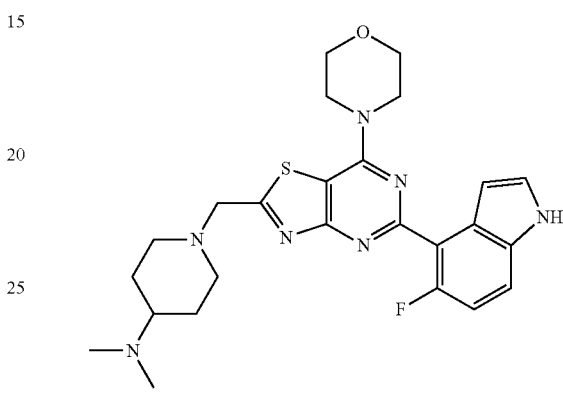

Prepared by using Suzuki coupling method D. The title compound was obtained as an orange solid (67 mg, 45%).

[M+H]⁺ 496.1

¹H NMR (400 MHz, CDCl₃): δ 1.56-1.71 (m, 4H), 1.85-1.93 (m, 2H), 2.13-2.22 (m, 1H), 2.32 (s, 6H), 3.04-3.12 (m, 2H), 3.87 (m, 4H), 4.02 (m, 6H), 7.04 (dd, J=11.1, 8.9 Hz, 1H), 7.10 (m, 1H), 7.28 (m, 1H), 7.38 (ddd, J=8.7, 3.9, 0.9 Hz, 1H) and 8.31 (bs, 1H).

Example 20

{1-[5-(1H-Indol-4-yl)-7-morpholin-4-ylthiazolo[4,5-d]pyrimidin-2-ylmethyl]piperidin-4-yl}dimethylamine

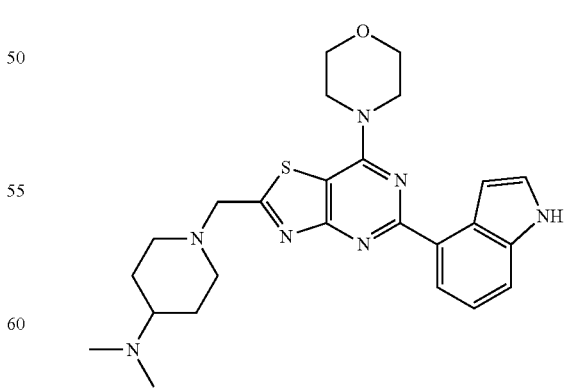

Prepared by using Suzuki coupling method E. The title compound was obtained as an orange solid (123 mg, 70%).

[M+H]⁺ 478.1

¹H NMR (400 MHz, CDCl₃): δ 1.58-1.72 (m, 4H), 1.86-1.93 (m, 2H), 2.15-2.24 (m, 1H), 2.33 (s, 6H), 3.04-3.12 (m, 2H), 3.89-3.95 (m, 4H), 4.01 (s, 2H), 4.03-4.09 (m, 4H), 7.28-7.34 (m, 2H), 7.52 (m, 1H), 7.68 (m, 1H), 8.32 (bs, 1H) and 8.36 (dd, J=7.4, 0.9 Hz, 1H).

Example 21

2-{4-[5-(5-Fluoro-1H-indol-4-yl)-7-morpholin-4-yl-thiazolo[4,5-d]pyrimidin-2-ylmethyl]-piperazin-1-yl}-isobutyramide

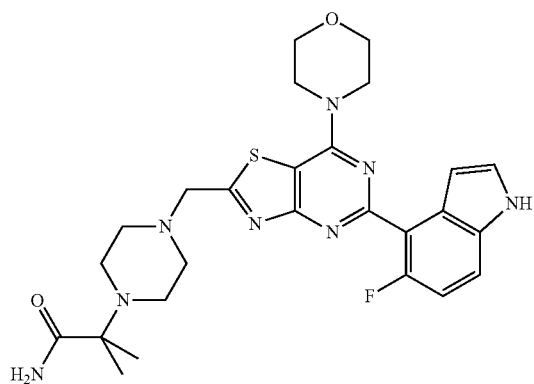

Prepared by using Suzuki coupling method G. The title compound was obtained as an orange solid (7 mg, 12%).
[M+H]⁺ 539.3
¹H NMR (400 MHz, DMSO): δ 1.10 (s, 6H), 2.49-2.54 (m, 4H, hidden), 2.66-2.71 (m, 4H), 3.76-3.79 (m, 4H), 3.90-3.93 (m, 4H), 4.03 (s, 2H), 6.72 (m, 1H), 6.96 (d, J=2.5 Hz, 1H), 7.02 (dd, J=11.5, 9.0 Hz, 1H), 7.10 (d, J=2.5 Hz, 1H), 7.45 (t, J=2.7 Hz, 1H), 7.48 (ddd, J=8.5, 4.1, 1.0 Hz, 1H) and 11.27 (s, 1H).

Example 22

2-(4-Azetidin-1-ylpiperidin-1-ylmethyl)-5-(5-fluoro-1H-indol-4-yl)-7-morpholin-4-ylthiazolo[5,4-d]pyrimidine

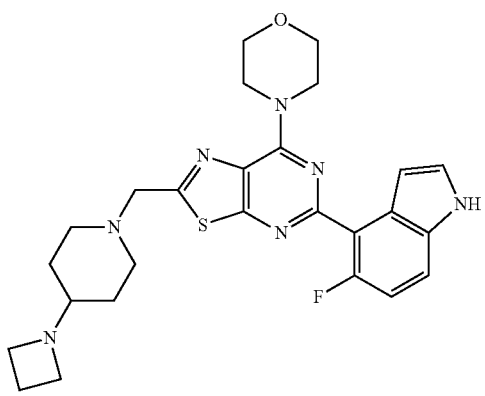

Prepared by using Suzuki coupling method G. The title compound was obtained as an off-white solid (69 mg, 43%).
[M+H]⁺ 508.2

¹H NMR (400 MHz, CDCl₃): δ 1.35-1.45 (m, 2H), 1.67-1.74 (m, 2H), 2.00-2.10 (m, 3H), 2.28 (td, J=11.1, 2.5 Hz, 2H), 2.95 (dt, J=12.1, 3.8 Hz, 2H), 3.19 (t, J=7.0 Hz, 4H), 3.84-3.87 (m, 6H), 4.39-4.44 (m, 4H), 6.92-6.94 (m, 1H), 7.04 (dd, J=11.1, 8.9 Hz, 1H), 7.29 (t, J=2.9 Hz, 1H), 7.37 (dd, J=8.9, 3.8 Hz, 1H) and 8.34 (bs, 1H).

Example 23

5-(5-Fluoro-1H-indol-4-yl)-7-morpholin-4-yl-2-piperazin-1-ylmethylthiazolo[5,4-d]pyrimidine

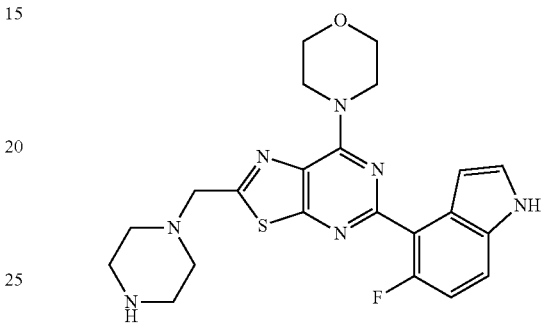

Prepared by using Suzuki coupling method G, followed by BOC-deprotection. The title compound was obtained as a white solid (46 mg, 37%).
[M+H]⁺ 454.1
¹H NMR (400 MHz, CDCl₃): δ 2.59-2.68 (m, 4H), 2.96 (t, J=4.9 Hz, 4H), 3.84-3.88 (m, 6H), 4.39-4.43 (m, 4H), 6.91-6.94 (m, 1H), 7.04 (dd, J=11.1, 8.6 Hz, 1H), 7.29 (t, J=3.2 Hz, 1H), 7.37 (ddd, J=8.9, 3.5, 0.9 Hz, 1H) and 8.34 (bs, 1H).

Example 24

2-(4-Cyclopropylpiperazin-1-ylmethyl)-5-(5-fluoro-1H-indol-4-yl)-7-morpholin-4-ylthiazolo[5,4-d]pyrimidine

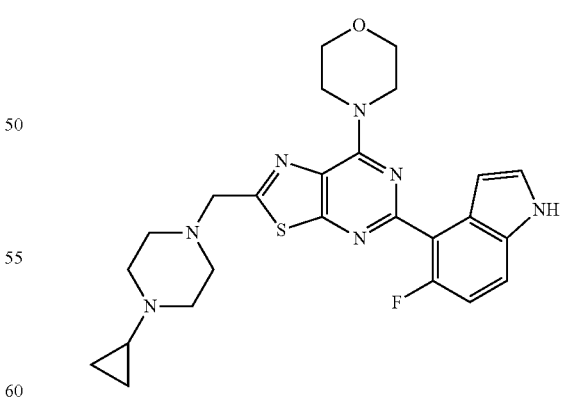

Prepared by using Suzuki coupling method G. The title compound was obtained as a white solid (63 mg, 46%).
[M+H]⁺ 494.1
¹H NMR (400 MHz, CDCl₃): δ 0.38-0.49 (m, 4H), 1.64-1.70 (m, 1H), 2.61-2.75 (m, 8H), 3.86 (t, J=5.1 Hz, 4H), 3.88 (s, 2H), 4.39-4.44 (m, 4H), 6.92-6.94 (m, 1H), 7.04 (dd, J=11.1, 8.6 Hz, 1H), 7.29 (t, J=3.2 Hz, 1H), 7.37 (ddd, J=8.9, 3.5, 0.9 Hz, 1H) and 8.31 (bs, 1 H).

Example 25

2-{4-[5-(1H-Indol-4-yl)-7-morpholin-4-ylthiazolo[5,4-d]pyrimidin-2-ylmethyl]piperazin-1-yl}isobutyramide

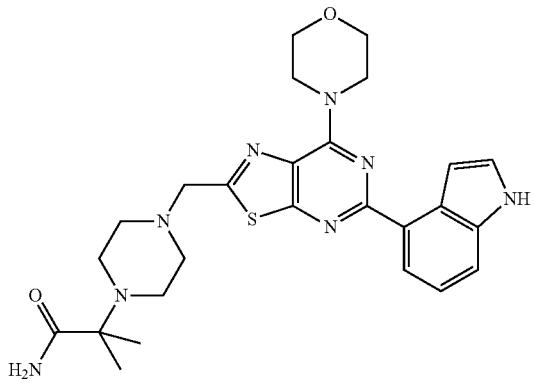

Prepared by using Suzuki coupling method F. The title compound was obtained as an off-white solid (83 mg, 47%). [M+H]+ 521.2

¹H NMR (400 MHz, DMSO): δ 1.10 (s, 6H), 2.47-2.52 (m, 4H), 2.62-2.67 (m, 4H), 3.81 (t, J=4.5 Hz, 4H), 3.92 (s, 2H), 4.33-4.38 (m, 4H), 6.97 (d, J=2.8 Hz, 1H), 7.08 (d, J=2.8 Hz, 1H), 7.20 (t, J=7.4 Hz, 1H), 7.34-7.36 (m, 1H), 7.46 (t, J=2.8 Hz, 1H), 7.54 (d, J=8.1 Hz, 1H), 8.10 (d, J=7.4 Hz, 1H) and 11.31 (bs, 1H).

Example 26

2-{4-[5-(5-Fluoro-1H-indol-4-yl)-7-morpholin-4-ylthiazolo[5,4-d]pyrimidin-2-ylmethyl]piperazin-1-yl}isobutyramide

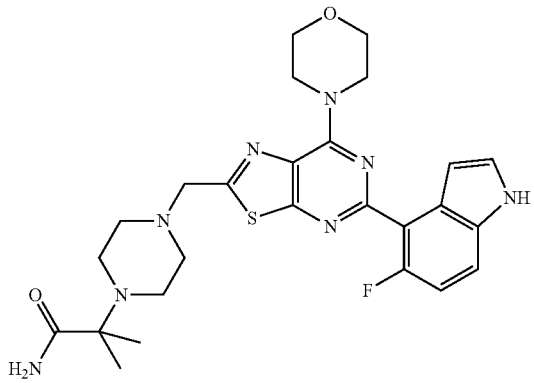

Prepared by using Suzuki coupling method G. The title compound was obtained as an off-white solid (15 mg, 17%). [M+H]+ 539.3

¹H NMR (400 MHz, DMSO): δ 1.09 (s, 6H), 2.46-2.51 (m, 4H), 2.60-2.67 (m, 4H), 3.76 (t, J=5.1 Hz, 4H), 3.93 (s, 2H), 4.27-4.32 (m, 4H), 6.69-6.71 (m, 1H), 6.97 (d, J=3.5 Hz, 1H), 7.00 (dd, J=11.1, 8.9 Hz, 1H), 7.08 (d, J=3.5 Hz, 1H), 7.44-7.49 (m, 2H), and 11.31 (bs, 1H).

Example 27

{1-[5-(1H-Indol-4-yl)-7-morpholin-4-ylthiazolo[5,4-d]pyrimidin-2-ylmethyl]piperidin-4-yl}dimethylamine

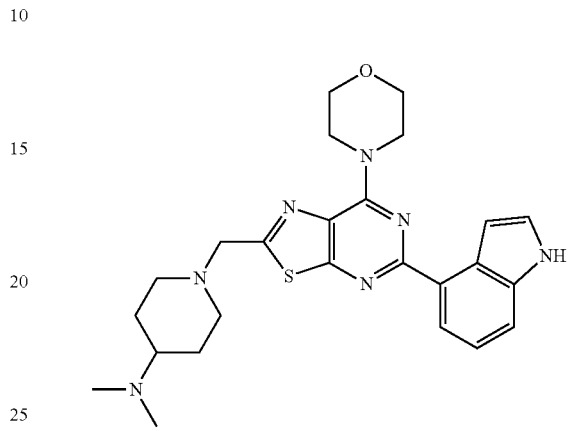

Prepared by using Suzuki coupling method B. The title compound was obtained as a tan solid (75 mg, 62%). [M+H]+ 478.2

¹H NMR (400 MHz, CDCl₃): δ 1.59-1.71 (m, 2H), 1.87 (d, J=12.6 Hz, 2H), 2.25 (dt, J=12.2, 1.8 Hz, 3H), 2.35 (s, 6H), 3.07 (d, J=12.0 Hz, 2H), 3.87 (s, 2H), 3.90 (t, J=4.3 Hz, 4 H), 4.43-4.46 (m, 4H), 7.30 (t, J=7.5 Hz, 1H), 7.34 (t, J=2.5 Hz, 1H), 7.50 (d, J=8.7 Hz, 1H), 7.51-7.53 (m, 1H), 8.18 (d, J=7.1 Hz, 1H) and 8.30 (bs, 1H).

Example 28

5-(1H-Indol-4-yl)-7-morpholin-4-yl-2-(4-morpholin-4-ylpiperidin-1-ylmethyl)thiazolo[5,4-d]pyrimidine

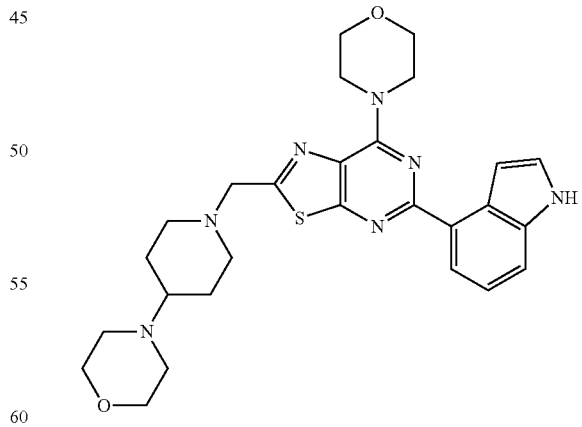

Prepared by using Suzuki coupling method B. The title compound was obtained as a tan solid (38 mg, 64%). [M+H]+ 520.2

¹H NMR (400 MHz, CDCl₃): δ 1.63 (qd, J=11.3, 3.7 Hz, 2H), 1.87 (d, J=11.3 Hz, 2H), 2.18-2.29 (m, 3H), 2.55-2.59 (m, 4H), 3.07 (d, J=11.9 Hz, 2H), 3.72-3.76 (m, 4H), 3.86 (s,

2H), 3.90 (t, J=5.1 Hz, 4H), 4.43-4.47 (m, 4H), 7.30 (t, J=8.1 Hz, 1H), 7.34 (t, J=2.9 Hz, 1H), 7.49-7.53 (m, 2H), 8.18 (d, J=7.6 Hz, 1H) and 8.29 (bs, 1H).

Example 29

5-(5-Fluoro-1H-indol-4-yl)-7-morpholin-4-yl-2-(4-morpholin-4-ylpiperidin-1-ylmethyl)thiazolo[5,4-d]pyrimidine

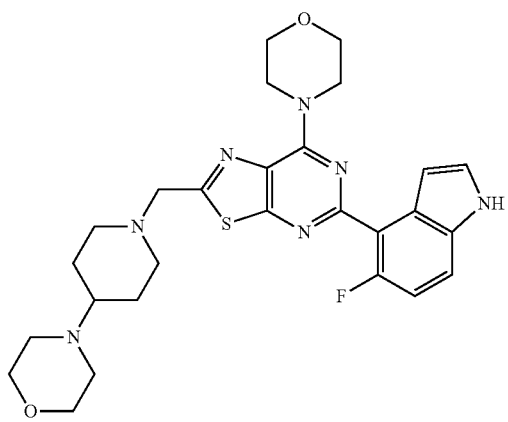

Prepared by using Suzuki coupling method C. The title compound was obtained as a tan solid (27 mg, 45%). [M+H]+ 538.2. $^1$H NMR (400 MHz, CDCl$_3$): δ 1.63 (qd, J=11.3, 3.7 Hz, 2H), 1.87 (d, J=11.3 Hz, 2H), 2.18-2.29 (m, 3H), 2.55-2.59 (m, 4H), 3.07 (d, J=11.9 Hz, 2H), 3.72-3.76 (m, 4H), 3.84-3.87 (m, 6H), 4.40 (m, 4H), 6.92-6.94 (m, 1H), 7.05 (dd, J=11.0, 8.5 Hz, 1H), 7.29 (t, J=2.0 Hz, 1H), 7.38 (dd, J=8.4, 4.2 Hz, 1H) and 8.24 (bs, 1H).

Example 30

Biological Testing

Compounds of the invention, prepared as described in the preceding Examples, were submitted to the following biological assay:
PI3K Biochemical Screening Compound inhibition of PI3K was determined in a radiometric assay using purified, recombinant enzyme and ATP at a concentration of 1 uM. All compounds were serially diluted in 100% DMSO. The kinase reaction was incubated for 1 hour at room temperature, and the reaction was terminated by the addition of PBS. IC$_{50}$ values were subsequently determined using sigmoidal dose-response curve fit (variable slope). All of the compounds tested had an IC$_{50}$ against PI3K of 50 μM or less. Typically the IC$_{50}$ against the p110δ isoform of PI3K was less than 500 nM.

Example 31

Tablet Composition

Tablets, each weighing 0.15 g and containing 25 mg of a compound of the invention were manufactured as follows:
Composition for 10,000 tablets
Compound of the invention (250 g)
Lactose (800 g)
Corn starch (415 g)
Talc powder (30 g)
Magnesium stearate (5 g)

The compound of the invention, lactose and half of the corn starch were mixed. The mixture was then forced through a sieve 0.5 mm mesh size. Corn starch (10 g) is suspended in warm water (90 ml). The resulting paste was used to granulate the powder. The granulate was dried and broken up into small fragments on a sieve of 1.4 mm mesh size. The remaining quantity of starch, talc and magnesium was added, carefully mixed and processed into tablets.

Example 32

Injectable Formulation

| | |
|---|---|
| Compound of the invention | 200 mg |
| Hydrochloric Acid Solution 0.1M or Sodium Hydroxide Solution 0.1M q.s. to pH | 4.0 to 7.0 |
| Sterile water q.s. to | 10 ml |

The compound of the invention was dissolved in most of the water (35°-40° C.) and the pH adjusted to between 4.0 and 7.0 with the hydrochloric acid or the sodium hydroxide as appropriate. The batch was then made up to volume with water and filtered through a sterile micropore filter into a sterile 10 ml amber glass vial (type 1) and sealed with sterile closures and overseals.

Example 33

Intramuscular Injection

| | | |
|---|---|---|
| Compound of the invention | 200 | mg |
| Benzyl Alcohol | 0.10 | g |
| Glycofurol 75 | 1.45 | g |
| Water for injection q.s to | 3.00 | ml |

The compound of the invention was dissolved in the glycofurol. The benzyl alcohol was then added and dissolved, and water added to 3 ml. The mixture was then filtered through a sterile micropore filter and sealed in sterile 3 ml glass vials (type 1).

Example 34

Syrup Formulation

| | | |
|---|---|---|
| Compound of invention | 250 | mg |
| Sorbitol Solution | 1.50 | g |
| Glycerol | 2.00 | g |
| Sodium benzoate | 0.005 | g |
| Flavour | 0.0125 | ml |
| Purified Water q.s. to | 5.00 | ml |

The compound of the invention was dissolved in a mixture of the glycerol and most of the purified water. An aqueous solution of the sodium benzoate was then added to the solution, followed by addition of the sorbital solution and finally the flavour. The volume was made up with purified water and mixed well.

The invention claimed is:

1. A method of treating a disease or disorder comprising the administration of a thiazolopyrimidine compound of formula (I) to a human or animal patient wherein the disease or disorder is inflammation; and wherein the thiazolopyrimidine compound of formula (I) has the structure:

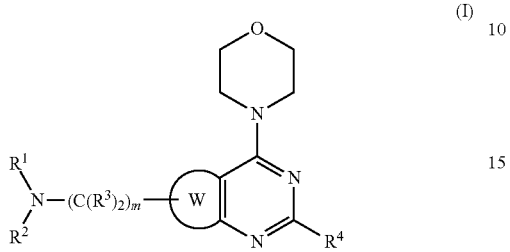

wherein
W represents a thiazole ring;
$R^1$ and $R^2$ form, together with the N atom to which they are attached, a group of the following formula (IIa):

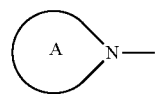

in which A is selected from:
(a) a 4- to 7-membered saturated N-containing heterocyclic ring which includes 0 or 1 additional heteroatoms selected from N, S and O, the ring being unsubstituted or substituted;
(b) a 4- to 7-membered saturated N-containing heterocyclic ring which includes 0 or 1 additional heteroatoms selected from N, S and O, the ring being fused to a second ring selected from a 4- to 7-membered saturated N-containing heterocyclic ring as defined above, a 5- to 12-membered unsaturated heterocyclic ring, a 5- to 7-membered saturated O-containing heterocyclic ring, a 3- to 12-membered saturated carbocyclic ring and an unsaturated 5- to 12-membered carbocyclic ring to form a heteropolycyclic ring system, the heteropolycyclic ring system being unsubstituted or substituted;
(c) a 4- to 7-membered saturated N-containing heterocyclic ring which includes 0 or 1 additional heteroatoms selected from N, S and O and which further comprises, linking two constituent atoms of the ring, a bridgehead group selected from —(CR'$_2$)$_n$— and —(CR'$_2$)$_r$—O—(CR'$_2$)$_s$— wherein each R' is independently H or $C_1$-$C_6$ alkyl, n is 1, 2 or 3, r is 0 or 1 and s is 0 or 1, the remaining ring positions being unsubstituted or substituted; and
(d) a group of formula (IIb):

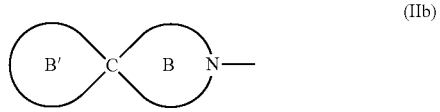

wherein ring B is a 4- to 7-membered saturated N-containing heterocyclic ring which includes 0 or 1 additional heteroatoms selected from N, S and O and ring B' is a 3- to 12-membered saturated carbocyclic ring, a 5- to 7-membered saturated O-containing heterocyclic ring or a 4- to 7-membered saturated N-containing heterocyclic ring as defined above, each of B and B' being unsubstituted or substituted;

or one of $R^1$ and $R^2$ is $C_1$-$C_6$ alkyl and the other of $R^1$ and $R^2$ is selected from a 3- to 12-membered saturated carbocyclic group which is unsubstituted or substituted, a 5- to 12-membered unsaturated carbocyclic group which is unsubstituted or substituted, a 5- to 12-membered unsaturated heterocyclic group which is unsubstituted or substituted, a 4- to 12-membered saturated heterocyclic group which is unsubstituted or substituted and a $C_1$-$C_6$ alkyl group which is substituted by a group selected from a 3- to 12-membered saturated carbocyclic group which is unsubstituted or substituted, a 5- to 12-membered unsaturated carbocyclic group which is unsubstituted or substituted, a 5- to 12-membered unsaturated heterocyclic group which is unsubstituted or substituted and a 4- to 12-membered saturated heterocyclic group which is unsubstituted or substituted;
m is 0, 1 or 2;
$R^3$ is H or $C_1$-$C_6$ alkyl; and
$R^4$ is an indole group which is unsubstituted or substituted;
or a pharmaceutically acceptable salt thereof.

2. The method of claim 1 wherein the thiazolopyrimidine compound is of formula (Ia):

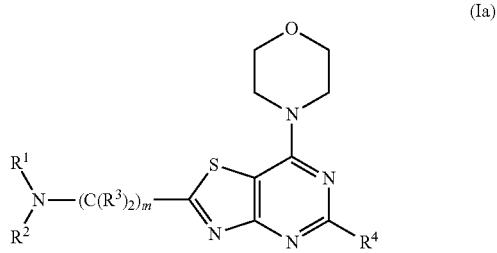

wherein $R^1$, $R^2$, $R^3$, $R^4$ and m are as defined in claim 1.

3. The method of claim 1 wherein the thiazolopyrimidine compound is of formula (Ib):

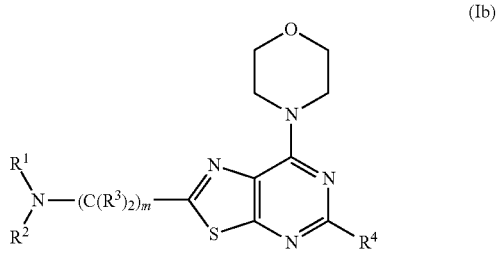

wherein $R^1$, $R^2$, $R^3$, $R^4$ and m are as defined in claim 1.

4. The method of claim 1 wherein $R^4$ is an indole group which is unsubstituted or substituted by a group selected from CN, halo, —C(O)NR$_2$, halo($C_1$-$C_6$)alkyl, —SO$_2$R, —SO$_2$NR$_2$, and a 5-membered heteroaryl group containing 1, 2, 3 or 4 heteroatoms selected from 0, N and S, wherein R is H or $C_1$-$C_6$ alkyl.

5. The method of claim 1 wherein $R^3$ is H and m is 1.

6. The method of claim 1 wherein the 4- to 7-membered saturated N-containing heterocyclic ring is selected from structures (i)-(ix):

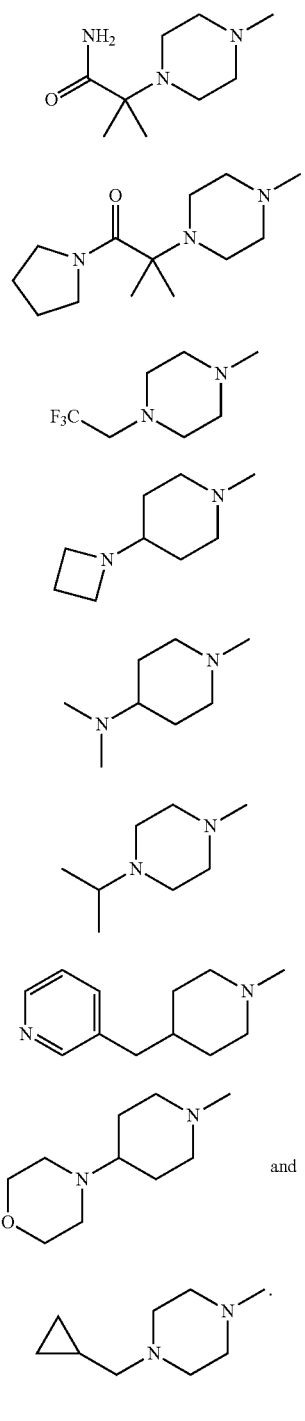
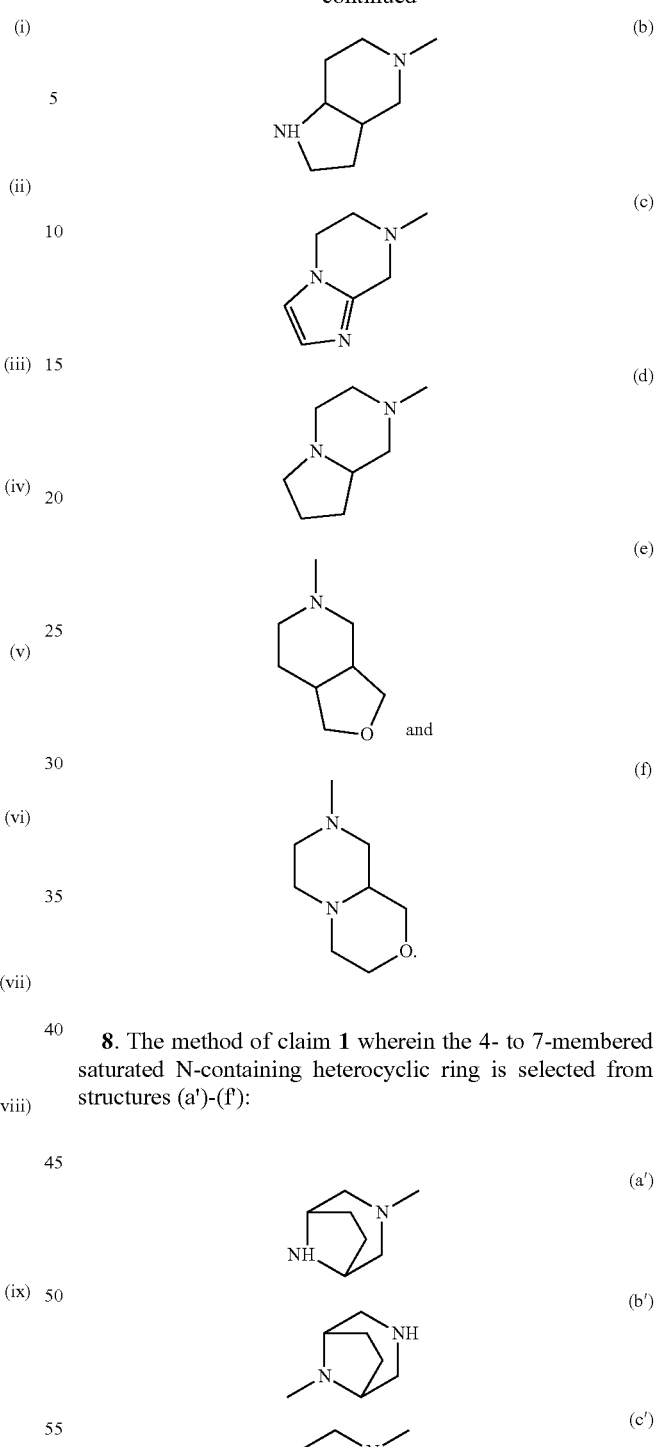
7. The method of claim 1 wherein the 4- to 7-membered saturated N-containing heterocyclic ring is selected from structures (a)-(f):
8. The method of claim 1 wherein the 4- to 7-membered saturated N-containing heterocyclic ring is selected from structures (a')-(f'):
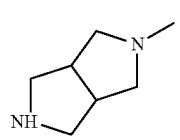
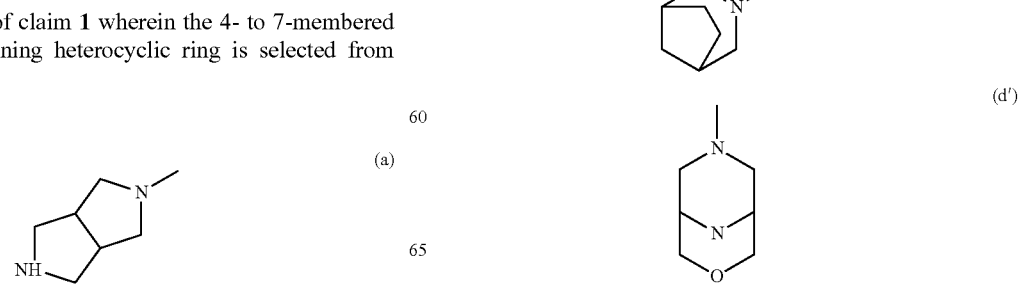

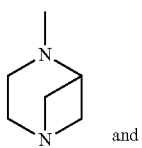 (e')

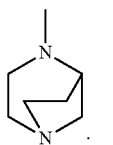 (f')

9. The method of claim 1 wherein the 4- to 7-membered saturated N-containing heterocyclic ring is selected from structures (i')-(x'):

 (i')

 (ii')

 (iii')

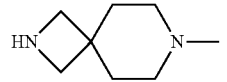 (iv')

(v')

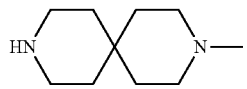 (vi')

 (vii')

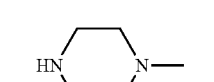 (viii')

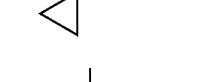 (ix')

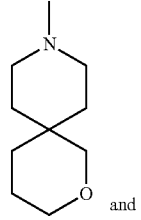 and

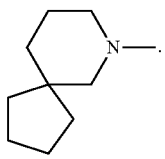 (x')

10. The method of claim 1 wherein the indole group is indol-4-yl.

11. The method of claim 10 wherein the indol-4-yl is unsubstituted or substituted with one or more fluorine.

12. The method of claim 1 wherein the thiazolopyrimidine compound is selected from:
   5-(6-Fluoro-1H-indol-4-yl)-2-(hexahydro-pyrrolo[3,4-c]pyrrol-2-ylmethyl)-7-morpholin-4-yl-thiazolo[4,5-d]pyrimidine;
   5-(6-Fluoro-1H-indol-4-yl)-2-(hexahydro-pyrrolo[3,4-c]pyrrol-2-ylmethyl)-7-morpholin-4-yl-thiazolo[5,4-d]pyrimidine;
   2-(2,7-Diaza-spiro[3.5]non-2-ylmethyl)-5-(1H-indol-4-yl)-7-morpholin-4-yl-thiazolo[5,4-d]pyrimidine;
   2-(2,7-Diaza-spiro[3.5]non-2-ylmethyl)-5-(6-fluoro-1H-indol-4-yl)-7-morpholin-4-yl-thiazolo[5,4-d]pyrimidine;
   2-(2,7-Diaza-spiro[3.5]non-2-ylmethyl)-5-(5-fluoro-1H-indol-4-yl)-7-morpholin-4-yl-thiazolo[5,4-d]pyrimidine;
   2-(3,8-Diaza-bicyclo[3.2.1]oct-3-ylmethyl)-5-(1H-indol-4-yl)-7-morpholin-4-yl-thiazolo[5,4-d]pyrimidine;
   2-(4-Azetidin-1-yl-piperidin-1-ylmethyl)-5-(1H-indol-4-yl)-7-morpholin-4-yl-thiazolo[5,4-d]pyrimidine;
   2-[(S)-1-(Hexahydro-pyrrolo[1,2-a]pyrazin-2-yl)methyl]-5-(1H-indol-4-yl)-7-morpholin-4-yl-thiazolo[5,4-d]pyrimidine;
   2-(3,5-Dimethyl-piperazin-1-ylmethyl)-5-(1H-indol-4-yl)-7-morpholin-4-yl-thiazolo[5,4-d]pyrimidine;
   2-(2,7-Diaza-spiro[3.5]non-2-ylmethyl)-5-(6-fluoro-1H-indol-4-yl)-7-morpholin-4-yl-thiazolo[4,5-d]pyrimidine formate;
   5-(1H-Indol-4-yl)-7-morpholin-4-yl-2-(4-morpholin-4-yl-piperidin-1-ylmethyl)-thiazolo[4,5-d]pyrimidine;
   2-(3,3-Dimethylpiperazin-1-ylmethyl)-5-(5-fluoro-1H-indol-4-yl)-7-morpholin-4-ylthiazolo[4,5-d]pyrimidine;
   5-(5-Fluoro-1H-indol-4-yl)-7-morpholin-4-yl-2-(4-morpholin-4-ylpiperidin-1-ylmethyl)thiazolo[4,5-d]pyrimidine;
   5-(1H-Indol-4-yl)-7-morpholin-4-yl-2-(4-morpholin-4-ylpiperidin-1-ylmethyl)thiazolo[4,5-d]pyrimidine;
   5-(5-Fluoro-1H-indol-4-yl)-2-[(S)-1-(hexahydro-pyrrolo[1,2-c]pyrazin-2-yl)methyl]-7-morpholin-4-ylthiazolo[4,5-d]pyrimidine;
   2-(4-Azetidin-1-ylpiperidin-1-ylmethyl)-5-(5-fluoro-1H-indol-4-yl)-7-morpholin-4-ylthiazolo[4,5-d]pyrimidine;
   2-(4-Azetidin-1-ylpiperidin-1-ylmethyl)-5-(1H-indol-4-yl)-7-morpholin-4-ylthiazolo[4,5-d]pyrimidine;
   2-(4-Cyclopropylmethylpiperazin-1-ylmethyl)-5-(5-fluoro-1H-indol-4-yl)-7-morpholin-4-ylthiazolo[4,5-d]pyrimidine;
   {1-[5-(5-Fluoro-1H-indol-4-yl)-7-morpholin-4-ylthiazolo[4,5-d]pyrimidin-2-ylmethyl]piperidin-4-yl}dimethylamine;

{1-[5-(1H-Indol-4-yl)-7-morpholin-4-ylthiazolo[4,5-d]pyrimidin-2-ylmethyl]piperidin-4-yl}dimethylamine;

2-{4-[5-(5-Fluoro-1H-indol-4-yl)-7-morpholin-4-yl-thiazolo[4,5-d]pyrimidin-2-ylmethyl]-piperazin-1-yl}-isobutyramide;

2-(4-Azetidin-1-ylpiperidin-1-ylmethyl)-5-(5-fluoro-1H-indol-4-yl)-7-morpholin-4-ylthiazolo[5,4-d]pyrimidine;

5-(5-Fluoro-1H-indol-4-yl)-7-morpholin-4-yl-2-piperazin-1-ylmethylthiazolo[5,4-d]pyrimidine;

2-(4-Cyclopropylpiperazin-1-ylmethyl)-5-(5-fluoro-1H-indol-4-yl)-7-morpholin-4-ylthiazolo[5,4-d]pyrimidine;

2-{4-[5-(1H-Indol-4-yl)-7-morpholin-4-ylthiazolo[5,4-d]pyrimidin-2-ylmethyl]piperazin-1-yl}isobutyramide;

2-{4-[5-(5-Fluoro-1H-indol-4-yl)-7-morpholin-4-ylthiazolo[5,4-d]pyrimidin-2-ylmethyl]piperazin-1-yl}isobutyramide;

{1-[5-(1H-Indol-4-yl)-7-morpholin-4-ylthiazolo[5,4-d]pyrimidin-2-ylmethyl]piperidin-4-yl}dimethylamine;

5-(1H-Indol-4-yl)-7-morpholin-4-yl-2-(4-morpholin-4-ylpiperidin-1-ylmethyl)thiazolo[5,4-d]pyrimidine; and 5-(5-Fluoro-1H-indol-4-yl)-7-morpholin-4-yl-2-(4-morpholin-4-ylpiperidin-1-ylmethyl)thiazolo[5,4-d]pyrimidine.

\* \* \* \* \*